US008426683B2

(12) United States Patent
Frankard

(10) Patent No.: US 8,426,683 B2
(45) Date of Patent: Apr. 23, 2013

(54) PLANTS HAVING INCREASED YIELD AND A METHOD FOR MAKING THE SAME

(75) Inventor: Valerie Frankard, Waterloo (BE)

(73) Assignee: CropDesign N.V., Zwijnaarde (BE)

( * ) Notice: Subject to any disclaimer, the term of this patent is extended or adjusted under 35 U.S.C. 154(b) by 1428 days.

(21) Appl. No.: 11/795,976

(22) PCT Filed: Jan. 27, 2006

(86) PCT No.: PCT/EP2006/050489
§ 371 (c)(1),
(2), (4) Date: Aug. 10, 2007

(87) PCT Pub. No.: WO2006/079655
PCT Pub. Date: Aug. 3, 2006

(65) Prior Publication Data
US 2010/0212041 A1 Aug. 19, 2010

Related U.S. Application Data

(60) Provisional application No. 60/649,041, filed on Feb. 1, 2005, provisional application No. 60/730,403, filed on Oct. 26, 2005.

(30) Foreign Application Priority Data

Jan. 27, 2005 (EP) .................................. 01500537

(51) Int. Cl.
A01H 1/00       (2006.01)
A01H 5/00       (2006.01)
C12N 15/82      (2006.01)
C12N 5/14       (2006.01)
C12N 15/63      (2006.01)

(52) U.S. Cl.
USPC ........... 800/295; 800/278; 800/298; 800/320; 435/320.1; 435/419; 435/468

(58) Field of Classification Search .................... None
See application file for complete search history.

(56) References Cited

U.S. PATENT DOCUMENTS

| 2004/0034888 | A1 | 2/2004 | Liu et al. |
| 2004/0045049 | A1 | 3/2004 | Zhang et al. |
| 2004/0072289 | A1 | 4/2004 | Hwang et al. |
| 2005/0086718 | A1 | 4/2005 | Heard et al. |
| 2007/0245432 | A1* | 10/2007 | Reuzeau ....................... 800/290 |
| 2010/0199382 | A1 | 8/2010 | Frankard et al. |
| 2010/0218271 | A1 | 8/2010 | Sanz Molinero et al. |

FOREIGN PATENT DOCUMENTS

| EP | 1 033 405 A2 | 9/2000 |
| EP | 1033405 A2 * | 9/2000 |
| JP | 2002-356498 A | 12/2002 |
| JP | 2004350553 | 12/2004 |
| WO | WO-00/66746 A1 | 11/2000 |
| WO | WO-2006/008271 A1 | 1/2006 |
| WO | WO-2006/079655 A2 | 8/2006 |

OTHER PUBLICATIONS

Jeong et al. (Plant Journal, 36:94-104, 2003).*
Kim et al. (Plant Journal, 36:94-104, 2003).*
Kim et al. (PNAS, 101:13374-13379, 2004).*
Doerks et al., (TIG, 14:248-250, 1998).*
Smith et al. (Nature Biotechnology, 15:1222-1223, 1997).*
Wells, Biochemistry 29:8509-8517, 1990.*
Ngo et al., The Protein Folding Problem and Tertiary Structure Prediction, K. Merz., and S. Le Grand (eds.) pp. 492-495,1994.*
Thornton et al. (Nature structural Biology, structural genomics supplement, Nov. 2000.*
Keskin et al. (Protein Science, 13:1043-1055, 2004.*
Yano et al. (Lung Cancer., 44:391-397, 2004).*
Van Camp (Curr. Opin. Biotech., 16:147-153, 2005).*
van der Knaap et al. (Plant Physiol., 122:695-704, 2000).*
Jiang et al. (Crop Science, 40:1729-1741, 2000).*
de Pater et al. (Plant Journal, 2:837-844, 1992).*
Knaap et al. (Plant Physiol., 122:695-704, 2000).*
Kim, J.-H., et al., "Studies on the function of OsGRF1-like (AtGRL) genes in Arabidopsis", Poster, Annual Meeting on the American Society of Plant Biologists on Plant Biology (2002), p. 56.
Kim, J. H. et al., "The AtGRF family of putative transcription factors is involved in leaf and cotyledon growth in Arabidopsis", The Plant Journal, vol. 36, (2003), pp. 94-104.
Kim, J. H., et al., "A Transcriptional Coactivator, AtGIF1, is involved in regulating leaf growth and morphology in Arabidopsis", PNAS, vol. 101, No. 36, (2004), pp. 13374-13379.
Mauch, F., "Exploring the Regulation of Leaf Growth", Checkbiotech, (2004), p. 1.
Caponigro, G., et al., "Functional Analysis of Expressed Peptides that Bind Yeast STE Proteins", Journal of Biotechnology, vol. 103, (2003), pp. 213-225.
Luban, J., et al., "The Yeast Two-Hybrid System for Studying Protein-Protein Interactions", Current Opinion Biotechnology, vol. 6, (1995), pp. 59-64.
Becerra, C., et al., "Ankyrin Repeat-Containing Proteins in Arabidopsis: Characterization of a Novel and Abundant Group of Genes Coding Ankyrin-Transmembrane Proteins", Gene, vol. 340, (2004), pp. 111-121.
Bork, P., "Hundreds of Ankyrin-like Repeats in Functionally Diverse Proteins: Mobile Modules That Cross Phyla Horizontally?", Proteins: Structure, Function, and Genetics, vol. 17, (1993), pp. 363-374.
Brown, R. S., "Zinc Finger Proteins: Getting a Grip on RNA", Current Opinion in Structural Biology, vol. 15, (2005), pp. 94-98.
Cheuk, R., et al., "Arabidopsis thaliana At2g41900/T6D20.20 mRNA, complete cds", Database EMBL Accession No. AY093957, Apr. 29, 2002.
Doerks, et al., "Protein annotation: detective work for function prediction," TIG (Jun. 1998), vol. 14, No. 6, pp. 248-250.

(Continued)

Primary Examiner — Vinod Kumar
(74) Attorney, Agent, or Firm — Novak Druce Connolly Bove + Quigg LLP

(57) ABSTRACT

The present invention concerns a method for increasing plant yield by modulating expression in a plant of a nucleic acid encoding a synovial sarcoma translocation (SYT) polypeptide or a homologue thereof. One such method comprises introducing into a plant a SYT nucleic acid or variant thereof. The invention also relates to transgenic plants having introduced therein a SYT nucleic acid or variant thereof, which plants have increased yield relative to corresponding wild type plants. The present invention also concerns constructs useful in the methods of the invention.

39 Claims, 36 Drawing Sheets

OTHER PUBLICATIONS

Horiguchi, G., et al., "Coordination of cell proliferation and cell expansion in the control of leaf size in *Arabidopsis thaliana*," *J Plant Res* (2006), vol. 119, pp. 37-42.

Horiguchi, G., et al., "The transcription factor AtGRF5 and the transcription coactivator AN3 regulate cell proliferation in leaf primordia of *Arabidopsis thaliana*," *The Plant Journal* (2005), vol. 43, pp. 68-78.

Jiang, J., et al., "High Efficiency Transformation of U.S. Rice Lines from Mature Seed-Derived Calli and Segregation of Glufosinate Resistance under Field Conditions," *Crop Science* (2000), vol. 40, pp. 1729-1741.

Keskin, O., et al., "A new, structurally nonredundant, diverse data set of protein-potein interfaces and its implications," *Protein Science* (2004), vol. 13, pp. 1043-1055.

Kuriyama, H., et al., "Characterization and Chromosomal Mapping of a Novel Human Gene, *ANKHZN*", Gene, vol. 253, (2000), pp. 151-160.

Ngo, J.T., et al., "Computational Complexity, Protein Structure Prediction, and the Levinthal Paradox," *The Protein Folding Problem and Tertiary Structure Prediction* (1994), K. Merz and S. LeGrand (eds.), pp. 491-495.

Schena, M., et al., "The *HAT4* Gene of *Arabidopsis* Encodes a Developmental Regulator", Genes & Development, vol. 7, (1993), pp. 367-379.

Smith, T.F., et al., "The challenges of genome sequence annotation or 'The devil is in the details'," *Nature Biotechnology* (Nov. 1997), vol. 15, pp. 1222-1223.

Thornton, J.M., et al., "From structure to function: Approaches and limitations," *Nature Structural Biology, Structural Genomics Supplement* (Nov. 2000), pp. 991-994.

Van Camp, W., "Yield enhancement genes: seeds for growth," *Current Opinion in Biotechnology* (2005), vol. 16, pp. 147-153.

Van Der Knaap, E., et al., "A Novel Gibberellin-Induced Gene from Rice and Its Potential Regulatory Role in Stem Growth," *Plant Physiology* (Mar. 2000), vol. 122, pp. 695-704.

Wells, J.A., "Additivity of Mutational Effects in Proteins," *Biochemistry* (Sep. 18, 1990), vol. 29, No. 37, pp. 8509-8517.

Yano, M., et al., "*SYT-SSX* fusioin genes in synovial sarcoma of the thorax," *Lung Cancer* (2004), vol. 44, pp. 391-397.

Zhang, J., et al., "Thalecress transcription factor cDNA #115", Database EBI Accession No. AD001816, Jul. 1, 2004.

Zhang, J., et al., "Thalecress transcription factor protein #115", Database EBI Accession No, AD001817, Jul. 1, 2004.

Li, Z., et al., "*PEI1*, an Embryo-Specific Zinc Finger Protein Gene Required for Heart-Stage Embryo Formation in *Arabidopsis*", The Plant Cell, vol. 10, (1998), pp. 383-398.

Meijer, A. H., et al., "Transcriptional Repression by Oshox1, A Novel Homeodomain Leucine Zipper Protein From Rice", The Plant Journal, vol. 11, No. 2, (1997), pp. 263-276.

Wang, E., et al., "Control of Rice Grain-filling and Yield by a Gene With a Potential Signature of Domestication", Nature Genetics, vol. 40, No, 11, (2008), pp. 1370-1374.

Allen, D., et al., "Sequence 11 from Patent WO2006134162", Database EMBL Accession No. CS479909, Feb. 19, 2007.

Kim, J., et al., "Transcription activator [*Arabidopsis thaliana*]", Database GenBank Accession No. AAM52880, Aug. 20, 2004.

Kim, J., et al., "GRF1-interacting factor 1 [*Arabidopsis thaliana*]", Database GenBank Accession No. AAM52881, Sep. 8, 2004.

* cited by examiner

Plant SYT-like polypeptide structure

Met SNH Met QG

Mammalian SYT-like polypeptide structure

Met SNH Met QPGY

|  |  | SNH domain (continued) | Met-rich / QG-rich domain |
|---|---|---|---|
|  |  | 51 | 100 |
| Brana_SYT1 | (40) | VESQNSGKLSECAENQARLQRNLMYLAAIADSQPQ | ----------PPSVHS |
| Aqufo_SYT1 | (38) | LENQNSGKVSECAENQARLQRNLMYLAAIADSQPQ | ----------PPNMHA |
| Picsi_SYT1 | (40) | LDNQNLGKLNECAQYQAKLQQNLMYLAAIADSQPQ | ----------AQTAHA |
| Pinta_SYT1 | (40) | LDNQNLGKLNECAQYQAKLQQNLMYLAAIADSQPQ | ----------AQTAHA |
| Poptr_SYT1 | (40) | VESQNSGKLSECAENQARLQQNLMYLAAIADSQPQ | ----------PPTMHA |
| Vitvi_SYT1 | (40) | VESQNSGKITECAENQARLQRNLMYLAAIADSQPQ | ----------PPTMHA |
| Soltu_SYT1 | (40) | VESQNSGKLSECAENQARLQRNLMYLAAIADSQPQ | ----------PSSMHS |
| Lyces_SYT1 | (40) | VESQNSGKLSECAENQARLQRNLMYLAAIADSQPQ | ----------PSSMHS |
| Goshi_SYT1 | (40) | VESQNSGKLSECAENQARLQRNLMYLAAIADSQPQ | ----------PPTVHA |
| Zeama_SYT1 | (43) | LDNQNNGKAEECERHQAKLQHNLMYLAAIADSQPP | ----------QTAPLS |
| Medtr_SYT1 | (40) | VESQNTGKITECAENQSRLQRNLMYLAAIADSQPQ | ----------PPTMPG |
| Citsi_SYT1 | (40) | VESQNSGKLSECAENQARLQRNLMYLAAIADSQPQ | ----------PPSVHA |
| Arath_SYT1 | (40) | VESQNSGKLSECAENQARLQRNLMYLAAIADSQPQ | ----------PPSVHS |
| Aspof_SYT1 | (41) | LENQNSGKADECAENQAKLQRNLMYLAAIADSQP  | ----------QVPTIA |
| Orysa_SYT1 | (43) | LDNQNNGKVEECARNQAKLQHNLMYLAAIADSQPP | ----------QTAAMS |
| Sacof_SYT1 | (43) | LDNQNNGKVEECERHQAKLQHNLMYLAAIADSQPP | ----------QTAPLS |
| Allce_SYT2 | (39) | LDNQNIGRLNECAQYQALQKNLIYLAAIADAQP   | ----------QSPAVRL |
| Lacse_SYT2 | (40) | MSNINIGKLAECAQYQALLQKNLMYLAAIADIQP  | PTPTP---TLNISYXM |
| Horvu_SYT2 | (42) | LENQNLGKLAECAQYQALQKNLIYLAAIADIQP   | ----------QTSVSRP |
| Brana_SYT2 | (46) | MENQNIGKLAECAQYQALLQKNLMYLAAIADIQP  | PPSTAGATPPPAMASQ |
| Sacof_SYT2 | (40) | LENQNLGKLAECAQYQSQLQKNLIYLAAIADIQP  | ----------QTAVSRP |
| Triae_SYT2 | (42) | LENQNLGKLAECAQYQAQLQKNLIYLAAIADIQP  | ----------QTTVSRP |
| Maldo_SYT2 | (39) | LDNQNIGKLAECAQYQALLQKNLMYLAAIADIQPQ | ----------APAAPP |
| Goshi_SYT2 | (39) | LDNQNIGKLAECAQYQAQLQKNLMYLAAIADIQPQS | ---------TPAMSP |
| Glyso_SYT2 | (39) | LDNQNIGKLAECAQYQAQLQKNLMYLAAIADIQPQ | ----------TPAMPP |
| Glyma_SYT2 | (39) | LDNQNIGKLAECAQYQAQLQKNLMYLAAIADIQPQ | ----------TPAMPP |
| Eupes_SYT2 | (39) | LDNQNIGKLAECAQYQALLQKNLMYLAAIADQPQ  | ----------TPPMPP |
| Arath_SYT2 | (42) | MENQNIGKLAECAQYQALLQKNLMYLAAIADIQP  | PPPTPGPSPSTAVAAQ |
| Citsi_SYT2 | (39) | LDNQNIGKITECAHYQAQLQKNLMYLAAIADIQPQ | ---------APTMPP |
| Zeama_SYT2 | (40) | LENQNLGKLAECAQYQSQLQKNLIYLAAIADIQP  | ----------QTAVSRP |
| Orysa_SYT2 | (38) | LENQNIGKLAECAQYQAQLQKNLIYLAAIADIQP  | ----------QTTISRP |
| Soltu_SYT2 | (41) | VESQNSGKISECAESQAKLQRNLMYLAAIADSQPQ | ----------PPSMHS |
| Medtr_SYT2 | (40) | LDNQNLGKLAECAQYQAQLQKNLMYLAAIADIQPQ | ----------TPALPP |
| Sorbi_SYT3 | (44) | LENQNLGKLAECAQYQAQLQKNLIYLAAIADIQPRP | ------PQNPAGRP |
| Zeama_SYT3 | (44) | LENQNLGKLAECAQYQAQLQKNLIYLAAIADIQPQP | ------PQNPAGRP |
| Bradi_SYT3 | (41) | LENQNIGKLTECAQYQAQLQKNLIYLAAIADIQP  | --------PQNPGSRP |
| Triae_SYT3 | (41) | LENQNLGKLAECAQYQAQLQKNLIYLAAIADIAQP | --------PQNPTSHP |
| Sacof_SYT3 | (42) | LENQNLGKLAECAQYQAQLQKNLIYLAAIADIQPQP | ------PQNPAGRP |
| Panvi_SYT3 | (36) | LENQNIGKLAECAQYQAQLQKNLIYLAAIADIQPQP | ------PQNPASRP |
| Orysa_SYT3 | (42) | LENQNLGKLAECAQYQAQLQKNLIYLAAIADIQP  | --------PQNPGSRP |
| Arath_SYT3 | (41) | LENQNIGKLAECAQYQALLQKNLMYLAAIADQPQ  | PPAATLTSGAMTPQA |
| Consensus | (51) | LENQNLGKLAECAQYQA LQKNLMYLAAIADAQPQ | P |

FIGURE 3 (continued)

Met-rich / QG-rich domain (continued)

```
                    101                                               150
Brana_SYT1   (81)   QYGSAGGGLIQGEGAS----HYLQQQATQQ----------------QQ
Aqufo_SYT1   (79)   QYSNAG-----IPPGA----HYLQHQDAQQ------------------
Picsi_SYT1   (81)   QIPPNA----VMQSGG----HYMQHQDAQQQ-----------------
Pinta_SYT1   (81)   QIPPNA----VMQSGG----HYMQHQDAQQQ-----------------
Poptr_SYT1   (81)   QFPSSG---IMQPGA-----HYMQHQDAQQ------------------
Vitvi_SYT1   (81)   QFPPSG---IVQPGA-----HYMQHQDAQQ------------------
Soltu_SYT1   (81)   QFSSGG----MMQPGT----HSYLQQQQQQQQ-------------AQQ
Lyces_SYT1   (81)   QFSSGG----MMQPGT----HSYLQQQQQQQQ-------------AQQ
Goshi_SYT1   (81)   QFPSGG---IMQPGG-----HYMQHQDAQQ------------------
Zeama_SYT1   (84)   QYPSN----LMMQPGP----RYMPP-QSGQ-----------------M
Medtr_SYT1   (81)   QYPSSG---MMQQGG-----HYMQAQQAQQ------------------
Citsi_SYT1   (81)   QFSSGG---IMQPGA-----HYMQHQQSQP------------------
Arath_SYT1   (81)   QYGSAGGGMIQGEGQS----HYLQQQQATQQ---------------QQ
Aspof_SYT1   (81)   QYPPNA--VAAMQSSA----RYMQQHQAAQ-----------------Q
Orysa_SYT1   (84)   QYPSN----LMMQSGA----RYMPQ-QSAQ-----------------M
Sacof_SYT1   (84)   QYPSN----LMMQPGP----RYMPP-QSGQ-----------------M
Allce_SYT2   (80)   QMMPQG---AAATPQAGNQFMQQQSPNFPPKTG-------------MQ
Lacse_SYT2   (87)   GPVPHP----GMPQQQG--FYMAQQHPQAAVMTAQP----------PS
Horvu_SYT2   (83)   QMAPPA---ASPGAG-----HYMSQVPMFPPRT--------------P
Brana_SYT2   (96)   MGAPHP----GMQPP-----SYFMQHPQASGMAQQA-PPAGIFPPRGPLQF
Sacof_SYT2   (81)   QMAPPG---ALPGVG-----QYMSQVPMFPPRT--------------P
Triae_SYT2   (83)   QMAPPS---ASPGAG-----HYMSQVPMFPPRT--------------P
Maldo_SYT2   (80)   QMAPHP---AMQQA------GYYMQHPQAAAMAQQQ----GIFSPKMPMQF
Goshi_SYT2   (81)   QMAPHP----AMQPG-----GYFMQHPQAAAMSQQP----GMYPQKVPLQF
Glyso_SYT2   (80)   QMAPHP---AMQP-------GFYMQHPQAAAAAMAQQQQQGMFPQKMPLQF
Glyma_SYT2   (80)   QMAPHP---AMQP-------GFYMQHPQAAAAMAQQQQ-GMFPQKMPLQF
Eupes_SYT2   (80)   QMSPHP---AMQQG------AYYMQHPQAAAAAMAHQSG-IFPPKMSPLQF
Arath_SYT2   (92)   MATPHS---GMQPP------SYFMQHPQAS--------PAGIFAPRGPLQF
Citsi_SYT2   (80)   QMAPHP---AMQAS------GYYMQHPQAAAMAQQQ----GIFPQKMPLQF
Zeama_SYT2   (81)   QMAPPG---GSPGVG-----QYMSQVPMFPPRT--------------P
Orysa_SYT2   (79)   QMVPHG---ASPGLGG---QYMSQVPMFPPRT--------------P
Soltu_SYT2   (82)   QLASGG----MMQGGA----HYMQQQQ-----------------AQQ
Medtr_SYT2   (81)   QMAPHP---AMQQ-------GFYMQHPQAAAMAQQQ----GMFPQKMPMQF
Sorbi_SYT3   (88)   QMMQPG---IVPGAG-----HYMSQVPMFPPRT--------------P
Zeama_SYT3   (88)   QMMQPG---IVPGAG-----HYMSQVPMFPPRT--------------P
Bradi_SYT3   (83)   QMVQPG---GMPGAG-----HYMSQVPMFPPRT--------------P
Triae_SYT3   (83)   QMVQPG---SMQGAG-----HYMSQVPMFPPRT--------------P
Sacof_SYT3   (86)   QMMQPG---IVPGAG-----HYMSQVPMFPPRT--------------P
Panvi_SYT3   (80)   QMMQPG---MVPGAG-----HYMSQVPMFPPRT--------------P
Orysa_SYT3   (84)   QMMQPG---ATPGAG-----HYMSQVPMFPPRT--------------P
Arath_SYT3   (91)   MAPNPS---SMQPPP-----SYFMQQHQAVG-MAQQ-IPPGIFPPRGPLQF
Consensus    (101)  QM   G    M  G       YYMQ PQA
```

FIGURE 3 (continued)

Met-rich / QG-rich domain (continued)

```
                      151                                                          200
Brana_SYT1  (110)  MTQQSLMAAR---SSMMYQQQQQ---------PYATLQHQQ-----LHHSQ
Aqufo_SYT1  (100)  MTQQSLMAAR---SNMLYAQPITG----------MQQ-QQ-----AMHSQ
Picsi_SYT1  (104)  VTPQSLMAAR---SSMLYSQQPMAALHQAQQQQQQQHQQQQQ---SLHSQ
Pinta_SYT1  (104)  VTPQSLMAAR---SSILYAQQ----QQQQQHQQHQQQQQQQ---SLHSQ
Poptr_SYT1  (103)  MTPQALMAAR---SSMLQYAQQP---------FSALQQQQ-----ALHSQ
Vitvi_SYT1  (103)  MTPQSLLAAR---SSML-YTQQP---------FSALQQQQ-----AIHSQ
Soltu_SYT1  (108)  MATQQLMAAR--SSSMLYGQQQQQ----Q--QQSQLSQFQQG---LHSSQ
Lyces_SYT1  (108)  MATQQLMAAR--SSSMLYGQQQ----------QQSQLSQYQQG---LHSSQ
Goshi_SYT1  (104)  MTQQSLMAAR---SSML-YSQQP---------FSALQQQQQ---ALHSQ
Zeama_SYT1  (106)  MNPQSLMAAR---SSMMYAHPS----------LSPLQQQ-----AAHGQ
Medtr_SYT1  (103)  MTQQQLMAAR---SSLM-YAQQ-----------LQQQ-----ALQSQ
Citsi_SYT1  (103)  MTPQSLMAAR---SSMV-YSQQQ---------FSVLQQQ-----ALHGQ
Arath_SYT1  (110)  MTQQSLMAAR---SSMLYAQQQQQ----QQ-PYATLQHQQ-----LHHSQ
Aspof_SYT1  (106)  MTPQSLMAAR---SSMLYSQSP----------MSALQQQQQ---AAMHSQ
Orysa_SYT1  (106)  MAPQSLMAAR---SSMMYAQPA----------LSPLQQQQQQQAAAAHGQ
Sacof_SYT1  (106)  MSPQSLMAAR---SSMMYAHPS----------MSPLQQQQ-----AAHGQ
Allce_SYT2  (112)  FTPQQVQELQ-----------QQQ--------LQHQPHMM----PPFQGQ
Lacse_SYT2  (119)  GFPQPMPGMQ----------FNS---------------P-----QAIQGQ
Horvu_SYT2  (109)  LTPQQMQEQQ----------LQQ---------QQAQM-----LPFAGQ
Brana_SYT2  (137)  GSPHQLQDPQ----------QQ----------HMQ------QAMQGH
Sacof_SYT2  (107)  LTPQQMQEQQ----------LQQ---------QQAQL-----LNFSGL
Triae_SYT2  (109)  LTPQQMQEQQ----------LQQ---------QQAQM-----LPFAGQ
Maldo_SYT2  (118)  NNMHQMHDP-----------------------QQHQ------QAMQGQ
Goshi_SYT2  (119)  NSPHQMQDPQ--------HLLY----------QQHQ------QAMQGQ
Glyso_SYT2  (121)  GNPHQMQEQQ----------QQ----------LHQ-------QAIQGQ
Glyma_SYT2  (120)  GNPHQMQEQQ----------QQ----------LHQ-------QAIQGQ
Eupes_SYT2  (121)  NNPHQIQDPQ----------------------QLHQ------AALQGQ
Arath_SYT2  (126)  GSPLQFQDPQ----------QQQ---------QIHQ------QAMQGH
Citsi_SYT2  (118)  NNPHQLQDPQ----------QQLH--------QH--------QAMQAQ
Zeama_SYT2  (107)  LTPQQMQEQQ----------LQQ---------QQAQL-----LNFSGQ
Orysa_SYT2  (106)  LTPQQMQEQQ----------LQQ---------QQAQL-----LSFGGQ
Soltu_SYT2  (104)  LTTQSLMAAARSSSSMLYGQQQQQ----QQQQLSSLQQQQAA---FHSQQ
Medtr_SYT2  (118)  GNPHQMGDQQ----------HQQQQ-------QQLHQ-----QAMQGQ
Sorbi_SYT3  (114)  LTPQQMQEQQ----------QQQ---------LQQQQAQA----LAFPGQ
Zeama_SYT3  (114)  LTPQQMQEQQ----------QQQQF-------QQQQQQVQA---LTFPGQ
Bradi_SYT3  (109)  LTPQQMQEQQ----------HQQ---------LQQQQAQA----LAFPSQ
Triae_SYT3  (109)  LTPQQMQEQQ----------HQQ---------LQQQQAQA----LSFPAQ
Sacof_SYT3  (112)  LTPQQMQEQQ----------------------LQQQQAQA----LTFPGQ
Panvi_SYT3  (106)  LTPQQMQEQQ----------QQQ---------QLQQQQAQA---LAFPGQ
Orysa_SYT3  (110)  LTPQQMQEQQ----------QQQ---------LQQQQAQA----LAFPGQ
Arath_SYT3  (132)  GSEHQFLDPQ----------QQ----------LHQ-------QAMQGH
Consensus   (151)  MTPQQLQE Q           QQQ              Q QQ      A  GQ
```

FIGURE 3 (continued)

Met-rich / QG-rich domain (continued)

```
                    201                                                    250
Brana_SYT1  (144)   LGMSSSS-GGG--------SSGLHILQG----EAG--------GFHEFGRG-
Aqufo_SYT1  (131)   LGMSS-----GG--------NSGLHMMHNEG---S--------MGGSGALGS
Picsi_SYT1  (148)   LGINS-----GG--------SSGLHMLHGETN-MG--------CNGPLSSGG
Pinta_SYT1  (144)   LGINS-----GG--------SSGLHMLHGETN-MG--------CNGPLSSGG
Poptr_SYT1  (136)   LGMSS-----GG--------SAGLHMMQSEANTAG--------GSGALGAGR
Vitvi_SYT1  (135)   LGMGS-----GG--------SAGLHMLQSEGSNPG--------GNGTLGTGG
Soltu_SYT1  (147)   LGMSSG--SGGS--------TGLHHMLQSE-------------SSPHGGGF
Lyces_SYT1  (144)   LGMSSG--SGGS--------TGLHHMLQSE-------------SSPHGGGF
Goshi_SYT1  (138)   LGMSS-----GG--------STGLHMLQTESSTAG--------GSGALGAGG
Zeama_SYT1  (138)   LGMAPGGGGGGT--------TSGFSILHGEASMGGGGAGAGAGNNMMNAGM
Medtr_SYT1  (131)   LGMNS-----SG--------SQGLHMLHSEGANVG--------GNSSLGAG-
Citsi_SYT1  (135)   LGMSS-----GG--------SSGLHMLQSEGSTAG--------GSGSLGGGG
Arath_SYT1  (147)   LGMSSSG-GGGG--------SSGLHILQG----EAG--------GFHDFGRG-
Aspof_SYT1  (141)   LAMSSGGNNS-S--------TGGFTILHGEASIGG--------NGSMNSGGV
Orysa_SYT1  (143)   LGMGSGG----T--------TSGFSILHGEASMGGGGGGGGAGNSMMNAGV
Sacof_SYT1  (138)   LGMASGGGGG-T--------TSGFNILHGEASMGG-AGGACAGNNMMNAGM
Allce_SYT2  (139)   MGMRP--MNGMQ------------AAMHADSSLAY-------NTNNKQDAG-
Lacse_SYT2  (139)   MGGRSGGPPSS--------------AASDVWRG-------SMQDGG----
Horvu_SYT2  (133)   MVARPGAVNGIP-----------QAPQVEQP-------------------
Brana_SYT2  (159)   MGMRPMGINNNN-----------GMQHQMQQQQP-------ETSLGGS---
Sacof_SYT2  (131)   MVARPGMVNGMP-----------QSIQVQQAQ----------PPPAGN--
Triae_SYT2  (133)   MVARPGAVNGMP-----------QAPQVEP--------------------
Maldo_SYT2  (137)   MGMRPGGPNGMP-----------SMLHTEATHGG-------GS-GGPNSAG
Goshi_SYT2  (143)   MGIRPGGPNNSM-----------HPMHSEASLGG-------GSSGGPPQPS
Glyso_SYT2  (142)   MGLRPGGINNGM-----------HPMHNE----G-------GNSGGPPSAT
Glyma_SYT2  (141)   MGLRPGDINNGM-----------HPMHSEAALGG-------GNSGGPPSAT
Eupes_SYT2  (141)   MGMRPGMPNNGM-----------HPMHPEANLGG-------SN--------
Arath_SYT2  (149)   MGIRPMGMTNN------------GMQHAMQQ--P-------ETGLGG----
Citsi_SYT2  (140)   MGMRPGATNNGM-----------HPMHAESSLGG-------GSSGGPPSAS
Zeama_SYT2  (131)   MVARPGMVNGMA-----------QSMQAQLP-------------P-GVN--
Orysa_SYT2  (130)   MVMRPGVVNGIP-----------QILQGEMHRG--------------AD-
Soltu_SYT2  (147)   LGMSSS--GGGS--------SSGLHMLQSEN--T-------HSASTGGGG
Medtr_SYT2  (144)   MGLRPGGINNGM-----------HPMHNEAALGG-------SGSGGQMTGV
Sorbi_SYT3  (141)   MVMRPATINGMQQ--PMQADPAR-AAELQQPASV-------PADGRVSK--
Zeama_SYT3  (144)   MVMRPGTINGMQQQQPMQADPARAAAELQQAAPI-------PADGRGSK--
Bradi_SYT3  (136)   MVMRPGTVNGMQP--------MQADLQAAAAAPG-------LADSRGSKQ-
Triae_SYT3  (136)   VVMRPGTVNGMQ-----------QPMQAAGDLQP-------AAAPGGSKQ-
Sacof_SYT3  (139)   MVMRPATINGIQQ--PMQADPAR-AAELQQPPAG-------PADGRVSKQ-
Panvi_SYT3  (135)   MVMRP-TINGMQP--MQADPAAAASLQQSAPG--------PTDGRGGK--
Orysa_SYT3  (137)   MLMRPGTVNGMQS--IPVADPAR-AADLQTAAPG-------SVDGRGNE--
Arath_SYT3  (153)   MGIRPMGLNNNN-----------GIQHQMHHHET-------ALAANNA---
Consensus   (201)   MGMRPG NG           ML   E   G                  G
```

FIGURE 3 (continued)

Met-rich / QG-rich domain (continued)

```
                    251                                                      300
Brana_SYT1  (174)   KPEMGSG----------------------------------EGRGGSS
Aqufo_SYT1  (159)   YSDYGRG----SGGG----------VTIASKQDGGS-----GSGEGRGGNS
Picsi_SYT1  (178)   FPEFGRGSATSAEGMQANRGFTIDRGSNKQDGVGSENAHPGAGDGRGSST
Pinta_SYT1  (174)   FPEFGRGSATSADGMQVNRGFAIDRGSNKQDGVGSENAHAGADGRGSST
Poptr_SYT1  (167)   FPDFGMD----ASS--------RGIASGSKQDIRSA-----GSSEGRGGSS
Vitvi_SYT1  (166)   FPDFSFG----TSGEGLQAAGRGMAGGSK---QDM-----GNAEGRGGNS
Soltu_SYT1  (175)   SHDFGR-------------------ANKQDIGSS-----MSAEGRGGSS
Lyces_SYT1  (172)   SHDFGR-------------------ANKQDIGSS-----MSAEGRGGSS
Goshi_SYT1  (169)   FPDFGRG----SSGEGIHGG-RPMAGGSKQDIGSA-----GSAEGRGGSS
Zeama_SYT1  (181)   FSGFGRS----GSG------------------AKEG--STSLSVDVRG
Medtr_SYT1  (161)   FPDFGRS----SAGDGLHG-----SGKQ-----DI-----GSTDGRGGSS
Citsi_SYT1  (166)   FPDFGRG----SSGEGLHS----RGMGSKHDIGSS-----GSAEGRGGSS
Arath_SYT1  (178)   KPEMGSG----GGG----------------------------EGRGGSS
Aspof_SYT1  (176)   FGDFGRS----SGG--------------------------KQETG
Orysa_SYT1  (182)   FSDFGRG----GGG-----------------GKEG--STSLSVDVRG
Sacof_SYT1  (179)   FSGFGRS----GSG------------------AKEG--STSLSVDVRG
Allce_SYT2  (169)   --NAAYE-----NTA-------------------------ANTDGSIQKK
Lacse_SYT2  (164)   ------G-----GAA-------------------------ADGGKDGHAG
Horvu_SYT2  (153)   --AYAAG-----GAS-------------------------SEPSGTESHR
Brana_SYT2  (189)   AANVGLR-----GGK-----------------------------QDG
Sacof_SYT2  (158)   --KQDAG-----GVA-------------------------SEPSGIENHR
Triae_SYT2  (152)   --AYAAG-----GAS-------------------------SEPSGTESHR
Maldo_SYT2  (169)   DPNDGRG-----GSK-------------------------QDASESGAGG
Goshi_SYT2  (176)   GPSDGRA-----GNK-------------------------QEGSEAGGN-
Glyso_SYT2  (171)   GPNDARG-----GSK-------------------------QDASEAGTAG
Glyma_SYT2  (174)   GPNDARG-----GSK-------------------------QDASEAGTAG
Eupes_SYT2  (166)   ---DGRG-----GNK-------------------------QDAPETGASG
Arath_SYT2  (175)   --NVGLR-----GGK-----------------------------QDG
Citsi_SYT2  (173)   GPGDIRG-----GNK-------------------------QDASEAGTTG
Zeama_SYT2  (155)   --KQDAG-----GVA-------------------------SEPSGTESHR
Orysa_SYT2  (154)   --HQNAG-----GAT-------------------------SEPS--ESHR
Soltu_SYT2  (178)   FPDFGRG----LGS-----------GNKHEMGSS-----MSDQGRGGSS
Medtr_SYT2  (177)   VVEQAR-----------------------------------CFGAGTAG
Sorbi_SYT3  (180)   --QDTAA-----GVS-------------------------SEPSANESHK
Zeama_SYT3  (186)   --QDTAG-----GAS-------------------------SEPSANESHK
Bradi_SYT3  (171)   --DAAVA-----GAI-------------------------SEPSGTESHK
Triae_SYT3  (168)   --DAAVA-----GAS-------------------------SEPSGTKSHK
Sacof_SYT3  (179)   --QDTTA-----GVS-------------------------SEPSANESHK
Panvi_SYT3  (173)   --QDATA-----GVS-------------------------TEPSGTESHK
Orysa_SYT3  (176)   ------Q-----DAT-------------------------SEPSGTESHK
Arath_SYT3  (183)   GPNDASG-----GGK-------------------------PDGTNMSQSG
Consensus   (251)         GRG       G                                  G  G
```

FIGURE 3 (continued)

Met-rich / QG-rich domain
(continued)

```
                        301                      324
Brana_SYT1    (188)    G------DGGETLYLKS--SDDGN-
Aqufo_SYT1    (191)    GGQS-ADGGESLYLKN--SDEGN-
Picsi_SYT1    (228)    GGQN-ADESEPSYLKA--SEE---
Pinta_SYT1    (224)    GGQN-ADESEPSYLKA--SEEEGN
Poptr_SYT1    (201)    GGQGG-DGGETLYLKS--ADDGN-
Vitvi_SYT1    (204)    GGQGG-DGGETLYLKA--AEDGN-
Soltu_SYT1    (200)    ---GG-DGGENLYLKA--SED---
Lyces_SYT1    (197)    ---G---G-ENLYLKA--SED---
Goshi_SYT1    (209)    GGQGGGDGGETLYLKA--ADDGN-
Zeama_SYT1    (205)    GTSSGAQSGDGEYLKVGTEEEGS-
Medtr_SYT1    (192)    SGHSG-DGGETLYLKS--SGDGN-
Citsi_SYT1    (203)    GSQ---DGGETLYLKG--ADDGN-
Arath_SYT1    (195)    G------DGGETLYLKS--SDDGN-
Aspof_SYT1    (191)    --SEGHGTETPMYLKG-SEEEGN-
Orysa_SYT1    (207)    -ANSGAQSGDGEYLKG-TEEEGS-
Sacof_SYT1    (203)    GTSSGAQSGDGEYLKAGTEEEGS-
Allce_SYT2    (187)    TANDDLDPSAANPRRSEDAKSS--
Lacse_SYT2    (178)    G---------------GPEEAK-
Horvu_SYT2    (171)    S------TGADNDGGSGLADQS--
Brana_SYT2    (202)    ADGQG-----------KDDGK-
Sacof_SYT2    (176)    S------TGDNDGGSD--------
Triae_SYT2    (170)    S------TGADNDGGSGWADQS--
Maldo_SYT2    (189)    -DGQG--TSAGGRGTG-DGEDGK-
Goshi_SYT2    (195)    --GQG--STTGGHGGGDGADEAK-
Glyso_SYT2    (191)    GDGQG--SSAAAHNSGDG-EEAK-
Glyma_SYT2    (194)    GDGQG--SSAAAHNSGDG-EEAK-
Eupes_SYT2    (183)    GDGQG------NSGGDGAEDGK-
Arath_SYT2    (186)    ADGQG-----------KDDGK-
Citsi_SYT2    (193)    ADGQG--SSAGGHGG--DGEEAK-
Zeama_SYT2    (173)    S------TGGD-DGGSD--------
Orysa_SYT2    (170)    S----TGTENDGGSDFGDQS--
Soltu_SYT2    (207)    SGHGG-DGGENLYLKS--SEDGN-
Medtr_SYT2    (191)    GDGQGT-SAAAAHNSGDASEEGK-
Sorbi_SYT3    (198)    TT-----TGADSEAGGDVAEKS--
Zeama_SYT3    (204)    SA-----TGADTEAGGDVAEKS--
Bradi_SYT3    (189)    S------TGADHEAGGDVAEQS--
Triae_SYT3    (186)    N------AGAEEVG-ADVAEQS--
Sacof_SYT3    (197)    TT-----TGADSEAGGDVAEKS--
Panvi_SYT3    (191)    ST-----TAADHDVGTDVAEKS--
Orysa_SYT3    (190)    S------AGADNDAGGDIAEKS--
Arath_SYT3    (203)    ADGQGG-S-AARHGGGDAKTEGK-
Consensus     (301)           TG     Y  G    AEDG
```

FIGURE 3 (continued)

SEQ ID NO : 01 SNH domain from SYT-like polypeptides

IQ(Q/K)XL(D/E)(E/D)N(K/N)XLIX(C/A/K)I(L/V/M)(E/D/S)(S/N)(Q/L)N
XG(K/R)XXEC(A/E/S)XXQ(A/S/Q)XL(Q/H)XNL(M/L/V)YLA(A/T)IAD

Where X is any amino acid

**SEQ ID NO : 02 *Arabidopsis thaliana* AtSYT1 SNH domain**

IQQYLDENKSLILKIVESQNSGKLSECAENQARLQRNLMYLAAIAD

**SEQ ID NO : 03 *Arabidopsis thaliana* AtSYT1 cDNA (AY102639)**

ATGCAACAGCACCTGATGCAGATGCAGCCCATGATGGCTGGTTACTACCCCAGCAATGTTAC
CTCTGATCATATCCAACAGTACTTGGACGAAAACAAATCGTTGATTCTGAAGATTGTTGAGT
CTCAAAACTCTGGAAAGCTTAGCGAATGCGCCGAGAATCAAGCAAGGCTTCAACGCAACCTA
ATGTACCTAGCTGCAATAGCAGATTCTCAGCCTCAGCCACCAAGTGTGCATAGCCAGTATGG
ATCTGCTGGTGGTGGGATGATTCAGGGAGAAGGAGGGTCACACTATTTGCAGCAGCAACAAG
CGACTCAACAGCAACAGATGACTCAGCAGTCTCTAATGGCGGCTCGATCTTCAATGTTGTAT
GCTCAGCAACAGCAGCAGCAGCCTTACGCGACGCTTCAGCATCAGCAATTGCACCATAG
CCAGCTTGGAATGAGCTCGAGCAGCGGAGGAGGAGGAAGCAGTGGTCTCCATATCCTTCAGG
GAGAGGCTGGTGGGTTTCATGATTTTGGCCGTGGGAAGCCGGAAATGGGAAGTGGTGGTGGC
GGTGAAGGCAGAGGAGGAAGTTCAGGGGATGGTGGAGAAACCCTTTACTTGAAATCATCAGA
TGATGGGAATTGA

**SEQ ID NO : 04 *Arabidopsis thaliana* AtSYT1 protein**

MQQHLMQMQPMMAGYYPSNVTSDHIQQYLDENKSLILKIVESQNSGKLSECAENQARLQRNL
MYLAAIADSQPQPPSVHSQYGSAGGGMIQGEGGSHYLQQQQATQQQQMTQQSLMAARSSMLY
AQQQQQQQPYATLQHQQLHHSQLGMSSSSGGGGSSGLHILQGEAGGFHDFGRGKPEMGSGGG
GEGRGGSSGDGGETLYLKSSDDGN

**SEQ ID NO : 05 *Arabidopsis thaliana* AtSYT2 cDNA (AY102640)**

ATGCAGCAGCAGCAGTCTCCGCAAATGTTTCCGATGGTTCCGTCGATTCCCCCTGCTAACAA
CATCACTACCGAACAGATCCAAAAGTACCTTGATGAGAACAAGAAGCTGATTATGGCCATCA
TGGAAAACCAGAATCTCGGTAAACTTGCTGAGTGCGCCCAGTACCAAGCTCTTCTCCAGAAG
AACTTGATGTATCTTGCTGCAATTGCTGATGCTCAACCCCCACCACCTACGCCAGGACCTTC
ACCATCTACAGCTGTCGCTGCCCAGATGGCAACACCGCATTCTGGGATGCAACCACCTAGCT
ACTTCATGCAACACCCACAAGCATCCCCTGCAGGGATTTTCGCTCCAAGGGGTCCTTTACAG
TTTGGTAGCCCACTCCAGTTTCAGGATCCGCAACAGCAGCAGCAGATACATCAGCAAGCTAT
GCAAGGACACATGGGGATTAGACCAATGGGTATGACCAACAACGGGATGCAGCATGCGATGC
AACAACCAGAAACCGGTCTTGGAGGAAACGTGGGGCTTAGAGGAGGAAAGCAAGATGGAGCA
GATGGACAAGGAAAAGATGATGGCAAGTGA

FIGURE 8

SEQ ID NO : 06 *Arabidopsis thaliana* AtSYT2 protein

MQQQQSPQMFPMVPSIPPANNITTEQIQKYLDENKKLIMAIMENQNLGKLAECAQYQALLQK
NLMYLAAIADAQPPPPTPGPSPSTAVAAQMATPHSGMQPPSYFMQHPQASPAGIFAPRGPLQ
FGSPLQFQDPQQQQQIHQQAMQGHMGIRPMGMTNNGMQHAMQQPETGLGGNVGLRGGKQDGA
DGQGKDDGK

SEQ ID NO : 07 *Arabidopsis thaliana* AtSYT3 cDNA (AY102641)

ATGCAGCAATCTCCACAGATGATTCCGATGGTTCTTCCTTCATTTCCGCCCACCAATAATAT
CACCACCGAACAGATCCAAAAGTATCTTGATGAGAACAAGAAGCTGATAATGGCGATCTTGG
AAAATCAGAACCTCGGTAAACTTGCAGAATGTGCTCAGTATCAAGCTCTTCTCCAGAAGAAT
TTGATGTATCTCGCTGCAATTGCGGATGCTCAACCTCAGCCACCAGCAGCTACACTAACATC
AGGAGCCATGACTCCCCAAGCAATGGCTCCTAATCCGTCATCAATGCAGCCACCACCAAGCT
ACTTCATGCAGCAACATCAAGCTGTGGGAATGGCTCAACAAATACCTCCTGGGATTTTCCCT
CCTAGAGGTCCATTGCAATTTGGTAGCCCGCATCAGTTTCTGGATCCGCAGCAACAGTTACA
TCAACAAGCTATGCAAGGGCACATGGGGATTAGACCAATGGGTTTGAATAATAACAACGGAC
TGCAACATCAAATGCACCACCATGAAACTGCTCTTGCCGCAAACAATGCGGGTCCTAACGAT
GCTAGTGGAGGAGGTAAACCGGATGGGACCAATATGAGCCAGAGTGGAGCTGATGGGCAAGG
TGGCTCAGCCGCTAGACATGGCGGTGGTGATGCAAAAACTGAAGGAAAATGA

SEQ ID NO : 08 *Arabidopsis thaliana* AtSYT3 protein

MQQSPQMIPMVLPSFPPTNNITTEQIQKYLDENKKLIMAILENQNLGKLAECAQYQALLQKN
LMYLAAIADAQPQPPAATLTSGAMTPQAMAPNPSSMQPPPSYFMQQHQAVGMAQQIPPGIFP
PRGPLQFGSPHQFLDPQQQLHQQAMQGHMGIRPMGLNNNNGLQHQMHHHETALAANNAGPND
ASGGGKPDGTNMSQSGADGQGGSAARHGGGDAKTEGK

SEQ ID NO : 09 *Aspergillus officinalis* SYT cDNA (CV287542)

ATGCAGCAGCACCTGATGCAGATGCAGCCCATGATGGCAACCTACGGTTCACCGAATCAGGT
CACCACCGATATCATTCAGCAGTATCTGGACGAGAACAAGCAGTTGATTCTGGCTATTCTTG
AAAACCAAAATTCAGGAAAAGCTGATGAATGTGCTGAGAATCAGGCTAAGCTTCAGAGGAAT
CTGATGTATCTTGCAGCCATTGCGGATAGCCAGCCCCAAGTTCCTACCATTGCTCAGTATCC
TCCCAACGCTGTTGCTGCTATGCAATCGAGTGCTCGCTACATGCAACAACACCAAGCAGCTC
AACAGATGACCCCTCAATCTCTCATGGCTGCTCGCTCCTCAATGCTCTACTCACAGTCCCCA
ATGTCTGCACTCCAGCAGCAACAGCAGCAAGCAGCAATGCATAGCCAGCTCGCCATGAGCTC
CGGAGGCAACAACAGCAGCACCGGAGGATTCACCATTCTTCATGGTGAAGCTAGCATAGGAG
GCAATGGCTCAATGAATTCTGGTGGAGTCTTTGGAGATTTTGGACGGAGCAGCGGTGGGAAG
CAAGAGACTGGGAGCGAAGGGCACGGGACAGAGACTCCTATGTACCTGAAAGGCTCTGAAGA
AGAAGGAAACTGA

FIGURE 8 (continued)

SEQ ID NO : 10 *Aspergillus officinalis* SYT protein

MQQHLMQMQPMMATYGSPNQVTTDIIQQYLDENKQLILAILENQNSGKADECAENQAKLQRN
LMYLAAIADSQPQVPTIAQYPPNAVAAMQSSARYMQQHQAAQQMTPQSLMAARSSMLYSQSP
MSALQQQQQQAAMHSQLAMSSGGNNSSTGGFTILHGEASIGGNGSMNSGGVFGDFGRSSGGK
QETGSEGHGTETPMYLKGSEEEGN

SEQ ID NO : 11 *Brassica napus* SYT cDNA (CD823592)

ATGCAGCCCATGATGGCTGGTTACTACCCCAGCAATGTCACCTCTGATCATATCCAGCAGTA
CTTGGATGAGAACAAGTCTTTGATTCTGAAGATAGTTGAGTCTCAAAACTCAGGAAAGCTCA
GCGAGTGTGCCGAGAATCAGGCAAGGCTTCAACGCAACCTCATGTACTTGGCTGCAATAGCA
GATTCTCAGCCTCAACCTCCAAGCGTGCATAGCCAGTATGGATCTGCTGGTGGTGGGTTGAT
TCAGGGAGAAGGAGCGTCACACTATTTGCAGCAGCAACAGGCGACTCAACAGCAGCAGATGA
CTCAGCAGTCTCTTATGGCAGCTCGTTCTTCAATGATGTATCAGCAGCAGCAACAGCCTTAT
GCAACGCTTCAGCATCAGCAGTTGCACCATAGCCAGCTTGGGATGAGCTCTAGCAGCGGAGG
AGGAAGCAGTGGTCTCCATATCCTTCAGGGAGAGGCTGGTGGGTTTCATGAATTTGGCCGTG
GGAAGCCGGAGATGGGAAGTGGTGAAGGCAGGGGTGGAAGCTCAGGGGATGGTGGAGAAACA
CTCTACTTGAAGTCATCAGATGATGGGAACTGA

SEQ ID NO : 12 *Brassica napus* SYT protein
MQQHLMQMQPMMAGYYPSNVTSDHIQQYLDENKSLILKIVESQNSGKLSECAENQARLQRNL
MYLAAIADSQPQPPSVHSQYGSAGGGLIQGEGASHYLQQQQATQQQQMTQQSLMAARSSMMY
QQQQQPYATLQHQQLHHSQLGMSSSSGGGSSGLHILQGEAGGFHEFGRGKPEMGSGEGRGGS
SGDGGETLYLKSSDDGN

SEQ ID NO : 13 *Citrus sinensis* SYT cDNA (CB290588)

ATGCAACAGCACCTGATGCAGATGCAGCCCATGATGGCAGCTTATTATCCCAACAACGTCAC
TACTGACCACATTCAACAGTATCTAGATGAGAACAAATCATTGATTTTGAAGATTGTTGAGA
GCCAGAATTCAGGGAAACTGAGCGAGTGTGCAGAGAACCAGGCAAGATTGCAGCGGAATCTC
ATGTACCTGGCTGCTATTGCTGATGCTCAACCCCAACCACCTAGCGTTCATGCCCAGTTCTC
TTCTGGTGGCATTATGCAGCCAGGAGCTCACTATATGCAACACCAGCAATCTCAGCCAATGA
CACCACAGTCACTTATGGCTGCACGCTCATCCATGGTGTACTCTCAACAGCAATTTCAGTG
CTTCAGCAACAGCAAGCCTTGCATGGTCAGCTTGGCATGAGCTCTGGTGGTAGCTCAGGACT
TCACATGCTGCAAAGTGAGGGTAGTACTGCAGGAGGTAGTGGTTCACTTGGGGGTGGGGGAT
TCCCTGATTTTGGCCGTGGCTCATCTGGTGAAGGCTTGCACTCAAGGGGAATGGGGAGCAAG
CATGATATAGGCAGTTCTGGATCTGCTGAAGGACGAGGAGGGAGCTCAGGAAGCCAAGATGG
AGGCGAAACTCTCTACTTGAAAGGGGCTGATGATGGAAATTAA

SEQ ID NO : 14 *Citrus sinensis* SYT protein

MQQHLMQMQPMMAAYYPNNVTTDHIQQYLDENKSLILKIVESQNSGKLSECAENQARLQRNL
MYLAAIADAQPQPPSVHAQFSSGGIMQPGAHYMQHQQSQPMTPQSLMAARSSMVYSQQQFSV
LQQQQALHGQLGMSSGGSSGLHMLQSEGSTAGGSGSLGGGGFPDFGRGSSGEGLHSRGMGSK
HDIGSSGSAEGRGGSSGSQDGGETLYLKGADDG

FIGURE 8 (continued)

SEQ ID NO : 15 *Gossypium arboreum* SYT cDNA (BM359324)

ATGCAGCAGCACCTGATGCAGATGCAGCCCATGATGGCAGCTTATTATCCCAACAACGTCAC
TACTGATCATATTCAACAGTATCTCGATGAGAACAAGTCATTGATCTTAAAGATTGTTGAGA
GCCAGAATTCTGGGAAATTGAGTGAATGTGCTGAGAACCAAGCAAGGCTGCAGCGAAACCTC
ATGTACCTGGCTGCCATTGCGGATTCTCAACCCCAACCACCCACCGTGCATGCACAGTTTCC
ATCTGGTGGTATCATGCAGCAAGGAGCTGGGCACTACATGCAGCACCAACAAGCTCAACANA
TGACACAACAGTCGCTTATGGCTGCTCGGTCCTCAATGTTGTATTCTCAGCAACCATTTTCT
GCACTGCAACAACAACAACAACAAGGCTTTGCACAGTCAGCTTGGCATGAGCTCTGGCGGGA
GCACAGGCCTTTCATATGCTGCAAACTGAATCTAGTACTGCAGGGGGCAGTGAGACACCTTG
GGCCCGAGGGTTGTCCTGATTTGGACGGGGGTCTTTTGGAGAGGCATCCCTGGTGGCAGGCC
AATGGCCGGGGGAACAACCAAAAATCCGGGGAGGCCGGCTCACCTAAGGGCCGGGAGGAGCC
CTTGGGGCAGGGGGGGGTGATGGGGGGAACCTCTTCTTAA

SEQ ID NO : 16 *Gossypium arboreum* SYT protein

MQQHLMQMQPMMAAYYPNNVTTDHIQQYLDENKSLILKIVESQNSGKLSECAENQARLQRNL
MYLAAIADSQPQPPTVHAQFPSGGIMQQGAGHYMQHQQAQXMTQQSLMAARSSMLYSQQPFS
ALQQQQQQGFAQSAWHELWREHRPFICCKLNLVLQGAVRHLGPEGCPDLDGGLLERHPWWQA
NGRGNNQKSGEAGSPKGREEPLGQGGVMGGTSS

SEQ ID NO : 17 *Medicago trunculata* SYT cDNA (CA858507)

ATGCAGCAGCACCTGATGCAGATGCAGCCCATGATGGCAGCTTACTATCCTAACAACGTCAC
TACTGATCATATTCAACAGTATCTTGATGAGAACAAGTCCTTGATTCTCAAGATTGTTGAAA
GCCAGAACACTGGCAAGCTCACCGAGTGTGCTGAGAACCAATCAAGGCTTCAGAGAAATCTC
ATGTACCTAGCTGCAATAGCTGATTCTCAACCCCAACCACCTACTATGCCTGGCCAGTACCC
TTCAAGTGGAATGATGCAGCAGGGAGGACACTACATGCAGGCTCAACAAGCTCAGCAGATGA
CACAACAACAATTAATGGCTGCACGTTCCTCTCTTATGTATGCTCAACAGCTTCAACAGCAG
CAAGCCTTGCAAAGCCAACTTGGTATGAATTCCAGTGGAAGTCAAGGCCTTCACATGTTGCA
TAGTGAAGGGGCTAATGTTGGAGGCAATTCATCTCTAGGGGCTGGTTTTCCTGATTTTGGCC
GTAGCTCAGCCGGTGATGGTTTGCACGGCAGTGGTAAGCAAGACATTGGAAGCACTGATGGC
CGCGGTGGAAGCTCTAGTGGTCACTCTGGTGATGGCGGCGAAACACTTTACCTGAAATCTTC
TGGTGATGGGAATTAG

SEQ ID NO : 18 *Medicago trunculata* SYT protein

MQQHLMQMQPMMAAYYPNNVTTDHIQQYLDENKSLILKIVESQNTGKLTECAENQSRLQRNL
MYLAAIADSQPQPPTMPGQYPSSGMMQQGGHYMQAQQAQQMTQQQLMAARSSLMYAQQLQQQ
QALQSQLGMNSSGSQGLHMLHSEGANVGGNSSLGAGFPDFGRSSAGDGLHGSKQDIGSTDG
RGGSSSGHSGDGGETLYLKSSGDGN

FIGURE 8 (continued)

**SEQ ID NO : 19 *Oryza sativa* SYT1 cDNA (AK058575)**

ATGCAGCAGCAACACCTGATGCAGATGAACCAGGGCATGATGGGGGGATATGCTTCCCCTAC
CACCGTCACCACTGATCTCATTCAGCAGTATCTGGATGAGAACAAGCAGCTGATCCTGGCCA
TCCTTGACAACCAGAACAATGGGAAGGTGGAAGAGTGCGCTCGGAACCAAGCTAAGCTCCAG
CACAATCTCATGTACCTCGCCGCCATCGCCGACAGCCAGCCGCCGCAGACGGCCGCCATGTC
CCAGTATCCGTCGAACCTGATGATGCAGTCCGGGGCGAGGTACATGCCGCAGCAGTCGGCGC
AGATGATGGCGCCGCAGTCGCTGATGGCGGCGAGGTCTTCGATGATGTACGCGCAGCCGGCG
CTGTCGCCGCTCCAGCAGCAGCAGCAGCAGGCGGCGGCGGCGCACGGGCAGCTGGGCAT
GGGCTCGGGGGGCACCACCAGCGGGTTCAGCATCCTCCACGGCGAGGCCAGCATGGGCGGCG
GCGGCGGCGGTGGCGCCGGTAACAGCATGATGAACGCCGGCGTGTTCTCCGACTTCGGA
CGCGGCGGCGGCGGCGGCAAGGAGGGGTCCACCTCGCTGTCCGTCGACGTCCGGGGCGC
CAACTCCGGCGCCCAGAGCGGCGACGGGGAGTACCTCAAGGGCACCGAGGAGGAAGGCAGCT
AG

**SEQ ID NO : 20 *Oryza sativa* SYT1 protein**

MQQQHLMQMNQGMMGGYASPTTVTTDLIQQYLDENKQLILAILDNQNNGKVEECARNQAKLQ
HNLMYLAAIADSQPPQTAAMSQYPSNLMMQSGARYMPQQSAQMMAPQSLMAARSSMMYAQPA
LSPLQQQQQQQAAAAHGQLGMGSGGTTSGFSILHGEASMGGGGGGGAGNSMMNAGVFSDFG
RGGGGGGKEGSTSLSVDVRGANSGAQSGDGEYLKGTEEEGS

**SEQ ID NO : 21 *Oryza sativa* SYT2 cDNA (AK105366)**

ATGCAGCAGCAGCCGATGCCGATGCCCGCGCAGGCGCCGCCGACGGCCGGAATCACCACCGA
GCAGATCCAAAAGTATCTGGATGAAAACAAGCAGCTTATTTTGGCTATTTTGGAAAATCAGA
ATCTGGGAAAGTTGGCAGAATGTGCTCAGTATCAAGCGCAGCTTCAGAAGAATCTCTTGTAC
TTGGCTGCAATTGCTGATACTCAACCGCAGACCACTATAAGCCGTCCCCAGATGGTGCCGCA
TGGTGCATCGCCGGGGTTAGGGGGGCAATACATGTCGCAGGTGCCAATGTTCCCCCCAGGA
CCCCTCTAACGCCCCAGCAGATGCAGGAGCAGCAGCTGCAGCAACAGCAAGCCCAGCTGCTC
TCGTTCGGCGGTCAGATGGTTATGAGGCCTGGCGTTGTGAATGGCATTCCTCAGCTTCTGCA
AGGCGAAATGCACCGCGGAGCAGATCACCAGAACGCTGGCGGGGCCACCTCGGAGCCTTCCG
AGAGCCACAGGAGCACCGGCACCGAAAATGACGGTGGAAGCGACTTCGGCGATCAATCCTAA

**SEQ ID NO : 22 *Oryza sativa* SYT2 protein**

MQQQPMPMPAQAPPTAGITTEQIQKYLDENKQLILAILENQNLGKLAECAQYQAQLQKNLLY
LAAIADTQPQTTISRPQMVPHGASPGLGGQYMSQVPMFPPRTPLTPQQMQEQQLQQQQAQLL
SFGGQMVMRPGVVNGIPQLLQGEMHRGADHQNAGGATSEPSESHRSTGTENDGGSDFGDQS

FIGURE 8 (continued)

SEQ ID NO : 23 *Oryza sativa* SYT3 cDNA (BP185008)

ATGCAGCAGCAGATGGCCATGCCGGCGGGGGCCGCCGCCGCCGCGGTGCCGCCGGCGGCCGG
CATCACCACCGAGCAGATCCAAAAGTATTTGGATGAAAATAAACAGCTAATTTTGGCCATCC
TGGAAAATCAAAACCTAGGGAAGTTGGCTGAATGTGCTCAGTACCAAGCTCAGCTTCAAAAG
AATCTCTTGTATCTGGCTGCCATTGCAGATGCCCAACCACCTCAGAATCCAGGAAGTCGCCC
TCAGATGATGCAGCCTGGTGCTACCCCAGGTGCTGGGCATTACATGTCCCAAGTACCGATGT
TCCCTCCAAGAACTCCCTTAACCCCACAACAGATGCAAGAGCAGCAGCAGCAGCAACTCCAG
CAACAGCAAGCTCAGGCTCTAGCCTTCCCCGGCCAGATGCTAATGAGACCAGGTACTGTCAA
TGGCATGCAATCTATCCCAGTTGCTGACCCTGCTCGCGCAGCCGATCTTCAGACGGCAGCAC
CGGGCTCGGTAGATGGCCGAGGAAACAAGCAGGATGCAACCTCGGAGCCTTCCGGGACCGAG
AGCCACAAGAGTGCGGGAGCAGATAACGACGCAGGCGGTGACATAGCGGAGAAGTCCTGA

SEQ ID NO : 24 *Oryza sativa* SYT3 protein

MQQQMAMPAGAAAAAVPPAAGITTEQIQKYLDENKQLILAILENQNLGKLAECAQYQAQLQK
NLLYLAAIADAQPPQNPGSRPQMMQPGATPGAGHYMSQVPMFPPRTPLTPQQMQEQQQQQLQ
QQQAQALAFPGQMLMRPGTVNGMQSIPVADPARAADLQTAAPGSVDGRGNKQDATSEPSGTE
SHKSAGADNDAGGDIAEKS

SEQ ID NO : 25 *Solanum tuberosum* SYT cDNA (BG590990)

ATGCAGCAGCAGCACCTGATGCAGATGCAGCCCATGATGGCAGCCTATTATCCCAACAATGT
CACTACTGATCATATTCAACAGTTCCTGGATGAGAACAAATCACTTATTCTGAAGATTGTTG
AGAGCCAGAACTCTGGGAAAATAAGTGAATGTGCAGAGTCCCAAGCTAAACTTCAGAGAAAT
CTTATGTACCTTGCAGCTATTGCTGATTCACAGCCCCAGCCTCCTAGTATGCATTCACAGTT
AGCTTCTGGTGGGATGATGCAGGGAGGGCACATTATATGCAGCAACAACAAGCTCAACAAC
TCACAACGCAATCGCTTATGGCTGCAGCAAGATCCTCCTCCTCAATGCTCTATGGACAACAA
CAACAACAACAACAACAACTATCATCATTGCAACAACAGCAAGCAGCCTTTCATAGCCA
GCAACTCGGAATGAGCAGCTCTGGTGGAGGAAGCAGTAGTGGACTTCACATGCTACAAAGCG
AAAACACTCATAGTGCTAGCACTGGTGGTGGGTGGTTTCCCTGA

SEQ ID NO : 26 *Solanum tuberosum* SYT protein

MQQQHLMQMQPMMAAYYPNNVTTDHIQQFLDENKSLILKIVESQNSGKISECAESQAKLQRN
LMYLAAIADSQPQPPSMHSQLASGGMMQGGAHYMQQQQAQQLTTQSLMAAARSSSSMLYGQQ
QQQQQQLSSLQQQQAAFHSQQLGMSSSGGGSSSGLHMLQSENTHSASTGGGWFP

SEQ ID NO : 27 *Zea mays* SYT1 cDNA (BG874129.1, CA409022.1; compiled)

ATGCAGCAGCAACACCTGATGCAGATGAACCAGAACATGATGGGGGGCTACACCTCTCCTGC
CGCCGTGACCACCGATCTCATCCAGCAGCACCTGGACGAGAACAAGCAGCTGATCCTGGCCA
TCCTCGACAACCAGAACAATGGCAAGGCGGAGGAGTGCGAACGGCACCAAGCTAAGCTCCAG
CACAACCTCATGTACCTGGCCGCCATCGCTGACAGCCAGCCGCCACAGACCGCGCCACTATC
ACAGTACCCGTCCAACCTGATGATGCAGCCGGGCCCTCGGTACATGCCACCGCAGTCCGGGC
AGATGATGAACCCGCAGTCGCTGATGGCGGCGCGGTCCTCCATGATGTACGCGCACCCGTCC
CTGTCGCCACTCCAGCAGCAGCAGGCGGCGCACGGACAGCTGGGTATGGCTCCAGGGGGCGG
CGGTGGCGGCACGACCAGCGGGTTCAGCATCCTCCACGGCGAGGCCAGCATGGGCGGTGGTG
GTGCTGGCGCAGGCGCCGGCAACAACATGATGAACGCCGGCATGTTCTCGGGCTTTGGCCGC
AGCGGCAGTGGCGCCAAGGAAGGGTCGACCTCTCTGTCGGTTGACGTCCGGGGTGGAACCAG
CTCCGGCGCGCAGAGCGGGGACGGCGAGTACCTCAAAGTCGGCACCGAGGAAGAAGGCAGTT
AG

SEQ ID NO : 28 *Zea mays* SYT1 protein

MQQQHLMQMNQNMMGGYTSPAAVTTDLIQQHLDENKQLILAILDNQNNGKAEECERHQAKLQ
HNLMYLAAIADSQPPQTAPLSQYPSNLMMQPGPRYMPPQSGQMMNPQSLMAARSSMMYAHPS
LSPLQQQQAAHGQLGMAPGGGGGGTTSGFSILHGEASMGGGGAGAGAGNNMMNAGMFSGFGR
SGSGAKEGSTSLSVDVRGGTSSGAQSGDGEYLKVGTEEEGS

SEQ ID NO : 29 *Zea mays* SYT2 cDNA (AY106697)

ATGCAGCAGCCGATGCACATGCAGCCACAGGCGCCGGCGATAACCCCAGCTGCCGGAATCAG
CACGGAGCAGATCCAAAAGTATCTGGATGAGAATAAGCAGCTTATTTTGGCTATTTTGGAAA
ATCAGAACCTAGGAAAATTGGCAGAATGTGCTCAGTATCAATCACAACTTCAGAAGAACCTC
TTGTATCTCGCTGCAATCGCAGATGCTCAACCGCAGACTGCTGTAAGCCGCCCTCAGATGGC
GCCGCCTGGTGGATCGCCTGGAGTAGGGCAGTACATGTCACAGGTGCCTATGTTCCCACCGA
GGACACCTCTTACACCCCAGCAGATGCAGGAGCAGCAGCTTCAGCAGCAGCAGGCTCAGTTG
CTAAACTTCAGTGGCCAAATGGTTGCTAGACCAGGCATGGTCAACGGCATGGCTCAGTCCAT
GCAAGCTCAGCTACCACCGGGTGTGAACAAGCAGGATGCTGGTGGGTCGCCTCTGAGCCCT
CGGGCACCGAGAGCCACAGGAGCACTGGTGGTGACGATGGTGGAAGCGACTAG

SEQ ID NO : 30 *Zea mays* SYT2 protein

MQQPMHMQPQAPAITPAAGISTEQIQKYLDENKQLILAILENQNLGKLAECAQYQSQLQKNL
LYLAAIADAQPQTAVSRPQMAPPGGSPGVGQYMSQVPMFPPRTPLTPQQMQEQQLQQQQAQL
LNFSGQMVARPGMVNGMAQSMQAQLPPGVNKQDAGGVASEPSGTESHRSTGGDDGGSD

FIGURE 8 (continued)

SEQ ID NO : 31 *Homo sapiens* cDNA (CR542103)

ATGGGCGGCAACATGTCTGTGGCTTTCGCGGCCCCGAGGCAGCGAGGCAAGGGGGAGATCAC
TCCCGCTGCGATTCAGAAGATGTTGGATGACAATAACCATCTTATTCAGTGTATAATGGACT
CTCAGAATAAAGGAAAGACCTCAGAGTGTTCTCAGTATCAGCAGATGTTGCACACAAACTTG
GTATACCTTGCTACAATAGCAGATTCTAATCAAAATATGCAGTCTCTTTTACCAGCACCACC
CACACAGAATATGCCTATGGGTCCTGGAGGGATGAATCAGAGCGGCCCTCCCCCACCTCCAC
GCTCTCACAACATGCCTTCAGATGGAATGGTAGGTGGGGGTCCTCCTGCACCGCACATGCAG
AACCAGATGAACGGCCAGATGCCTGGGCCTAACCATATGCCTATGCAGGGACCTGGACCCAA
TCAACTCAATATGACAAACAGTTCCATGAATATGCCTTCAAGTAGCCATGGATCCATGGGAG
GTTACAACCATTCTGTGCCATCATCACAGAGCATGCCAGTACAGAATCAGATGACAATGAGT
CAGGGACAACCAATGGGAAACTATGGTCCCAGACCAAATATGAGTATGCAGCCAAACCAAGG
TCCAATGATGCATCAGCAGCCTCCTTCTCAGCAATACAATATGCCACAGGGAGGCGGACAGC
ATTACCAAGGACAGCAGCCACCTATGGGAATGATGGGTCAAGTTAACCAAGGCAATCATATG
ATGGGTCAGAGACAGATTCCTCCCTATAGACCTCCTCAACAGGGCCCACCACAGCAGTACTC
AGGCCAGGAAGACTATTACGGGGACCAATACAGTCATGGTGGACAAGGTCCTCCAGAAGGCA
TGAACCAGCAATATTACCCTGATGGAAATTCACAGTATGGCCAACAGCAAGATGCATACCAG
GGACCACCTCCACAACAGGGATATCCACCCCAGCAGCAGCAGTACCCAGGGCAGCAAGGTTA
CCCAGGACAGCAGCAGGGCTACGGTCCTTCACAGGGTGGTCCAGGTCCTCAGTATCCTAACT
ACCCACAGGGACAAGGTCAGCAGTATGGAGGATATAGACCAACACAGCCTGGACCACCACAG
CCACCCCAGCAGAGGCCTTATGGATATGACCAGGGACAGTATGGAAATTACCAGCAG

SEQ ID NO : 32 *Homo sapiens* SYT protein (CAG46900.1)

MGGNMSVAFAAPRQRGKGEITPAAIQKMLDDNNHLIQCIMDSQNKGKTSECSQYQQMLHTNL
VYLATIADSNQNMQSLLPAPPTQNMPMGPGGMNQSGPPPPPRSHNMPSDGMVGGGPPAPHMQ
NQMNGQMPGPNHMPMQGPGPNQLNMTNSSMNMPSSSHGSMGGYNHSVPSSQSMPVQNQMTMS
QGQPMGNYGPRPNMSMQPNQGPMMHQQPPSQQYNMPQGGGQHYQGQQPPMGMMGQVNQGNHM
MGQRQIPPYRPPQQGPPQQYSGQEDYYGDQYSHGGQGPPEGMNQQYYPDGNSQYGQQQDAYQ
GPPPQQGYPPQQQQYPGQQGYPGQQQGYGPSQGGPGPQYPNYPQGQGQQYGGYRPTQPGPPQ
PPQQRPYGYDQGQYGNYQQ

SEQ ID NO : 33 *Allium cepa* SYT2 cDNA CF437485

ATGCAGCAGCCGCAGCCAGCGATGGGAACCATGGGCTCGGTGCCACCTACTAGCATCACCAC
CGAACAGATTCAAAGGTACTTGGATGAGAACAAACAGTTAATATTGGCAATTTTGGATAATC
AAAATTTAGGAAGACTGAATGAGTGTGCTCAATATCAAGCTCAGCTTCAAAAGAATCTGCTT
TACCTGGCAGCAATAGCTGATGCTCAGCCTCAGTCTCCTGCGGTGCGTCTGCAGATGATGCC
TCAAGGTGCAGCTGCCACGCCTCAAGCTGGAAACCAATTTATGCAGCAGCAGAGCCCTAATT
TCCCTCCCAAAACAGGAATGCAATTTACTCCTCAACAAGTACAAGAATTGCAGCAGCAACAG
CTACAACATCAGCCACATATGATGCCTCCATTTCAAGGTCAAATGGGTATGAGACCTATGAA
TGGAATGCAGGCAGCAATGCATGCAGATTCATCTCTTGCTTATAACACTAACAATAAGCAAG
ATGCAGGAAACGCAGCTTATGAAAATACTGCTGCCAACACAGATGGTTCCATTCAAAAGAAA
ACAGCAAATGATGATTTAGACCCTTCTGCAGCAAACCCTAGAAGGTCTGAAGATGCCAAATC
ATCATGA

FIGURE 8 (continued)

SEQ ID NO : 34 *Allium cepa* SYT2 translated amino acid sequence

MQQPQPAMGTMGSVPPTSITTEQIQRYLDENKQLILAILDNQNLGRLNECAQYQAQLQKNLL
YLAAIADAQPQSPAVRLQMMPQGAAATPQAGNQFMQQQSPNFPPKTGMQFTPQQVQELQQQQ
LQHQPHMMPPFQGQMGMRPMNGMQAAMHADSSLAYNTNNKQDAGNAAYENTAANTDGSIQKK
TANDDLDPSAANPRRSEDAKSS

SEQ ID NO : 35 *Aquilegia formosa* x *Aquilegia pubescens* SYT1 cDNA DT758802.1

ATGCAACACATGCAGATGCAGCCCATGATGCCACCTTATAGTGCCAACAGCGTCACTACTGA
TCATATCCAACAGTACTTGGATGAAAATAAGGCGTTGATTCTGAAGATACTTGAGAACCAAA
ATTCGGGAAAAGTTAGTGAATGTGCAGAGAACCAAGCAAGACTTCAACGAAATCTTATGTAT
CTGGCTGCAATTGCTGATTCTCAACCACAGCCTCCCAATATGCATGCTCAGTACTCTAATGC
GGGTATACCACCTGGTGCACATTACCTACAACACCAACAGGCCCAACAGATGACACAACAGT
CGCTCATGGCTGCTCGATCAAATATGCTGTATGCTCAGCCAATCACAGGAATGCAGCAACAG
CAAGCAATGCATAGCCAGCTTGGCATGAGCTCTGGTGGTAACAGTGGACTCCACATGATGCA
CAATGAGGGCAGCATGGGAGGTAGTGGGGCACTTGGAAGCTATTCTGATTATGGCCGTGGCA
GTGGTGGTGGAGTAACTATCGCTAGCAAACAAGATGGTGGAAGTGGTTCTGGTGAAGGACGA
GGTGGAAACTCTGGAGGCCAAAGTGCAGATGGAGGTGAATCTCTTTACCTGAAAAACAGTGA
CGAAGGGAACTAA

SEQ ID NO : 36 *Aquilegia formosa* x *Aquilegia pubescens* SYT1 translated amino acid sequence MQHMQMQPMMPPYSANSVTTDHIQQYLDENKALILKILENQNSGKVSECAENQARLQRNLMY
LAAIADSQPQPPNMHAQYSNAGIPPGAHYLQHQQAQQMTQQSLMAARSNMLYAQPITGMQQQ
QAMHSQLGMSSGGNSGLHMMHNEGSMGGSGALGSYSDYGRGSGGGVTIASKQDGGSGSGEGR
GGNSGGQSADGGESLYLKNSDEGN

SEQ ID NO : 37 *Brachypodium distachyon* SYT23 cDNA DV480064.1

ATGCAGCAGGCGATGTCCATGTCCCCGGGGTCGGCCGGCGCGGTGCCGCCTCCGGCCGGCAT
CACCACAGAGCAGATCCAAAAGTATTTGGATGAAAATAAGCAACTTATTTGGCCATCCTGG
AAAATCAGAACCTAGGAAAGTTGACTGAATGTGCTCAGTATCAAGCTCAACTTCAGAAGAAT
CTCTTGTATCTGGCTGCCATTGCGGATGCCCAACCACCACAGAACCCTGGAAGTCGCCCCCA
GATGGTGCAGCCTGGTGGTATGCCAGGTGCAGGGCATTACATGTCGCAAGTACCAATGTTCC
CTCCAAGAACCCCTTTAACCCCACAACAGATGCAAGAGCAACAGCACCAGCAGCTTCAGCAG
CAGCAAGCACAGGCTCTTGCTTTCCCCAGCCAGATGGTCATGAGACCAGGTACTGTAACGG
CATGCAGCCTATGCAAGCTGATCTCCAAGCAGCAGCAGCAGCACCTGGCCTGGCAGACAGCC
GAGGAAGTAAGCAGGACGCAGCGGTAGCTGGGGCCATCTCGGAACCTTCTGGCACCGAGAGT
CACAAGAGTACAGGAGCGGATCATGAGGCAGGTGGCGATGTAGCTGAGCAATCCTAA

FIGURE 8 (continued)

SEQ ID NO : 38 *Brachypodium distachyon* SYT3 translated amino acid sequence MQQAMSMSPGSAGAVPPPAGITTEQIQKYLDENKQLILAILENQNLGKLTECAQYQAQLQKN
LLYLAAIADAQPPQNPGSRPQMVQPGGMPGAGHYMSQVPMFPPRTPLTPQQMQEQQHQQLQQ
QQAQALAFPSQMVMRPGTVNGMQPMQADLQAAAAAPGLADSRGSKQDAAVAGAISEPSGTES
HKSTGADHEAGGDVAEQS

SEQ ID NO : 39 *Brassica napus* SYT2 cDNA CN732814

ATGCAGCAGCAGCAGCAGCAGCAGCAGCAGCCTCCGCAAATGTTTCCGATGGCTCCTTCGAT
GCCGCCAACTAACATCACCACCGAACAGATCCAAAAGTACCTTGAGGAGAACAAGAAGCTGA
TAATGGCAATCATGGAAAATCAGAATCTTGGCAAGCTTGCAGAGTGTGCACAGTACCAAGCT
CTTCTCCAGAAGAACTTAATGTACCTCGCTGCTATTGCTGATGCTCAACCTCCTCCATCTAC
CGCTGGAGCTACACCACCACCAGCTATGGCTTCCCAGATGGGGGCACCGCATCCTGGGATGC
AACCGCCGAGCTACTTTATGCAACACCCACAAGCTTCAGGGATGGCTCAACAAGCACCACCC
GCTGGTATCTTCCCTCCGAGAGGTCCTTTGCAGTTTGGTAGCCCACACCAGCTTCAGGATCC
GCAACAGCAGCATATGCATCAACAGGCTATGCAAGGACACATGGGGATGCGACCAATGGGTA
TCAACAACAACAATGGATGCAGCATCAGATGCAGCAACAACAACCAGAAACCTCTCTTGGA
GGAAGCGCTGCAAACGTGGGGCTTAGAGGTGGAAAGCAAGATGGAGCAGATGGACAAGGAAA
AGATGATGGCAAATGA

SEQ ID NO : 40 *Brassica napus* SYT2 translated amino acid sequence

MQQHLMQMQPMMAGYYPSNVTSDHIQQYLDENKSLILKIVESQNSGKLSECAENQARLQRNL
MYLAAIADSQPQPPSVHSQYGSAGGGLIQGEGASHYLQQQQATQQQQMTQQSLMAARSSMMY
QQQQQPYATLQHQQLHHSQLGMSSSSGGGSSGLHILQGEAGGFHEFGRGKPEMGSGEGRGGS
SGDGGETLYLKSSDDGN

SEQ ID NO : 41 *Citrus sinensis* SYT2 cDNA CV717501

ATGCAGCAGCCACCGCAAATGATCCCTGTTATGCCTTCATTTCCACCCACCAACATCACCAC
AGAGCAGATTCAAAAGTACCTTGATGAGAACAAAAAGTTGATTTTGGCAATTTTGGACAATC
AAAATCTTGGAAAGCTTACAGAATGTGCCCACTATCAAGCTCAGCTTCAAAAGAATTTAATG
TATTTAGCTGCAATTGCTGATGCACAACCACAAGCACCAACAATGCCTCCTCAGATGGCTCC
ACATCCTGCAATGCAAGCTAGTGGGTATTACATGCAACATCCTCAGGCGGCAGCAATGGCTC
AGCAACAAGGAATCTTTCCCCAAAAGATGCCATTACAATTCAATAACCCTCATCAACTACAG
GATCCTCAACAGCAGCTACACCAACATCAAGCCATGCAAGCACAAATGGGAATGAGACCGGG
TGCCACTAACAATGGTATGCATCCCATGCATGCTGAAGCTCTCTTGGAGGTGGCAGCAGTG
GAGGACCCCCTTCAGCATCAGGCCCAGGTGACATACGTGGTGGAAATAAGCAAGATGCCTCG
GAGGCTGGGACTACTGGTGCTGATGGCCAGGGCAGTTCGGCTGGTGGGCATGGTGGGGATGG
AGAGGAGGCAAAGTGA

FIGURE 8 (continued)

SEQ ID NO : 42 *Citrus sinensis* SYT2 translated amino acid sequence

MQQPPQMIPVMPSFPPTNITTEQIQKYLDENKKLILAILDNQNLGKLTECAHYQAQLQKNLM
YLAAIADAQPQAPTMPPQMAPHPAMQASGYYMQHPQAAAMAQQQGIFPQKMPLQFNNPHQLQ
DPQQQLHQHQAMQAQMGMRPGATNNGMHPMHAESSLGGGSSGGPPSASGPGDIRGGNKQDAS
EAGTTGADGQGSSAGGHGGDGEEAK

SEQ ID NO : 43 *Euphorbia esula* SYT2 cDNA DV144834

ATGCAGCAGCAACCGCAGATGATGCCTATGATGCCTTCATATCCACCAGCAAACATTACCAC
GGAGCAAATCCAAAAGTATCTTGATGAAAATAAAAAATTGATTTTGGCGATCTTGGATAATC
AAAATCTTGGAAAACTCGCTGAGTGTGCACAGTATCAAGCCCTGCTGCAAAAAAATCTGATG
TATTTAGCCGCAATTGCTGATGCACAACCCCAGACCCCACCCATGCCACCTCAGATGTCCCC
ACATCCGGCTATGCAACAAGGAGCATATTACATGCAACATCCTCAGGCTGCAGCAGCAGCAA
TGGCTCATCAGTCGGGTATTTTCCCACCAAAGATGTCTCCGTTACAATTCAATAATCCTCAT
CAAATACAGGACCCCCAGCAGTTACATCAAGCAGCCCTCCAAGGGCAAATGGGAATGAGGCC
CATGGGGCCCAATAACGGGATGCATCCGATGCACCCCGAGGCAAATCTTGGAGGATCTAATG
ATGGTCGTGGAGGAAACAAACAGGATGCTCCGGAGACGGGAGCATCGGGAGGTGATGGGCAA
GGCAATTCTGGTGGTGATGGGGCTGAAGATGGGAAATGA

SEQ ID NO : 44 *Euphorbia esula* SYT2 translated amino acid sequence

MQQQPQMMPMMPSYPPANITTEQIQKYLDENKKLILAILDNQNLGKLAECAQYQALLQKNLM
YLAAIADAQPQTPPMPPQMSPHPAMQQGAYYMQHPQAAAAAMAHQSGIFPPKMSPLQFNNPH
QIQDPQQLHQAALQGQMGMRPMGPNNGMHPMHPEANLGGSNDGRGGNKQDAPETGASGGDGQ
GNSGGDGAEDGK

SEQ ID NO : 45 *Glycine max* SYT2 cDNA BQ612648

ATGCAGCAGACACCGCCAATGATTCCTATGATGCCTTCTTTCCCACCTACGAACATAACCAC
CGAGCAGATTCAAAAATACCTTGATGAGAACAAGAAGCTGATTCTGGCAATATTGGACAATC
AAAATCTTGGAAAACTTGCAGAATGTGCCCAGTACCAAGCTCAGCTTCAAAAGAATTTGATG
TATTTAGCTGCAATTGCTGATGCCCAGCCTCAAACCCCGGCCATGCCTCCGCAGATGGCACC
GCACCCTGCCATGCAACCAGGATTCTATATGCAACATCCTCAGGCTGCTGCAGCAGCAATGG
CTCAGCAGCAGCAAGGAATGTTCCCCCAGAAAATGCCATTGCAATTTGGCAATCCACATCAA
ATGCAGGAACAACAACAGCAGCTACACCAGCAGGCCATCCAAGGTCAAATGGGACTTAGACC
TGGAGATATAAATAATGGCATGCATCCAATGCACAGTGAGGCTGCTCTTGGAGGTGGAAACA
GCGGTGGTCCACCTTCGGCTACTGGTCCAAACGATGCACGTGGTGGAAGCAAGCAAGATGCC
TCTGAGGCTGGAACAGCTGGTGGAGACGGCCAAGGCAGCTCCGCGGCTGCTCATAACAGTGG
AGATGGTGAAGAGGCAAAGTGA

SEQ ID NO : 46 *Glycine max* SYT2 translated amino acid sequence

MQQTPPMIPMMPSFPPTNITTEQIQKYLDENKKLILAILDNQNLGKLAECAQYQAQLQKNLM
YLAAIADAQPQTPAMPPQMAPHPAMQPGFYMQHPQAAAAAMAQQQQGMFPQKMPLQFGNPHQ
MQEQQQQLHQQAIQGQMGLRPGDINNGMHPMHSEAALGGGNSGGPPSATGPNDARGGSKQDA
SEAGTAGGDGQGSSAAAHNSGDGEEAK

SEQ ID NO : 47 *Glycine soya* SYT2 cDNA CA799921

ATGCAGCAGACACCGCCTATGATTCCTATGATGCCTTCGTTCCCACCTACGAACATAACCAC
CGAGCAGATTCAAAAATACCTTGATGAGAACAAGAAGCTGATTCTGGCAATATTGGACAATC
AAAATCTTGGAAAACTTGCAGAATGTGCCCAGTACCAAGCTCAGCTTCAAAAGAATTTGATG
TATTTAGCTGCAATTGCTGATGCCCAGCCTCAAACACCAGCCATGCCTCCACAGATGGCACC
ACACCCTGCCATGCAACCAGGATTCTATATGCAACATCCTCAGGCTGCAGCAGCAGCAATGG
CTCAGCAGCAGCAGCAAGGAATGTTCCCCCAGAAAATGCCATTGCAATTTGGCAATCCACAT
CAAATGCAGGAACAACAGCAGCAGCTACACCAGCAAGCCATCCAAGGTCAAATGGGACTGAG
ACCTGGAGGAATAAATAATGGCATGCATCCAATGCACAATGAGGGCGGCAACAGCGGTGGTC
CACCCTCGGCTACCGGTCCGAACGACGCACGTGGTGGAAGCAAGCAAGATGCTTCTGAGGCT
GGAACAGCTGGTGGAGATGGCCAAGGCAGCTCTGCAGCTGCTCATAACAGTGGAGATGGTGA
AGAGGCAAAGTGA

SEQ ID NO : 48 *Glycine soya* SYT2 translated amino acid sequence

MQQTPPMIPMMPSFPPTNITTEQIQKYLDENKKLILAILDNQNLGKLAECAQYQAQLQKNLM
YLAAIADAQPQTPAMPPQMAPHPAMQPGFYMQHPQAAAAAMAQQQQGMFPQKMPLQFGNPH
QMQEQQQQLHQQAIQGQMGLRPGGINNGMHPMHNEGGNSGGPPSATGPNDARGGSKQDASEA
GTAGGDGQGSSAAAHNSGDGEEAK

SEQ ID NO : 49 *Gossypium hirsutum* SYT1 cDNA DT558852

ATGCAGCAGCACCTGATGCAGATGCAGCCCATGATGGCAGCTTATTATCCCAACAACGTCAC
TACTGATCATATTCAACAGTATCTCGATGAGAACAAGTCATTGATCTTAAAGATTGTTGAGA
GCCAGAATTCTGGGAAATTGAGTGAATGTGCTGAGAACCAAGCAAGGCTGCAGCGAAACCTC
ATGTACCTGGCTGCCATTGCGGATTCTCAACCCCAACCACCCACCGTGCATGCACAGTTTCC
ATCTGGTGGTATCATGCAGCCAGGAGCTGGGCACTACATGCAGCACCAACAAGCTCAACAAA
TGACACAACAGTCGCTTATGGCTGCTCGGTCCTCAATGTTGTATTCTCAGCAACCATTTTCT
GCACTGCAACAACAACAGCAGCAAGCTTTGCACAGTCAGCTTGGCATGAGCTCTGGCGGAAG
CACAGGCCTTCATATGCTGCAAACTGAATCTAGTACTGCAGGTGGCAGTGGAGCACTTGGGG
CCGGAGGGTTTCCTGATTTTGGACGTGGTTCTTCTGGAGAAGGCATCCATGGTGGCAGGCCA
ATGGCAGGTGGAAGCAAGCAAGATATCGGGAGTGCCGGCTCAGCTGAAGGTCGTGGAGGAAG
CTCTGGTGGTCAGGGTGGTGGTGATGGGGGTGAAACCCTTTACTTAAAAGCAGCCGATGATG
GGAACTGA

FIGURE 8 (continued)

SEQ ID NO : 50 *Gossypium hirsutum* SYT1 translated amino acid sequence

MQQHLMQMQPMMAAYYPNNVTTDHIQQYLDENKSLILKIVESQNSGKLSECAENQARLQRNL
MYLAAIADSQPQPPTVHAQFPSGGIMQPGAGHYMQHQQAQQMTQQSLMAARSSMLYSQQPFS
ALQQQQQQALHSQLGMSSGGSTGLHMLQTESSTAGGSGALGAGGFPDFGRGSSGEGIHGGRP
MAGGSKQDIGSAGSAEGRGGSSGGQGGGDGGETLYLKAADDGN

SEQ ID NO : 51 *Gossypium hirsutum* SYT2 cDNA DT563805

ATGCCGCAGCCACCGCAAATGATTCCTGTGATGCCTTCATATCCACCTACTAATATCACTAC
TGAACAGATTCAGAAGTACCTTGATGAGAATAAGAAGTTGATTTTGGCAATTTTGGACAATC
AGAATCTTGGAAAACTCGCTGAATGCGCCCAGTATCAAGCTCAGCTGCAAAAGAATTTGATG
TATTTAGCTGCAATTGCGGATGCTCAACCTCAATCAACGCCAGCAATGTCGCCTCAGATGGC
ACCGCATCCAGCAATGCAACCCGGAGGATATTTATGCAACATCCTCAAGCTGCTGCAATGT
CACAGCAACCTGGCATGTACCCTCAAAAGGTGCCATTGCAATTCAATAGTCCGCATCAAATG
CAGGACCCTCAGCACCTCCTATATCAGCAGCATCAACAAGCAATGCAAGGTCAAATGGGAAT
CAGGCCTGGGGGACCCAATAATAGCATGCATCCCATGCATTCAGAGGCTAGCCTTGGAGGCG
GCAGCAGTGGTGGTCCCCCTCAACCTTCAGGCCCAAGTGATGGACGTGCTGGAAACAAGCAA
GAGGGCTCCGAAGCTGGTGGTAATGGGCAGGGCAGCACAACTGGTGGGCATGGTGGCGGTGA
TGGAGCGGATGAGGCAAAGTGA

SEQ ID NO : 52 *Gossypium hirsutum* SYT2 translated amino acid sequence

MPQPPQMIPVMPSYPPTNITTEQIQKYLDENKKLILAILDNQNLGKLAECAQYQAQLQKNLM
YLAAIADAQPQSTPAMSPQMAPHPAMQPGGYFMQHPQAAAMSQQPGMYPQKVPLQFNSPHQM
QDPQHLLYQQHQQAMQGQMGIRPGGPNNSMHPMHSEASLGGGSSGGPPQPSGPSDGRAGNKQ
EGSEAGGNGQGSTTGGHGGGDGADEAK

SEQ ID NO : 53 *Hordeum vulgare* SYT2 cDNA CA032350

ATGCAGCAAGCGATGCCCATGCCGCCGGCGGCGGCGGCGCCTGGGATGCCTCCTTCTGCCGG
CCTCAGCACCGAGCAGATCCAAAAGTACCTGGATGAAAATAAACAACTAATTTTGGCTATCT
TGGAAAATCAGAACCTGGGAAAGTTGGCGGAATGTGCTCAGTATCAAGCTCAGCTTCAGAAG
AATCTTTTGTATTTGGCTGCGATTGCTGATACTCAGCCACAGACCTCTGTAAGCCGTCCTCA
GATGGCACCACCTGCTGCATCCCCAGGGGCAGGGCATTACATGTCACAGGTGCCAATGTTCC
CTCCGAGGACCCCTCTAACGCCTCAGCAGATGCAGGAGCAGCAACTACAGCAACAACAGGCT
CAGATGCTTCCGTTTGCTGGTCAAATGGTTGCGAGACCCGGGGCTGTCAATGGCATTCCCCA
GGCCCCTCAAGTTGAACAACCAGCCTATGCAGCAGGTGGGGCCAGTTCCGAGCCTTCTGGCA
CCGAGAGCCACAGGAGCACTGGCGCCGATAACGATGGTGGGAGCGGCTTGGCTGACCAGTCC
TAA

FIGURE 8 (continued)

SEQ ID NO : 54 *Hordeum vulgare* SYT2 translated amino acid sequence

MQQAMPMPPAAAAPGMPPSAGLSTEQIQKYLDENKQLILAILENQNLGKLAECAQYQAQLQK
NLLYLAAIADTQPQTSVSRPQMAPPAASPGAGHYMSQVPMFPPRTPLTPQQMQEQQLQQQQA
QMLPFAGQMVARPGAVNGIPQAPQVEQPAYAAGGASSEPSGTESHRSTGADNDGGSGLADQS

SEQ ID NO : 55 *Lactuca serriola* SYT1 cDNA DW110765

ATGAAGCAGCCGATGATGCCGAATCCAATGATGTCTTCTTCGTTTCCTCCTACAAACATCAC
CACCGATCAGATCCAAAAGTTCCTTGATGAAAACAAGCAACTAATTATAGCAATAATGAGCA
ACCTAAATCTTGGAAAGCTTGCTGAATGTGCCCAGTACCAAGCTCTACTCCAAAAAAATTTG
ATGTATCTAGCAGCCATTGCAGATGCTCAACCACCTACACCTACACCAACACTAAATATCTC
TTATNAGATGGGCCCGGTTCCACATCCAGGGATGCCACAGCAAGGTGGATTTTACATGGCGC
AGCAGCACCCTCAGGCGGCTGTAATGACGGCTCAGCCACCTTCTGGTTTTCCACAACCGATG
CCTGGTATGCAATTTAACAGCCCACAGGCTATTCAAGGGCAGATGGGCGGGAGGTCCGGTGG
GCCGCCAAGCTCAGCCGCTAGTGATGTCTGGAGAGGAAGCATGCAAGATGGTGGTGGTGGTG
CTGCTGCTGATGGTGGTAAGGATGGTCATGCTGGCGGTGGACCTGAGGAAGCAAAGTAA

SEQ ID NO : 56 *Lactuca serriola* SYT1 translated amino acid sequence

MKQPMMPNPMMSSSFPPTNITTDQIQKFLDENKQLIIAIMSNLNLGKLAECAQYQALLQKNL
MYLAAIADAQPPTPTPTLNISYXMGPVPHPGMPQQGGFYMAQQHPQAAVMTAQPPSGFPQPM
PGMQFNSPQAIQGQMGGRSGGPPSSAASDVWRGSMQDGGGGAAADGGKDGHAGGGPEEAK

SEQ ID NO : 57 *Lycopersicon esculentum* SYT1 cDNA AW934450.1 BP893155.1

ATGCAGCAGCACCTGATGCAGATGCAGCCCATGATGGCAGCTTACTATCCAACGAACGTCAC
TACTGACCATATTCAACAGTATTTGGATGAAAACAAATCACTCATTCTGAAGATTGTTGAGA
GCCAGAACTCTGGGAAACTCAGTGAATGTGCGGAGAACCAAGCTAGGCTTCAGAGGAATCTG
ATGTACCTTGCTGCGATTGCTGATTCACAACCTCAACCTTCTAGCATGCATTCTCAGTTCTC
TTCTGGTGGGATGATGCAGCCAGGGACACACAGTTACTTGCAGCAGCAGCAGCAGCAACAAC
AAGCGCAACAAATGGCAACACAACAACTCATGGCTGCAAGATCCTCGTCGATGCTCTATGGA
CAACAGCAGCAGCAATCTCAGTTATCGCAATATCAACAAGGCTTGCATAGTAGCCAACTCGG
CATGAGTTCTGGCAGTGGCGGAAGCACTGGACTTCATCACATGCTTCAAAGTGAATCATCAC
CTCATGGTGGTGGTTTCTCTCATGACTTCGGCCGCGCAAATAAGCAAGACATTGGGAGTAGT
ATGTCTGCTGAAGGGCGCGGCGGAAGTTCAGGTGGTGAGAATCTTTATCTGAAAGCTTCTGA
GGATTGA

SEQ ID NO : 58 *Lycopersicon esculentum* SYT1 translated amino acid sequence MQQHLMQMQPMMAAYYPTNVTTDHIQQYLDENKSLILKIVESQNSGKLSECAENQARLQRNL
MYLAAIADSQPQPSSMHSQFSSGGMMQPGTHSYLQQQQQQQQAQQMATQQLMAARSSSMLYG
QQQQQSQLSQYQQGLHSSQLGMSSGSGGSTGLHHMLQSESSPHGGGFSHDFGRANKQDIGSS
MSAEGRGGSSGGENLYLKASED

FIGURE 8 (continued)

SEQ ID NO : 59 *Malus domestica* SYT2 CV084230 DR997566

ATGCAGCAGCCACCACACAAATGATCCCCGTCATGCCTTCATTTCCTCCCACCAACATCACCAC
CGAACAAATTCAGAAGTACCTTGATGACAACAAAAAGTTGATTCTGGCAATATTGGATAATC
AAAATCTTGGAAAACTTGCTGAGTGTGCTCAGTACCAGGCTCTGCTTCAAAAGAATCTGATG
TATTTAGCAGCAATTGCCGATGCGCAACCACAGGCACCAGCTGCCCCTCCCCAGATGGCCCC
ACATCCTGCTATGCAACAGGCAGGATATTACATGCAACATCCTCAGGCAGCAGCAATGGCTC
AGCAACAGGGTATTTTCTCCCCAAAGATGCCGATGCAATTCAATAACATGCATCAAATGCAC
GATCCACAGCAGCACCAACAAGCCATGCAAGGGCAAATGGGAATGAGACCTGGAGGGCCTAA
CGGCATGCCTTCCATGCTTCATACTGAGGCCACACATGGTGGTGGTAGTGGCGGCCCAAATT
CAGCTGGAGACCCAAATGATGGGCGTGGAGGAAGCAAGCAAGACGCCTCTGAGTCTGGGGCA
GGTGGTGATGGCCAGGGGACCTCAGCCGGCGGGCGTGGAACTGGTGATGGAGAGGACGGCAA
GTGA

SEQ ID NO : 60 *Malus domestica* SYT2 translated amino acid sequence

MQQPPQMIPVMPSFPPTNITTEQIQKYLDDNKKLILAILDNQNLGKLAECAQYQALLQKNLM
YLAAIADAQPQAPAAPPQMAPHPAMQQAGYYMQHPQAAAMAQQQGIFSPKMPMQFNNMHQMH
DPQQHQQAMQGQMGMRPGGPNGMPSMLHTEATHGGGSGGPNSAGDPNDGRGGSKQDASESGA
GGDGQGTSAGGRGTGDGEDGK

SEQ ID NO : 61 *Medicago trunculata* SYT2 cDNA CA858743 BI310799.1 AL382135.1

ATGCAGCAGACACCTCAAATGATTCCTATGATGCCTTCATTCCCACAACAAACAAACATAAC
CACTGAGCAGATTCAAAAATATCTTGATGAGAACAAGAAGCTGATCCTGGCAATATTGGACA
ATCAAAATCTTGGAAAACTTGCAGAATGTGCCCAGTACCAAGCTCAGCTTCAGAAGAATTTG
ATGTATTTAGCTGCAATTGCTGACGCGCAGCCACAAACACCGGCCTTGCCTCCACAGATGGC
CCCGCACCCTGCGATGCAACAAGGATTCTATATGCAACATCCTCAGGCTGCAGCAATGGCTC
AGCAACAAGGAATGTTCCCCCAAAAAATGCCAATGCAGTTCGGTAATCCGCATCAAATGCAG
GATCAGCAGCATCAGCAGCAACAACAGCAGCTACATCAGCAAGCTATGCAAGGTCAAATGGG
ACTTAGACCTGGAGGGATAAATAACGGCATGCATCCAATGCACAACGAGGCTGCTCTCGGAG
GTAGCGGCAGTGGTGGTCAAATGACGGGCGTGGTGGTGGAGCAAGCAAGATGCTTCGGAGCT
GGGACAGCCGGCGGTGATGGTCAAGGAACCTCTGCCGCAGCTGCGCACAACAGTGGAGATGC
TTCAGAAGAAGGAAAGTAA

SEQ ID NO : 62 *Medicago trunculata* SYT2 translated amino acid sequence

MQQTPQMIPMMPSFPQQTNITTEQIQKYLDENKKLILAILDNQNLGKLAECAQYQAQLQKNL
MYLAAIADAQPQTPALPPQMAPHPAMQQGFYMQHPQAAAMAQQQGMFPQKMPMQFGNPHQMQ
DQQHQQQQQQLHQQAMQGQMGLRPGGINNGMHPMHNEAALGGSGSGGPNDGRGGGSKQDASE
AGTAGGDGQGTSAAAAHNSGDASEEGK

FIGURE 8 (continued)

SEQ ID NO : 63 *Panicum virgatum* SYT3 cDNA DN152517

ATGCAGCAGCAGATGCCCATGCAGTCGGCGCCCCCGGCGACCGGCATCACCACCGAGCAGAT
CCAAAAGTATTTGGATGAAAATAAGCAGCTTATTTTGGCCATCCTGGAAAATCAGAACTTAG
GAAAGTTGGCTGAATGTGCTCAGTATCAAGCTCAGCTTCAAAAGAATCTCTTGTACCTGGCT
GCGATTGCAGATGCCCAACCCCAACCACCACAGAACCCTGCAAGTCGCCCACAGATGATGCA
ACCTGGCATGGTACCAGGTGCAGGGCATTACATGTCCCAAGTACCAATGTTCCCGCCAAGAA
CACCATTAACCCCGCAACAGATGCAAGAACAGCAGCAGCAGCAGCAGCAGCTTCAACAGCAG
CAAGCACAGGCTCTTGCTTTCCCGGGACAGATGGTCATGAGACCTACCATTAATGGCATGCA
GCCTATGCAAGCCGACCCTGCTGCCGCCGCCGCCAGCCTACAGCAGTCAGCACCTGGCCCTA
CTGATGGGCGAGGAGGCAAGCAAGATGCAACTGCTGGGGTGAGCACAGAGCCTTCTGGCACC
GAGAGCCACAAGAGCACAACCGCAGCAGATCACGATGTGGGCACTGATGTCGCGGAGAAATC
CTAA

SEQ ID NO : 64 *Panicum virgatum* SYT3 translated amino acid sequence

MQQQMPMQSAPPATGITTEQIQKYLDENKQLILAILENQNLGKLAECAQYQAQLQKNLLYLA
AIADAQPQPPQNPASRPQMMQPGMVPGAGHYMSQVPMFPPRTPLTPQQMQEQQQQQQQLQQQ
QAQALAFPGQMVMRPTINGMQPMQADPAAAAASLQQSAPGPTDGRGGKQDATAGVSTEPSGT
ESHKSTTAADHDVGTDVAEKS

SEQ ID NO : 65 *Picea sitchensis* SYT1 cDNA DR484100 DR478464.1

ATGCAGCAGCATCTCATGCAAATGCAGCCCATGATGGCGGCATACGCCTCCAACAACATCAC
CACTGATCACATCCAGAAGTACCTGGATGAGAACAAGCAGTTGATTCTGGCAATTCTGGACA
ACCAAAATCTTGGAAAGCTCAATGAGTGTGCTCAGTACCAAGCAAAACTTCAGCAGAATTTG
ATGTATCTGGCTGCGATTGCTGATTCTCAACCACAAGCACAAACTGCACATGCTCAGATTCC
TCCTAATGCAGTGATGCAGTCTGGTGGGCATTACATGCAGCACCAGCAGGCACAGCAACAAG
TGACTCCTCAGTCTCTGATGGCAGCTAGATCTTCCATGCTGTATTCTCAGCAGCCGATGGCT
GCTTTGCATCAAGCTCAGCAACAACAGCAGCAGCAGCATCAGCAGCAACAACAATCTCTTCA
CAGCCAGCTTGGCATAAATTCTGGAGGAAGCAGTGGATTGCATATGTTGCATGGTGAGACAA
ACATGGGATGTAATGGGCCTCTCTCATCTGGGGGCTTCCCTGAATTTGGGCGTGGGTCTGCT
ACCTCTGCTGAAGGTATGCAGGCCAACAGGGGCTTCACTATAGATCGTGGTTCAAATAAGCA
GGATGGAGTAGGATCAGAGAATGCCCATCCAGGTGCTGGTGATGGAAGAGGGAGTTCAACTG
GAGGGCAGAATGCAGATGAGTCAGAACCATCATACCTGAAAGCCTCCGAAGAAGAAGGAAAC
TAG

SEQ ID NO : 66 *Picea sitchensis* SYT1 translated amino acid sequence

MQQHLMQMQPMMAAYASNNITTDHIQKYLDENKQLILAILDNQNLGKLNECAQYQAKLQQNL
MYLAAIADSQPQAQTAHAQIPPNAVMQSGGHYMQHQQAQQQVTPQSLMAARSSMLYSQQPMA
ALHQAQQQQQQHQQQQQSLHSQLGINSGGSSGLHMLHGETNMGCNGPLSSGGFPEFGRGSA
TSAEGMQANRGFTIDRGSNKQDGVGSENAHPGAGDGRGSSTGGQNADESEPSYLKASEEEGN

FIGURE 8 (continued)

SEQ ID NO : 67 *Pinus taeda* SYT1 cDNA DT625916

ATGCAGCAGCACCTCATGCAAATGCAGCCCATGATGGCGGCCTACGCCTCCAACAATATCAC
CACTGATCACATCCAGAAGTACCTGGATGAGAACAAGCAGTTGATTCTGGCAATTTTGGACA
ACCAAAATCTCGGAAAGCTCAATGAGTGTGCTCAATACCAAGCAAAACTTCAGCAGAATTTG
ATGTATCTGGCTGCTATTGCTGATTCTCAACCTCAAGCACAAACTGCACATGCTCAGATTCC
TCCAAATGCGGTGATGCAGTCTGGTGGGCATTACATGCAGCATCAACAGGCACAGCAACAAG
TTACTCCTCAGTCTCTGATGGCAGCTAGATCTTCCATACTGTATGCTCAGCAACAACAGCAG
CAGCAGCATCAGCAGCATCAGCAGCAACAGCAGCAACAACAGTCTCTTCACAGCCAGCTTGG
CATAAATTCTGGAGGAAGCAGCGGTTTGCATATGTTGCATGGTGAGACAAACATGGGATGTA
ATGGGCCTCTGTCATCTGGGGGATTCCCTGAATTTGGGCGTGGGTCTGCTACCTCTGCTGAT
GGTATGCAGGTGAACAGGGGCTTTGCTATAGATCGTGGTTCAAACAAGCAGGATGGAGTTGG
ATCAGAGAATGCCCATGCTGGTGCTGGTGATGGAAGAGGGAGTTCAACTGGAGGGCAGAATG
CAGATGAGTCAGAACCATCATACCTGAAGGCCTCCGAGGAAGAAGGAAACTAG

SEQ ID NO : 68 *Pinus taeda* SYT1 translated amino acid sequence

MQQHLMQMQPMMAAYASNNITTDHIQKYLDENKQLILAILDNQNLGKLNECAQYQAKLQQNL
MYLAAIADSQPQAQTAHAQIPPNAVMQSGGHYMQHQQAQQQVTPQSLMAARSSILYAQQQQQ
QQHQQHQQQQQQQQSLHSQLGINSGGSSGLHMLHGETNMGCNGPLSSGGFPEFGRGSATSAD
GMQVNRGFAIDRGSNKQDGVGSENAHAGAGDGRGSSTGGQNADESEPSYLKASEEEGN

SEQ ID NO : 69 *Populus tremula* SYT1 cDNA DT476906

ATGCAACAGCACCTGATGCAGATGCAGCCCATGATGGCAGCCTATTACCCCAGCAACGTCAC
TACTGATCATATTCAACAGTATCTGGACGAAAACAAGTCATTGATTTTGAAGATTGTTGAGA
GCCAGAATTCAGGGAAACTCAGTGAGTGTGCAGAGAACCAAGCAAGACTGCAACAAAATCTC
ATGTACTTGGCTGCAATTGCTGATTGTCAGCCCCAACCACCTACCATGCATGCCCAGTTCCC
TTCCAGCGGCATTATGCAGCCAGGAGCACATTACATGCAGCATCAACAAGCTCAACAGATGA
CACCACAAGCCCTTATGGCTGCACGCTCTTCTATGCTGCAGTATGCTCAACAGCCATTCTCA
GCGCTTCAACAACAGCAAGCCTTACACAGCCAGCTCGGCATGAGCTCTGGTGGAAGCGCAGG
ACTTCATATGATGCAAAGCGAGGCTAACACTGCAGGAGGCAGTGGAGCTCTTGGTGCTGGAC
GATTTCCTGATTTTGGCATGGATGCCTCCAGTAGAGGAATCGCAAGTGGGAGCAAGCAAGAT
ATTCGGAGTGCAGGGTCTAGTGAAGGGCGAGGAGGAAGCTCTGGAGGCCAGGGTGGTGATGG
AGGTGAAACCCTTTACTTGAAATCTGCTGATGATGGGAACTGA

SEQ ID NO : 70 *Populus tremula* translated amino acid sequence

MQQHLMQMQPMMAAYYPSNVTTDHIQQYLDENKSLILKIVESQNSGKLSECAENQARLQQNL
MYLAAIADCQPQPPTMHAQFPSSGIMQPGAHYMQHQQAQQMTPQALMAARSSMLQYAQQPFS
ALQQQQALHSQLGMSSGGSAGLHMMQSEANTAGGSGALGAGRFPDFGMDASSRGIASGSKQD
IRSAGSSEGRGGSSGGQGGDGGETLYLKSADDGN

FIGURE 8 (continued)

SEQ ID NO : 71 *Saccharum officinarum* SYT1 cDNA CA078249.1
CA078630 CA082679 CA234526 CA239244 CA083312

ATGCAGCAGCAACACCTGATGCAGATGAACCAGAACATGATTGGGGGCTACACCTCTCCTGC
CGCTGTGACAACCGATCTCATCCAGCAGTACCTGGATGAGAACAAGCAGCTGATCCTGGCCA
TCCTCGACAACCAGAACAATGGCAAGGTGGAGGAGTGCGAACGGCACCAAGCTAAGCTCCAG
CACAACCTCATGTACCTGGCCGCCATCGCCGACAGCCAGCCACCACAGACTGCACCACTATC
ACAATACCCGTCCAACCTGATGATGCAGCCGGGCCCTCGGTACATGCCACCGCAGTCCGGGC
AGATGATGAGCCCGCAGTCGCTAATGGCGGCGCGGTCCTCCATGATGTACGCGCACCCGTCC
ATGTCACCACTCCAGCAGCAGCAGGCAGCGCACGGGCAGCTGGGCATGGCTTCAGGGGGCGG
CGGTGGCACGACCAGTGGGTTCAACATCCTCCATGGCGAGGCCAGTATGGGCGGTGCTGGTG
GCGCTTGTGCCGGCAACAACATGATGAACGCCGGCATGTTCTCAGGCTTTGGCCGCAGCGGC
AGTGGCGCCAAGGAGGGATCGACCTCGCTGTCGGTTGACGTCCGTGGTGGCACCAGCTCCGG
CGCGCAAAGCGGGGACGGCGAGTACCTGAAAGCAGGCACCGAGGAAGAAGGCAGTTAA

SEQ ID NO : 72 *Saccharum officinarum* SYT1 translated amino acid sequence

MQQQHLMQMNQNMIGGYTSPAAVTTDLIQQYLDENKQLILAILDNQNNGKVEECERHQAKLQ
HNLMYLAAIADSQPPQTAPLSQYPSNLMMQPGPRYMPPQSGQMMSPQSLMAARSSMMYAHPS
MSPLQQQQAAHGQLGMASGGGGGTTSGFNILHGEASMGGAGGACAGNNMMNAGMFSGFGRSG
SGAKEGSTSLSVDVRGGTSSGAQSGDGEYLKAGTEEEGS

SEQ ID NO : 73 *Saccharum officinarum* SYT2 cDNA CA110367

ATGCAGCAGCCGATGCCCATGCAGCCGCAGGCGCCGGAGATGACCCCGGCCGCCGGAATCAC
CACGGAGCAGATCCAAAAGTATCTGGATGAGAATAAGCAGCTTATTTTGGCTATTTTGGAAA
ATCAGAACCTAGGAAAATTGGCAGAATGTGCTCAGTATCAATCACAACTTCAGAAGAACCTC
TTGTATCTCGCTGCAATCGCAGATGCCCAACCACAGACTGCTGTAAGCCGCCCTCAGATGGC
GCCGCCTGGTGCATTGCCTGGAGTAGGGCAGTACATGTCACAGGTGCCTATGTTCCCACCGA
GGACACCTCTAACACCCCAGCAGATGCAGGAGCAGCAACTTCAGCAGCAGCAGGCTCAGCTG
CTAAATTTCAGTGGCCTAATGGTTGCTAGACCTGGCATGGTCAACGGCATGCCTCAGTCCAT
TCAAGTTCAGCAAGCTCAGCCACCACCAGCAGGGAACAAACAGGATGCTGGTGGGGTCGCCT
CGGAGCCCTCGGGCATTGAGAACCACAGGAGCACTGGTGGTGATAATGATGGTGGAAGCGAC
TAG

SEQ ID NO : 74 *Saccharum officinarum* SYT2 translated amino acid sequence

MQQPMPMQPQAPEMTPAAGITTEQIQKYLDENKQLILAILENQNLGKLAECAQYQSQLQKNL
LYLAAIADAQPQTAVSRPQMAPPGALPGVGQYMSQVPMFPPRTPLTPQQMQEQQLQQQQAQL
LNFSGLMVARPGMVNGMPQSIQVQQAQPPPAGNKQDAGGVASEPSGIENHRSTGGDNDGGSD

FIGURE 8 (continued)

SEQ ID NO : 75 *Saccharum officinarum* SYT3 cDNA CA161933.1 CA265085

ATGCAGCAGCAGATGCCCATGCCGCCGGCGCCCGCTGCGGCGGCGGCGCCCCGGCGGCCGG
CATCACCACCGAGCAGATCCAAAAGTATTTGGACGAAAATAAGCAACTTATTTTGGCCATCC
TGGAAAATCAGAACTTAGGAAAGTTGGCTGAATGTGCTCAGTATCAAGCTCAACTTCAAAAG
AACCTCTTGTACCTGGCTGCGATTGCTGATGCCCAACCCCAGCCACCACAAAACCCTGCAGG
TCGCCCTCAGATGATGCAACCTGGTATAGTGCCAGGTGCGGGGCATTACATGTCACAAGTAC
CAATGTTCCCTCCAAGAACTCCATTAACCCCACAGCAGATGCAAGAGCAGCAGCAGCAACAG
CTTCAGCAGCAGCAAGCGCAGGCTCTTACATTCCCTGGACAGATGGTCATGAGACCAGCTAC
CATCAACGGCATACAGCAGCCTATGCAAGCTGACCCTGCCCGGGCAGCGGAGCTGCAACAAC
CACCACCTATCCCAGCTGACGGGCGAGTAAGCAAGCAGCAGGACACAACGGCTGGCGTGAGC
TCAGAGCCTTCTGCCAATGAGAGCCACAAGACCACAACTGGAGCAGATAGTGAGGCAGGTGG
TGACGTGGCGGAGAAATCCTAA

SEQ ID NO : 76 *Saccharum officinarum* SYT3 translated amino acid sequence

MQQQMPMPPAPAAAAAPPAAGITTEQIQKYLDENKQLILAILENQNLGKLAECAQYQAQLQK
NLLYLAAIADAQPQPPQNPAGRPQMMQPGIVPGAGHYMSQVPMFPPRTPLTPQQMQEQQQQQ
LQQQQAQALTFPGQMVMRPATINGIQQPMQADPARAAELQQPPPIPADGRVSKQQDTTAGVS
SEPSANESHKTTTGADSEAGGDVAEKS

SEQ ID NO : 77 *Solanum tuberosum* SYT1 cDNA CK265597

ATGCAGCAGCACCTGATGCAGATGCAGCCCATGATGGCAGCTTACTATCCAACGAACGTCAC
TACTGACCATATTCAACAGTATTTGGATGAGAACAAATCACTCATTCTGAAAATTGTTGAGA
GCCAAAACTCGGGAAAACTCAGTGAATGTGCAGAGAACCAAGCTAGGCTTCAGAGGAATCTG
ATGTACCTTGCTGCTATTGCTGATTCACAACCTCAGCCTTCTAGCATGCATTCTCAGTTCTC
TTCTGGTGGGATGATGCAGCCAGGGACACACAGTTACCTGCAGCAGCAGCAGCAGCAACAAC
AAGCGCAACAAATGGCAACACAACAACTCATGGCTGCAAGATCCTCATCAATGCTCTATGGA
CAACAACAGCAGCAGCAGCAGTCTCAGTTATCACAATTTCAACAAGGCTTGCATAGTAG
CCAACTTGGCATGAGTTCTGGCAGTGGTGGAAGCACTGGACTTCATCACATGCTTCAAAGTG
AATCATCACCTCATGGTGGTGGTTTCTCTCATGACTTCGGCCGTGCAAATAAGCAAGACATT
GGGAGTAGTATGTCTGCTGAAGGGCGCGGCGGAAGCTCAGGTGGTGATGGTGGTGAGAATCT
TTATCTGAAAGCTTCTGAGGATTGA

SEQ ID NO : 78 *Solanum tuberosum* SYT1 translated amino acid sequence

MQQHLMQMQPMMAAYYPTNVTTDHIQQYLDENKSLILKIVESQNSGKLSECAENQARLQRNL
MYLAAIADSQPQPSSMHSQFSSGGMMQPGTHSYLQQQQQQQQAQQMATQQLMAARSSSMLYG
QQQQQQQQSQLSQFQQGLHSSQLGMSSGSGGSTGLHHMLQSESSPHGGGFSHDFGRANKQDI
GSSMSAEGRGGSSGGDGGENLYLKASED

FIGURE 8 (continued)

SEQ ID NO : 79 *Sorghum bicolor* SYT3 cDNA CX611128

ATGCAGCAGCAGATGCCCATGCCGCCGGCGCCCGCTGCGGCGGCGGCGACGGCGCCCCGGC
GGCCGGCATCACCACCGAGCAGATCCAGAAGTATTTGGACGAAAATAAGCAACTTATTTTGG
CCATCCTAGAAAATCAGAACTTAGGAAAGTTGGCTGAATGTGCTCAGTATCAAGCTCAACTT
CAAAAGAACCTCTTGTACCTGGCTGCGATTGCTGATGCCCAACCCCGACCACCGCAAAACCC
TGCAGGTCGCCCTCAGATGATGCAACCTGGTATAGTGCCAGGTGCAGGGCATTACATGTCAC
AAGTACCAATGTTCCCTCCAAGAACTCCATTAACCCCACAGCAAATGCAAGAGCAGCAGCAG
CAACAGCTTCAGCAGCAGCAAGCGCAGGCTCTTGCATTCCCTGGGCAGATGGTCATGAGACC
AGCTACCATCAACGGCATGCAGCAGCCTATGCAGGCTGACCCTGCCCGGGCAGCGGAGCTGC
AACAGCCAGCATCTGTCCCAGCCGACGGGCGAGTAAGCAAGCAGGACACAGCGGCTGGGGTG
AGCTCAGAGCCTTCTGCCAATGAGAGCCACAAGACCACAACCGGAGCAGATAGTGAGGCAGG
TGGAGACGTGGCGGAGAAATCCTAA

SEQ ID NO : 80 *Sorghum bicolor* SYT3 translated amino acid sequence

MQQQMPMPPAPAAAAATAPPAAGITTEQIQKYLDENKQLILAILENQNLGKLAECAQYQAQL
QKNLLYLAAIADAQPRPPQNPAGRPQMMQPGIVPGAGHYMSQVPMFPPRTPLTPQQMQEQQQ
QQLQQQQAQALAFPGQMVMRPATINGMQQPMQADPARAAELQQPASVPADGRVSKQDTAAGV
SSEPSANESHKTTTGADSEAGGDVAEKS

SEQ ID NO : 81 *Triticum aestivum* SYT2 cDNA CD901951

ATGCAGCAAGCGATGCCCATGCCGCCGGCGGCGGCGGCGCCGGGGATGCCTCCGTCTGCTGG
CCTCAGCACCGAGCAGATCCAAAAGTACCTGGATGAAAATAAGCAACTAATTTTGGCTATCT
TGGAAAATCAGAACCTGGGAAAGTTGGCGGAATGTGCTCAGTATCAAGCTCAGCTTCAGAAG
AATCTTTTGTATTTGGCTGCAATCGCTGATACTCAGCCACAGACCACTGTAAGCCGTCCTCA
GATGGCACCACCTAGTGCATCCCCAGGGGCAGGGCATTACATGTCACAGGTGCCAATGTTCC
CTCCGAGGACCCCTCTAACGCCTCAGCAGATGCAGGAGCAGCAACTACAGCAGCAACAGGCT
CAGATGCTTCCGTTTGCTGGTCAAATGGTTGCGAGACCTGGGGCTGTCAATGGCATGCCTCA
GGCCCCTCAAGTTGAACCAGCCTATGCAGCAGGTGGGGCCAGTTCTGAGCCTTCTGGCACTG
AGAGCCACAGGAGCACTGGTGCCGATAATGACGGGGGGAGCGGCTGGGCTGATCAGTCCTAA

SEQ ID NO : 82 *Triticum aestivum* SYT2 translated amino acid sequence

MQQAMPMPPAAAAPGMPPSAGLSTEQIQKYLDENKQLILAILENQNLGKLAECAQYQAQLQK
NLLYLAAIADTQPQTTVSRPQMAPPSASPGAGHYMSQVPMFPPRTPLTPQQMQEQQLQQQQA
QMLPFAGQMVARPGAVNGMPQAPQVEPAYAAGGASSEPSGTESHRSTGADNDGGSGWADQS

FIGURE 8 (continued)

SEQ ID NO : 83 *Triticum aestivum* SYT3 cDNA BJ246754 BJ252709

ATGCAGCAGGCGATGTCCTTGCCCCCGGGAGCGGTCGGCGCGGTGTCCTCGCCGGCCGGCAT
CACCACCGAGCAGATCCAAAAGTATTTGGATGAAAATAAGCAACTTATTTTGGCCATCCTTG
AAAATCAGAACCTAGGAAAGTTGGCTGAATGTGCTCAGTATCAAGCTCAACTCCAAAAGAAT
CTCTTGTATCTAGCTGCTATCGCGGATGCCCAACCACCACAGAACCCTACAAGTCACCCTCA
GATGGTGCAGCCTGGTAGTATGCAAGGTGCAGGGCATTACATGTCACAAGTACCAATGTTCC
CTCCAAGAACGCCTTTAACCCCACAGCAGATGCAAGAGCAGCAGCACCAGCAGCTTCAGCAG
CAGCAAGCCCAGGCCCTTTCTTTCCCCGCCCAGGTGGTCATGAGACCAGGCACCGTCAACGG
CATGCAGCAGCCTATGCAAGCAGCCGGCGACCTCCAGCCAGCAGCAGCACCTGGAGGGAGCA
AGCAGGACGCCGCAGTGGCTGGGGCCAGCTCGGAACCATCTGGCACCAAGAGCCACAAGAAC
GCGGGAGCAGAGGAGGTGGGCGCTGATGTAGCAGAACAATCCTAA

SEQ ID NO : 84 *Triticum aestivum* SYT3 translated amino acid sequence

MQQAMSLPPGAVGAVSSPAGITTEQIQKYLDENKQLILAILENQNLGKLAECAQYQAQLQKN
LLYLAAIADAQPPQNPTSHPQMVQPGSMQGAGHYMSQVPMFPPRTPLTPQQMQEQQHQQLQQ
QQAQALSFPAQVVMRPGTVNGMQQPMQAAGDLQPAAAPGGSKQDAAVAGASSEPSGTKSHKN
AGAEEVGADVAEQS

SEQ ID NO : 85 *Vitis vinifera* SYT1 cDNA DV219834

ATGCAGCAGCACCTGATGCAGATGCAGCCCATGATGGCAGCCTATTACCCCAGCAACGTCAC
CACTGATCACATTCAGCAGTATCTTGATGAAAACAAGTCATTGATTCTGAAGATTGTTGAGA
GCCAGAATTCAGGAAAATTGACTGAATGTGCAGAGAACCAGGCAAGACTACAGAGAAACCTC
ATGTACCTGGCTGCAATTGCTGATTCTCAACCCCAACCACCCACCATGCATGCTCAGTTCCC
TCCTAGTGGCATTGTTCAGCCAGGAGCTCACTACATGCAACACCAACAAGCTCAACAAATGA
CACCACAGTCGCTCCTGGCTGCACGCTCCTCCATGCTGTACACCCAACAACCATTTTCGGCC
CTGCAACAACAACAAGCCATCCATAGCCAGCTTGGCATGGGCTCTGGTGGAAGTGCAGGACT
TCACATGCTGCAAAGCGAGGGGAGTAATCCAGGAGGCAATGGAACACTGGGGACTGGTGGGT
TTCCTGATTTCAGCCGTGGAACTTCTGGAGAAGGCCTGCAGGCTGCAGGCAGGGGAATGGCT
GGTGGGAGCAAGCAAGATATGGGAAATGCAGAAGGGCGAGGAGGGAACTCAGGAGGTCAGGG
TGGGGATGGAGGTGAGACTCTTTACTTGAAAGCTGCTGAAGATGGGAATTGA

SEQ ID NO : 86 *Vitis vinifera* SYT1 translated amino acid sequence

MQQHLMQMQPMMAAYYPSNVTTDHIQQYLDENKSLILKIVESQNSGKLTECAENQARLQRNL
MYLAAIADSQPQPPTMHAQFPPSGIVQPGAHYMQHQQAQQMTPQSLLAARSSMLYTQQPFSA
LQQQQAIHSQLGMGSGGSAGLHMLQSEGSNPGGNGTLGTGGFPDFSRGTSGEGLQAAGRGMA
GGSKQDMGNAEGRGGNSGGQGGDGGETLYLKAAEDGN

SEQ ID NO : 87 Zea mays SYT3 cDNA CO468901

ATGCAGCAGCAGATGCCCATGCCGCCGGCGCCCGCTGCCGCCGCGGCGGCGGCGCCCCGGC
GGCAGGCATCACTACCGAGCAGATCCAGAAGTATTTGGACGAAAATAAGCAACTTATTTTGG
CCATCCTGGAAAATCAGAACTTAGGGAAGTTGGCTGAATGTGCTCAGTATCAAGCTCAACTT
CAAAAGAACCTCTTGTACCTGGCTGCGATTGCTGATGCCCAACCCCAGCCTCCGCAAAACCC
TGCAGGTCGCCCTCAGATGATGCAGCCTGGTATAGTGCCAGGTGCGGGGCATTACATGTCAC
AAGTACCAATGTTCCCTCCAAGAACCCCATTAACCCCACAGCAGATGCAGGAGCAGCAGCAA
CAACAACAGTTTCAGCAGCAGCAGCAGCAAGTGCAGGCTCTTACATTTCCTGGACAGATGGT
CATGAGACCAGGCACCATCAACGGCATGCAGCAGCAGCAGCCTATGCAGGCTGACCCTGCCC
GGGCAGCAGCGGAGCTGCAGCAGGCAGCACCTATCCCAGCTGACGGGCGAGGAAGCAAGCAG
GACACCGCGGGTGGGGCGAGCTCAGAGCCTTCTGCCAATGAGAGCCACAAGAGCGCCACCGG
AGCAGATACCGAGGCAGGTGGCGACGTGGCCGAGAAATCCTAA

SEQ ID NO : 88 Zea mays SYT3 translated amino acid sequence

MQQQMPMPPAPAAAAAAAPPAAGITTEQIQKYLDENKQLILAILENQNLGKLAECAQYQAQL
QKNLLYLAAIADAQPQPPQNPAGRPQMMQPGIVPGAGHYMSQVPMFPPRTPLTPQQMQEQQQ
QQQFQQQQQQVQALTFPGQMVMRPGTINGMQQQQPMQADPARAAAELQQAAPIPADGRGSKQ
DTAGGASSEPSANESHKSATGADTEAGGDVAEKS

SEQ ID NO : 89 Oryza sativa GOS2 promoter PRO0129

AATCCGAAAAGTTTCTGCACCGTTTTCACCCCCTAACTAACAATATAGGGAACGTGTGCTAA
ATATAAAATGAGACCTTATATATGTAGCGCTGATAACTAGAACTATGCAAGAAAAACTCATC
CACCTACTTTAGTGGCAATCGGGCTAAATAAAAAGAGTCGCTACACTAGTTTCGTTTTCCT
TAGTAATTAAGTGGGAAAATGAAATCATTATTGCTTAGAATATACGTTCACATCTCTGTCAT
GAAGTTAAATTATTCGAGGTAGCCATAATTGTCATCAAACTCTTCTTGAATAAAAAAATCTT
TCTAGCTGAACTCAATGGGTAAAGAGAGAGATTTTTTTAAAAAAATAGAATGAAGATATTC
TGAACGTATTGGCAAAGATTTAAACATATAATTATATAATTTTATAGTTTGTGCATTCGTCA
TATCGCACATCATTAAGGACATGTCTTACTCCATCCCAATTTTTATTTAGTAATTAAAGACA
ATTGACTTATTTTTATTATTTATCTTTTTTCGATTAGATGCAAGGTACTTACGCACACACTT
TGTGCTCATGTGCATGTGTGAGTGCACCTCCTAATACACGTTCAACTAGCAACACATCTCT
AATATCACTCGCCTATTTAATACATTTAGGTAGCAATATCTGAATTCAAGCACTCCACCATC
ACCAGACCACTTTTAATAATATCTAAAATACAAAAAATAATTTTACAGAATAGCATGAAAAG
TATGAAACGAACTATTTAGGTTTTTCACATACAAAAAAAAAAAGAATTTTGCTCGTGCGCGA
GCGCCAATCTCCCATATTGGGCACACAGGCAACAACAGAGTGGCTGCCCACAGAACAACCCA
CAAAAAACGATGATCTAACGGAGGACAGCAAGTCCGCAACAACCTTTTAACAGCAGGCTTTG
CGGCCAGGAGAGAGGAGGAGAGGCAAAGAAAACCAAGCATCCTCCTCCTCCCATCTATAAAT
TCCTCCCCCCTTTTCCCCTCTCTATATAGGAGGCATCCAAGCCAAGAAGAGGGAGAGCACCA
AGGACACGCGACTAGCAGAAGCCGAGCGACCGCCTTCTTCGATCCATATCTTCCGGTCGAGT
TCTTGGTCGATCTCTTCCCTCCTCCACCTCCTCCTCACAGGGTATGTGCCCTTCGGTTGTTC
TTGGATTTATTGTTCTAGGTTGTGTAGTACGGGCGTTGATGTTAGGAAAGGGGATCTGTATC
TGTGATGATTCCTGTTCTTGGATTTGGGATAGAGGGGTTCTTGATGTTGCATGTTATCGGTT
CGGTTTGATTAGTAGTATGGTTTTCAATCGTCTGGAGAGCTCTATGGAAATGAAATGGTTTA
GGGTACGGAATCTTGCGATTTTGTGAGTACCTTTTGTTTGAGGTAAAATCAGAGCACCGGTG

FIGURE 8 (continued)

ATTTTGCTTGGTGTAATAAAAGTACGGTTGTTTGGTCCTCGATTCTGGTAGTGATGCTTCTC
GATTTGACGAAGCTATCCTTTGTTTATTCCCTATTGAACAAAAATAATCCAACTTTGAAGAC
GGTCCCGTTGATGAGATTGAATGATTGATTCTTAAGCCTGTCCAAAATTTCGCAGCTGGCTT
GTTTAGATACAGTAGTCCCCATCACGAAATTCATGGAAACAGTTATAATCCTCAGGAACAGG
GGATTCCCTGTTCTTCCGATTTGCTTTAGTCCCAGAATTTTTTTCCCAAATATCTTAAAAA
GTCACTTTCTGGTTCAGTTCAATGAATTGATTGCTACAAATAATGCTTTTATAGCGTTATCC
TAGCTGTAGTTCAGTTAATAGGTAATACCCCTATAGTTTAGTCAGGAGAAGAACTTATCCGA
TTTCTGATCTCCATTTTTAATTATATGAAATGAACTGTAGCATAAGCAGTATTCATTTGGAT
TATTTTTTTATTAGCTCTCACCCCTTCATTATTCTGAGCTGAAAGTCTGGCATGAACTGTC
CTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAA
TCGGGATAGTTATACTGCTTGTTCTTATGATTCATTTCCTTTGTGCAGTTCTTGGTGTAGCT
TGCCACTTTCACCAGCAAAGTTC

SEQ ID NO : 90 Box I

IQ(Q/K)(Y/M/F/H)L(D/E)(E/D)N(K/N)XLI

Where X is any amino acid

SEQ ID NO : 91 Box II

NL(M/L/V)YLA(A/T)IAD

SEQ ID NO : 92 prm06681

GGGGACAAGTTTGTACAAAAAAGCAGGCTTAAACAATGCAACAGCACCTGATG

SEQ ID NO : 93 Prm06682

GGGGACCACTTTGTACAAGAAAGCTGGGTCATCATTAAGATTCCTTGTGC

SEQ ID NO : 94 prm06685

GGGGACAAGTTTGTACAAAAAAGCAGGCTTAAACAATGCAGCAGCAGCAGTCT

SEQ ID NO : 95 prm06686

GGGGACCACTTTGTACAAGAAAGCTGGGTTCTTTGGATCCTTTTCACTTG

SEQ ID NO : 96 prm06683

GGGGACAAGTTTGTACAAAAAAGCAGGCTTAAACAATGCAGCAATCTCCACAGAT

SEQ ID NO : 97 prm06684

GGGGACCACTTTGTACAAGAAAGCTGGGTTCCTCTATTTCATTTTCCTTCAG

PLANTS HAVING INCREASED YIELD AND A METHOD FOR MAKING THE SAME

RELATED APPLICATIONS

This application is a national stage application (under 35 U.S.C. 371) of PCT/EP2006/050489 filed Jan. 27, 2006, which claims benefit of European application 05100537.9 filed Jan. 27, 2005, U.S. Provisional Application 60/649,041 filed Feb. 1, 2005, and U.S. Provisional Application 60/730,403 filed Oct. 26, 2005.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 3rd_Revised_Sequence_Listing_14546_0021_US. The size of the text file is 138 KB, and the text file was created on Dec. 13, 2011.

The present invention relates generally to the field of molecular biology and concerns a method for increasing plant yield relative to corresponding wild type plants. More specifically, the present invention concerns a method for increasing plant yield comprising modulating expression in a plant of a nucleic acid encoding a synovial sarcoma translocation (SYT) polypeptide or a homologue thereof. The present invention also concerns plants having modulated expression of a nucleic acid encoding a SYT polypeptide or a homologue thereof, which plants have increased yield relative to corresponding wild type plants. The invention also provides constructs useful in the methods of the invention.

The ever-increasing world population and the dwindling supply of arable land available for agriculture fuels research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is yield, and in the case of many plants seed yield. Yield is normally defined as the measurable produce of economic value from a crop. This may be defined in terms of quantity and/or quality. Plant seeds are an important source of human and animal nutrition. Crops such as, corn, rice, wheat, canola and soybean account for over half of total human caloric intake, whether through direct consumption of the seeds themselves or through consumption of meat products raised on processed seeds. They are also a source of sugars, oils and many kinds of metabolites used in industrial processes. Seeds contain an embryo, the source of new shoots and roots after germination, and an endosperm, the source of nutrients for embryo growth, during germination and early growth of seedlings. The development of a seed involves many genes, and requires the transfer of metabolites from roots, leaves and stems into the growing seed. The endosperm, in particular, assimilates the metabolic precursors of carbohydrate polymers, oil and proteins and synthesizes them into storage macromolecules to fill out the grain. The ability to increase plant seed yield, whether through seed number, seed biomass, seed development, seed filling or any other seed-related trait would have many applications in agriculture, and even many non-agricultural uses such as in the biotechnological production of substances such as pharmaceuticals, antibodies or vaccines.

Yield may also depend on factors, such as the number and size of organs, plant architecture (for example, the number of branches), seed production and more. Root development, nutrient uptake and stress tolerance may also be important factors in determining yield. Optimizing these factors may therefore also contribute to increasing crop yield.

It has now been found that modulating expression in a plant of a nucleic acid encoding a SYT polypeptide or a homologue thereof gives plants having increased yield relative to corresponding wild type plants.

SYT is a transcriptional co-activator which, in plants, forms a functional complex with transcription activators of the GRF (growth-regulating factor) family of proteins (Kim H J, Kende H (2004) Proc Nat Acad Sc 101: 13374-9). SYT is also called GIF for GRF-interacting factor. The GRF transcription activators share structural domains (in the N-terminal region) with the SWI/SNF proteins of the chromatin-remodelling complexes in yeast (van der Knaap E et al. (2000) Plant Phys 122: 695-704). Transcriptional co-activators of these complexes are proposed to be involved in recruiting SWI/SNF complexes to enhancer and promoter regions to effect local chromatin remodelling (review Näär A M at al., (2001) Annu Rev Biochem 70: 475-501). The alteration in local chromatin structure modulates transcriptional activation. More precisely, SYT is proposed to interact with plant SWI/SNF complex to affect transcriptional activation of GRF target gene(s) (Kim H J, Kende H (2004) Proc Nat Acad Sc 101: 13374-9).

SYT belongs to a gene family of three members in Arabidopsis. The SYT polypeptide shares homology with the human SYT. The human SYT polypeptide was shown to be a transcriptional co-activator (Thaete at al. (1999) Hum Molec Genet 8: 585-591). Three domains characterize the mammalian SYT polypeptide:

(i) the N-terminal SNH (SYT N-terminal homology) domain, conserved in mammals, plants, nematodes and fish;

(ii) the C-terminal QPGY-rich domain, composed predominantly of glycine, proline, glutamine and tyrosine, occurring at variable intervals;

(iii) a methionine-rich (Met-rich) domain located between the two previous domains.

In plant SYT polypeptides, the SNH domain is well conserved. The C-terminal domain is rich in glycine and glutamine, but not in proline or tyrosine. It has therefore been named the QG-rich domain in contrast to the QPGY domain of mammals. As with mammalian SYT, a Met-rich domain may be identified N-terminally of the QG domain. The QG-rich domain may be taken to be substantially the C-terminal remainder of the protein (minus the SHN domain); the Met-rich domain is typically comprised within the first half of the QG-rich (from the N-terminus to the C-terminus). A second Met-rich domain may precede the SNH domain in plant SYT polypeptides (see FIG. 1).

A SYT loss of function mutant and transgenic plants with reduced expression of SYT was reported to develop small and narrow leaves and petals, which have fewer cells (Kim H J, Kende H (2004) Proc Nat Acad Sc 101: 13374-9).

According to the present invention, there is provided a method for increasing plant yield, comprising modulating expression in a plant of a nucleic acid encoding a SYT polypeptide or a homologue thereof.

Reference herein to "corresponding wild type plants" is taken to mean any suitable control plant or plants, the choice of which would be well within the capabilities of a person skilled in the art and may include, for example, corresponding wild type plants or corresponding plants without the gene of interest. A "control plant" as used herein refers not only to whole plants, but also to plant parts, including seeds and seed parts.

Advantageously, performance of the methods according to the present invention results in plants having increased yield, particularly seed yield, relative to corresponding wild type plants.

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part (such as fruits, nuts and pulses); (ii) increased total seed yield, which includes an increase in seed biomass (seed weight) and which may be an increase in the seed weight per plant or on an individual seed basis; (iii) increased number of (filled) seeds; (iv) increased seed size, which may also influence the composition of seeds; (v) increased seed volume, which may also influence the composition of seeds (including oil, protein and carbohydrate total content and composition); (vi) increased individual seed area; (vii) increased individual seed length or width; (viii) increased harvest index, which is expressed as a ratio of the yield of harvestable parts, such as seeds, over the total biomass; and (ix) increased thousand kernel weight (TKW), which is extrapolated from the number of filled seeds counted and their total weight. An increased TKW may result from an increased seed size and/or seed weight. An increased TKW may result from an increase in embryo size and/or endosperm size. An increase in seed size, seed volume, seed area, seed perimeter, seed width and seed length may be due to an increase in specific parts of a seed, for example due to an increase in the size of the embryo and/or endosperm and/or aleurone and/or scutellum, or other parts of a seed.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may be manifested by an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

An increase in yield may also result in modified architecture, or may occur as a result of modified architecture.

According to a preferred feature, performance of the methods of the invention result in plants having increased seed yield. Therefore, according to the present invention, there is provided a method for increasing seed yield in a plant, which method comprises modulating expression in a plant of a nucleic acid encoding a SYT polypeptide or a homologue thereof.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate relative to corresponding wild type plants. Therefore, according to the present invention, there is provided a method for increasing growth rate in plants, which method comprises modulating expression in a plant of a nucleic acid encoding a SYT polypeptide or a homologue thereof.

An increase in (seed) yield and/or growth rate occurs whether the plant is under non-stress conditions or whether the plant is exposed to various stresses compared to suitable control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Chemicals may also cause abiotic stresses. Biotic stresses are typically those stresses caused by pathogens, such as bacteria, viruses, fungi and insects.

Advantageously, yield may be modified in any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the transgene of interest. The term "plant" also encompasses plant cells, suspension cultures, callus tissue, embryos, meristematic regions, gametophytes, sporophytes, pollen and microspores, again wherein each of the aforementioned comprise the transgene.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp., *Areca catechu*, *Astelia trepans*, *Astragalus cicer*, *Baikieea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffee arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cyathea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissolute*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include amongst others soybean, sunflower, canola, alfalfa, rapeseed, cotton, tomato, potato or tobacco. *Arabidopsis thaliana* is generally not considered as a crop plant. Further preferably, the plant is a monocotyledonous plant, such as sugarcane. More preferably the plant is a cereal, such as rice, maize, wheat, barley, millet, rye, sorghum or oats.

The term "SYT polypeptide or homologue thereof" as defined herein refers to a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2; and (ii) a Met-rich domain; and (iii) a QG-rich domain.

Preferably, SNH domain having at least 40% identity to the SNH domain of SEQ ID NO: 2 comprises the residues shown in black in FIG. 2 (SEQ ID NO: 98). Further preferably, the SNH domain is represented by SEQ ID NO: 1.

Additionally, the SYT polypeptide or a homologue thereof may comprise one or more of the following: (a) SEQ ID NO: 90; (b) SEQ ID NO: 91; and (c) a Met-rich domain at the N-terminal preceding the SNH domain.

A SYT polypeptide or a homologue thereof typically interacts with GRF (growth-regulating factor) polypeptides in yeast two-hybrid systems. Yeast two-hybrid interaction assays are well known in the art (see Field et al. (1989) Nature 340(6230): 245-246). For example, the SYT polypeptide as represented by SEQ ID NO: 4 is capable of interacting with AtGRF5 and with AtGRF9. SYT polypeptide and homologues thereof have been demonstrated by the inventors to increase yield, particularly seed yield, in plants.

A SYT polypeptide or homologue thereof is encoded by a SYT nucleic acid/gene. Therefore the term "SYT nucleic acid/gene" as defined herein is any nucleic acid/gene encoding a SYT polypeptide or a homologue thereof as defined hereinabove.

SYT polypeptides or homologues thereof may readily be identified using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues of SYT comprising an SNH domain having at least 40% sequence identity to the SNH domain of SEQ ID NO: 2 and/or comprising SEQ ID NO: 90 and/or SEQ ID NO: 91, may readily be identified using, for example, the ClustalW multiple sequence alignment algorithm (version 1.83) available at clustalw.genome.jp/sit-bin/nph-clustalw, with the default pairwise alignment parameters, and a scoring method in percentage. A sequence having a 40% identity to the SNH domain of SEQ ID NO: 2 is sufficient to identify a sequence as being a SYT.

Furthermore, the presence of a Met-rich domain or a QG-rich domain may also readily be identified. As shown in FIG. 3, the Met-rich domain and QG-rich domain follows the SNH domain. The QG-rich domain may be taken to be substantially the C-terminal remainder of the protein (minus the SHN domain); the Met-rich domain is typically comprised within the first half of the QG-rich (from the N-term to the C-term). Primary amino acid composition (in %) to determine if a polypeptide domain is rich in specific amino acids may be calculated using software programs from the ExPASy server (Gasteiger E et al. (2003) ExPASy: the proteomics server for in-depth protein knowledge and analysis. Nucleic Acids Res 31:3784-3788), in particular the ProtParam tool. The composition of the protein of interest may then be compared to the average amino acid composition (in %) in the Swiss-Prot Protein Sequence data bank. Within this databank, the average Met (M) content is of 2.37%, the average Gln (Q) content is of 3.93% and the average Gly (G) content is of 6.93%. As defined herein, a Met-rich domain or a QG-rich domain has Met content (in %) or a Gln and Gly content (in %) above the average amino acid composition (in %) in the Swiss-Prot Protein Sequence data bank.

Examples of SYT polypeptide or homologues thereof include (encoded by polynucleotide sequence accession number in parenthesis; see also Table 1): *Arabidopsis thaliana* Arath_SYT1 (AY102639.1) SEQ ID NO: 4, *Arabidopsis thaliana* Arath_SYT2 (AY102640.1) SEQ ID NO: 6, *Arabidopsis thaliana* Arath_SYT3 (AY102641.1) SEQ ID NO: 8, *Aspergillus officinalis* Aspof_SYT (CV287542) SEQ ID NO: 10, *Brassica napus* Brana_SYT (CD823592) SEQ ID NO: 12, *Citrus sinensis* Citsi_SYT (CB290588) SEQ ID NO: 14, *Gossypium arboreum* Gosar_SYT (BM359324) SEQ ID NO: 16, *Medicago trunculata* Medtr_SYT (CA858507.1) SEQ ID NO: 18, *Oryza sativa* Orysa_SYT1 (AK058575) SEQ ID NO: 20, *Oryza sativa* Orysa_SYT2 (AK105366) SEQ ID NO: 22, *Oryza sativa* Orysa_SYT3 (BP185008) SEQ ID NO: 24, *Solanum tuberosum* Soltu_SYT (BG590990) SEQ ID NO: 26, *Zea mays* Zeama_SYT1 (BG874129.1, CA409022.1) SEQ ID NO: 28, *Zea mays* Zeama_SYT2 (AY106697) SEQ ID NO: 30, *Homo sapiens* Homsa_SYT (CAG46900) SEQ ID NO: 32, *Allium cepa* Allce_SYT2 (CF437-485) SEQ ID NO: 34, *Aquilegia formosa×Aquilegia pubescens* Aqufo_SYT1 (DT758802) SEQ ID NO: 36, *Brachypodium distachyon* Bradi_SYT3 (DV480064) SEQ ID NO: 38, *Brassica napus* Brana_SYT2 (CN732814) SEQ ID NO: 40, *Citrus sinensis* Citsi_SYT2 (CV717501) SEQ ID NO: 42, *Euphorbia esula* Eupes_SYT2 (DV144834) SEQ ID NO: 44, *Glycine max* Glyma_SYT2 (BQ612648) SEQ ID NO: 46, *Glycine soya* Glyso_SYT2 (CA799921) SEQ ID NO: 48, *Gossypium hirsutum* Goshi_SYT1 (DT558852) SEQ ID NO: 50, *Gossypium hirsutum* Goshi_SYT2 (DT563805) SEQ ID NO: 52, *Hordeum vulgate* Horvu_SYT2 (CA032350) SEQ ID NO: 54, *Lactuca serriola* Lacse_SYT2 (DW110765) SEQ ID NO: 56, *Lycopersicon esculentum* Lyces_SYT1 (AW934450, BP893155) SEQ ID NO: 58, *Malus domestica* Maldo_SYT2 (CV084230, DR997566) SEQ ID NO: 60, *Medicago trunculata* Medtr_SYT2 (CA858743, BI310799, AL382135) SEQ ID NO: 62, *Panicum virgatum* Panvi_SYT3 (DN152517) SEQ ID NO: 64, *Picea sitchensis* Picsi_SYT1 (DR484100, DR478-464) SEQ ID NO: 66, *Pinus taeda* Pinta_SYT1 (DT625916) SEQ ID NO: 68, *Populus tremula* Poptr_SYT1 (DT476906) SEQ ID NO: 70, *Saccharum officinarum* Sacof_SYT1 (CA078249, CA078630, CA082679, CA234526, CA239244, CA083312) SEQ ID NO: 72, *Saccharum officinarum.* Sacof_SYT2 (CA110367) SEQ ID NO: 74, *Saccharum officinarum* Sacof_SYT3 (CA161933, CA265085) SEQ ID NO: 76, *Solanum tuberosum* Soltu_SYT1 (CK265597) SEQ ID NO: 78, *Sorghum bicolor* Sorbi_SYT3 (CX611128) SEQ ID NO: 80, *Triticum aestivum* Triae_SYT2 (CD901951) SEQ ID NO: 82, *Triticum aestivum* Triae_SYT3 (BJ246754, BJ252709) SEQ ID NO: 84, *Vitis vinifera* Vitvi_SYT1 (DV219834) SEQ ID NO: 86, *Zea mays* Zeama_SYT3 (CO468901) SEQ ID NO: 88.

TABLE 1

Examples of SYT homologues

| Name | NCBI nucleotide accession number | Nucleotide SEQ ID NO | Translated polypeptide SEQ ID NO | Source |
|---|---|---|---|---|
| Arath_SYT1 | AY102639.1 | 3 | 4 | *Arabidopsis thaliana* |
| Arath_SYT2 | AY102640.1 | 5 | 6 | *Arabidopsis thaliana* |
| Arath_SYT3 | AY102641.1 | 7 | 8 | *Arabidopsis thaliana* |
| Aspof_SYT1 | CV287542 | 9 | 10 | *Aspergillus officinalis* |
| Brana_SYT1 | CD823592 | 11 | 12 | *Brassica napus* |
| Citsi_SYT1 | CB290588 | 13 | 14 | *Citrus sinensis* |
| Gosar_SYT1 | BM359324 | 15 | 16 | *Gossypium arboreum* |
| Medtr_SYT1 | CA858507.1 | 17 | 18 | *Medicago trunculata* |
| Orysa_SYT1 | AK058575 | 19 | 20 | *Oryza sativa* |
| Orysa_SYT2 | AK105366 | 21 | 22 | *Oryza sativa* |
| Orysa_SYT3 | BP185008 | 23 | 24 | *Oryza sativa* |
| Soltu_SYT2 | BG590990 | 25 | 26 | *Solanum tuberosum* |
| Zeama_SYT1 | BG874129.1 CA409022.1* | 27 | 28 | *Zea mays* |
| Zeama_SYT2 | AY106697 | 29 | 30 | *Zea mays* |
| Homsa_SYT | CR542103 | 31 | 32 | *Homo sapiens* |
| Allce_SYT2 | CF437485 | 33 | 34 | *Allium cepa* |
| Aqufo_SYT1 | DT758802.1 | 35 | 36 | *Aquilegia formosa × Aquilegia pubescens* |
| Bradi_SYT3 | DV480064.1 | 37 | 38 | *Brachypodium distachyon* |
| Brana_SYT2 | CN732814 | 39 | 40 | *Brassica napa* |
| Citsi_SYT2 | CV717501 | 41 | 42 | *Citrus sinensis* |
| Eupes_SYT2 | DV144834 | 43 | 44 | *Euphorbia esula* |
| Glyma_SYT2 | BQ612648 | 45 | 46 | *Glycine max* |
| Glyso_SYT2 | CA799921 | 47 | 48 | *Glycine soya* |
| Goshi_SYT1 | DT558852 | 49 | 50 | *Gossypium hirsutum* |

TABLE 1-continued

Examples of SYT homologues

| Name | NCBI nucleotide accession number | Nucleotide SEQ ID NO | Translated polypeptide SEQ ID NO | Source |
|---|---|---|---|---|
| Goshi_SYT2 | DT563805 | 51 | 52 | *Gossypium hirsutum* |
| Horvu_SYT2 | CA032350 | 53 | 54 | *Hordeum vulgare* |
| Lacse_SYT2 | DW110765 | 55 | 56 | *Lactuca serriola* |
| Lyces_SYT1 | AW934450.1 BP893155.1* | 57 | 58 | *Lycopersicon esculentum* |
| Maldo_SYT2 | CV084230 DR997566* | 59 | 60 | *Malus domestica* |
| Medtr_SYT2 | CA858743 BI310799.1 AL382135.1* | 61 | 62 | *Medicago trunculata* |
| Panvi_SYT3 | DN152517 | 63 | 64 | *Panicum virgatum* |
| Picsi_SYT1 | DR484100 DR478464.1 | 65 | 66 | *Picea sitchensis* |
| Pinta_SYT1 | DT625916 | 67 | 68 | *Pinus taeda* |
| Poptr_SYT1 | DT476906 | 69 | 70 | *Populus tremula* |
| Sacof_SYT1 | CA078249.1 CA078630 CA082679 CA234526 CA239244 CA083312* | 71 | 72 | *Sacchanan officinarum* |
| Sacof_SYT2 | CA110367 | 73 | 74 | *Saccharum officinarum* |
| Sacof_SYT3 | CA161933.1 CA265085* | 75 | 76 | *Sacchanan officinarum* |
| Soltu_SYT1 | CK265597 | 77 | 78 | *Solanum tuberosum* |
| Sorbi_SYT3 | CX611128 | 79 | 80 | *Sorghum bicolor* |
| Triae_SYT2 | CD901951 | 81 | 82 | *Triticum aestivum* |
| Triae_SYT3 | BJ246754 BJ252709* | 83 | 84 | *Triticum aestivum* |
| Vitvi_SYT1 | DV219834 | 85 | 86 | *Vitis vinifera* |
| Zeama_SYT3 | CO468901 | 87 | 88 | *Zea mays* |

*Compiled from cited accessions

It is to be understood that sequences falling under the definition of "SYT polypeptide or homologue thereof" are not to be limited to the sequences represented by SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, but that any polypeptide comprising from N-terminal to C-terminal: (i) an SNH domain having at least 40% sequence identity to the SNH domain of SEQ ID NO: 2; and (ii) a Met-rich domain; and (iii) a QG-rich domain may be suitable in performing the methods of the invention.

Examples of SYT nucleic acids include but are not limited to those represented by any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87. SYT nucleic acids/genes and variants thereof may be suitable in practicing the methods of the invention. Variant SYT nucleic acid/genes typically are those having the same function as a naturally occurring SYT nucleic acid/genes, which can be the same biological function or the function of increasing yield when expression of the nucleic acids/genes is modulated in a plant. Such variants include portions of a SYT nucleic acid/gene and/or nucleic acids capable of hybridising with a SYT nucleic acid/gene as defined below.

The term portion as defined herein refers to a piece of DNA encoding a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2 and (ii) a Met-rich domain; and (iii) a QG-rich domain. A portion may be prepared, for example, by making one or more deletions to a SYT nucleic acid. The portions may be used in isolated form or they may be fused to other coding (or non coding) sequences in order to, for example, produce a protein that combines several activities. When fused to other coding sequences, the resulting polypeptide produced upon translation may be bigger than that predicted for the SYT fragment. Preferably, the portion is a portion of a nucleic acid as represented by any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87. Most preferably the portion of a nucleic acid is as represented by SEQ ID NO: 3 SEQ ID NO: 5 or SED IQ NO: 7.

Another variant of a SYT nucleic acid/gene is a nucleic acid capable of hybridising under reduced stringency conditions, preferably under stringent conditions, with a SYT nucleic acid/gene as hereinbefore defined, which hybridising sequence encodes a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2 and (ii) a Met-rich domain; and (iii) a QG-rich domain. Preferably, the hybridising sequence is one that is capable of hybridising to a nucleic acid as represented by any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87 or to a portion of any of the aforementioned sequences as defined hereinabove. Most preferably the hybridizing sequence of a nucleic acid is as represented by SEQ ID NO: 3, SEQ ID NO: 5 or SEQ ID NO: 7.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1. DNA-DNA hybrids (Meinkoth and Wahl, Anal. Biochem., 138: 267-284, 1984):

$$T_m=81.5° C.+16.6\times\log[Na^+]^a+0.41\times\%[G/C^b]-500\times[L^c]^{-1}-0.61\times\% \text{ formamide}$$

2. DNA-RNA or RNA-RNA hybrids:

$$T_m=79.8+18.5(\log_{10}[Na^+]^a)+0.58(\% G/C^b)+11.8(\% G/C^b)^2-820/L^c$$

3. oligo-DNA or oligo-RNA$^d$ hybrids:
   For <20 nucleotides: $T_m=2(l_n)$
   For 20-35 nucleotides: $T_m=22+1.46(l_n)$ $^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonudeotide; $l_n$, effective length of primer=2×(no. of G/C)+(no. of A/T).

Note: for each 1% formamide, the $T_m$ is reduced by about 0.6 to 0.7° C., while the presence of 6 M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. Conditions of greater or less stringency may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with RNase. Examples of hybridisation and wash conditions are listed in Table 2 below.

TABLE 2

Examples of hybridisation and wash conditions

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | > or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C. 4 × SSC; or 45° C., 4 × SSC and 50% formamide | 65° C.; 1 × SSC |
| H | DNA:DNA | <50 | Th*; 4 × SSC | Th*; 4 × SSC |
| I | DNA:RNA | > or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | > or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | > or equal to 50 | 50° C. 4 × SSC; or 40° C., 6 × SSC and 50% formamide | 50° C.; 2 × SSC |
| N | DNA:DNA | <50 | Tn*; 6 × SSC | Tn*; 6 × SSC |
| O | DNA:RNA | > or equal to 50 | 55° C. 4 × SSC; or 42° C., 6 × SSC and 50% formamide | 55° C.; 2 × SSC |
| P | DNA:RNA | <50 | Tp*; 6 × SSC | Tp*; 6 × SSC |
| Q | RNA:RNA | > or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 × SSPE is 0.15M NaCl, 10 mM NaH$_2$PO$_4$, and 1.25 mM EDTA, pH 7.4) may be substituted for SSC (1 × SSC is 0.15M NaCl and 15 mM sodium citrate) in the hybridisation and wash buffers; washes are performed for 15 minutes after hybridisation is complete. The hybridisations and washes may additionally include 5x Denhardt's reagent, 0.5-1.0% SDS, 100 µg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature T$_m$ of the hybrids; the T$_m$ is determined according to the above-mentioned equations.
±The present invention also encompasses the substitution of any one, or more DNA or RNA hybrid partners with either a PNA, or a modified nucleic acid.

For the purposes of defining the level of stringency, reference can be made to Sambrook et al. (2001) Molecular Cloning: a laboratory manual, 3$^{rd}$ Edition Cold Spring Harbor Laboratory Press, CSH, New York or to Current Protocols in Molecular Biology, John Wiley & Sons, N.Y. (1989).

The SYT nucleic acid or variant thereof may be derived from any artificial source or natural source, such as plant, algae or animal. This nucleic acid may be modified from its native form in composition and/or genomic environment through deliberate human manipulation. The nucleic acid is preferably of plant origin, whether from the same plant species (for example to the one in which it is to be introduced) or whether from a different plant species. Preferably the nucleic acid of plant origin encodes a SYT1. Alternatively, the nucleic acid may encode a SYT2 or SYT3, which are closely related to one another on a polypeptide level. The nucleic acid may be isolated from a dicotyledonous species, preferably from the family Brassicaceae, further preferably from *Arabidopsis thaliana*. More preferably, the three SYT nucleic acids isolated from *Arabidopsis thaliana* are represented by SEQ ID NO: 3, SEQ ID NO: 5 and SEQ ID NO: 7, and the three SYT amino acid sequences are as represented by SEQ ID NO: 4, SEQ ID NO: 6 and SEQ ID NO: 8.

The expression of a nucleic acid encoding a SYT polypeptide or a homologue thereof may be modulated by introducing a genetic modification (preferably in the locus of a SYT gene). The locus of a gene as defined herein is taken to mean a genomic region, which includes the gene of interest and 10 kb up- or downstream of the coding region.

The genetic modification may be introduced, for example, by any one (or more) of the following methods: T-DNA activation, TILLING, site-directed mutagenesis, directed evolution and homologous recombination, or by introducing and expressing in a plant a nucleic acid encoding a SYT polypeptide or a homologue thereof. Following introduction of the genetic modification, there follows a step of selecting for modulated expression of a nucleic acid encoding a SYT polypeptide or a homologue thereof, which modulated expression gives plants having increased yield, particularly increased seed yield.

T-DNA activation tagging (Hayashi et al. Science (1992) 1350-1353) involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a SYT gene using the technique of TILLING (Targeted Induced Local Lesions In Genomes). This is a mutagenesis technology useful to generate and/or identify, and to eventually isolate mutagenised variants of a SYT nucleic acid encoding a protein with enhanced SYT activity. TILLING also allows selection of plants carrying such mutant variants. These mutant variants may even exhibit higher SYT activity than that exhibited by the gene in its natural form. TILLNG combines high-density mutagenesis with high-throughput screening methods. The steps typically followed in TILLING are: (a) EMS mutagenesis (Redei G P and Koncz C (1992) In Methods in Arabidopsis Research, Koncz C, Chua N H, Schell J, eds. Singapore, World Scientific Publishing Co, pp. 16-82; Feldmann et al., (1994) In Meyerowitz E M, Somerville C R, eds, Arabidopsis. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Site-directed mutagenesis may be used to generate variants of SYT nucleic acids. Several methods are available to achieve site-directed mutagenesis, the most common being PCR based methods (current protocols in molecular biology. Wiley Eds. at 4ulr.com/products/currentprotocols/index.html).

Directed evolution may also be used to generate variants of SYT nucleic acids. This consists of iterations of DNA shuffling followed by appropriate screening and/or selection to generate variants of SYT nucleic acids or portions thereof encoding SYT polypeptides or homologues or portions thereof having an modified biological activity (Castle et al., (2004) Science 304(5674): 1151-4; U.S. Pat. Nos. 5,811,238 and 6,395,547). T-DNA activation, TILLING, site-directed mutagenesis and directed evolution are examples of technologies that enable the generation of novel SYT alleles and variants.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada at al. (2002) Nat Biotech 20(10): 1030-4; Iida and Terada (2004) Curr Opin Biotech 15(2): 132-8). The nucleic acid to be targeted (which may be a SYT nucleic acid or variant thereof as hereinbefore defined) is targeted to the locus of a SYT gene. The nucleic acid to be targeted may be an improved allele used to replace the endogenous gene or may be introduced in addition to the endogenous gene.

A preferred method for introducing a genetic modification (which in this case need not be in the locus of a SYT gene) is to introduce and express in a plant a nucleic acid encoding a SYT polypeptide or a homologue thereof. A SYT polypeptide or a homologue thereof is defined as a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2; and (ii) a Met-rich domain; and (iii) a QG-rich domain.

Preferably, SNH domain having at least 40% identity to the SNH domain of SEQ ID NO: 2 comprises the residues shown in black in FIG. 2 (SEQ ID NO: 98). Further preferably, the SNH domain is represented by SEQ ID NO: 1.

The nucleic acid to be introduced into a plant may be a full-length nucleic acid or may be a portion or a hybridizing sequence as hereinbefore defined.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 3 below).

Homologues include orthologues and paralogues, which encompass evolutionary concepts used to describe ancestral relationships of genes. Paralogues are genes within the same species that have originated through duplication of an ancestral gene and orthologues are genes from different organisms that have originated through speciation.

Orthologues in, for example, monocot plant species may easily be found by performing a so-called reciprocal blast search. This may be done by a first blast involving blasting a query sequence (for example, SEQ ID NO: 3, SEQ ID NO: 4, SEQ ID NO: 5, SEQ ID NO: 6, SEQ ID NO: 7 or SEQ ID NO: 8) against any sequence database, such as the publicly available NCBI database which may be found at: ncbi.nlm.nih. gov. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 3, SEQ ID NO: 4, SEQ ID NO: 5, SEQ ID NO: 6, SEQ ID NO: 7 or SEQ ID NO: 8 the second blast would therefore be against *Arabidopsis* sequences). The results of the first and second BLASTs are then compared. A paralogue is identified if a high-ranking hit from the second blast is from the same species as from which the query sequence is derived; an orthologue is identified if a high-ranking hit is not from the same species as from which the query sequence is derived. High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions. Conservative substitution tables are readily available in the art. The table below gives examples of conserved amino acid substitutions.

TABLE 3

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The SYT polypeptide or homologue thereof may be a derivative. "Derivatives" include peptides, oligopeptides, polypeptides, proteins and enzymes which may comprise substitutions, deletions or additions of non-naturally occurring amino acid residues compared to the amino acid sequence of a naturally-occurring form of the protein, for example, as presented in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86 and SEQ ID NO: 88.

"Derivatives" of a protein encompass peptides, oligopeptides, polypeptides, proteins and enzymes which may comprise naturally occurring altered, glycosylated, acylated, prenylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The SYT polypeptide or homologue thereof may be encoded by an alternative splice variant of a SYT nucleic acid/gene. The term "alternative splice variant" as used herein encompasses variants of a nucleic acid sequence in which selected introns and/or exons have been excised, replaced or added, or in which introns have been shortened or lengthened. Such variants will be ones in which the biological activity of the protein is retained, which may be achieved by selectively retaining functional segments of the protein. Such splice variants may be found in nature or may be manmade. Methods for making such splice variants are well known in the art. Preferred splice variants are splice variants of the nucleic acid encoding a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2; and (ii) a Met-rich domain; and (iii) a QG-rich domain. Preferably, SNH domain having at least 40% identity to the SNH domain of SEQ ID NO: 2 comprises the residues shown in black in FIG. 2. Further preferably, the SNH domain is represented by SEQ ID NO: 1.

Additionally, the SYT polypeptide or a homologue thereof may comprise one or more of the following: (i) SEQ ID NO: 90; and/or (ii) SEQ ID NO: 91; and/or (iii) a Met-rich domain at the N-terminal preceding the SNH domain.

Further preferred are splice variants of nucleic acids represented by SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87. Most preferred are splice variants of a SYT nucleic acid/gene represented by SEQ ID NO: 3, SEQ ID NO: 5 and SEQ ID NO: 7.

The homologue may also be encoded by an allelic variant of a nucleic acid encoding a SYT polypeptide or a homologue thereof, preferably an allelic variant of the nucleic acid encoding a polypeptide comprising from N-terminal to C-terminal: (i) an SNH domain having in increasing order of preference at least 40%, 45%, 50%, 55%, 60%, 65%, 70%, 75%, 80%, 85%, 90%, 91%, 92%, 93%, 94%, 95%, 96%, 97%, 98%, 99% sequence identity to the SNH domain of SEQ ID NO: 2; and (ii) a Met-rich domain; and (iii) a QG-rich domain. Preferably, SNH domain having at least 40% identity to the SNH domain of SEQ ID NO: 2 comprises the residues shown in black in FIG. 2 (SEQ ID NO: 98). Further preferably, the SNH domain is represented by SEQ ID NO: 1. Additionally, the SYT polypeptide or a homologue thereof may comprise one or more of the following: (i) SEQ ID NO: 90; and/or (ii) SEQ ID NO: 91; and/or (iii) a Met-rich domain at the N-terminal preceding the SNH domain.

Further preferably, the allelic variant is an allelic variant of a nucleic acid as represented by any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87. Most preferably, the allelic variant is an allelic variant of a nucleic acid as represented by any one of SEQ ID NO: 3, SEQ ID NO: 5 and SEQ ID NO: 7.

Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, the modulated expression of a SYT nucleic acid or variant thereof is increased expression. The increase in expression may lead to raised SYT mRNA or polypeptide levels, which could equate to raised activity of the SYT polypeptide; or the activity may also be raised when there is no change in polypeptide levels, or even when there is a reduction in polypeptide levels. This may occur when the intrinsic properties of the polypeptide are altered, for example, by making mutant versions that are more active that the wild type polypeptide. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a SYT nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

Methods for reducing the expression of genes or gene products are well documented in the art.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:
(i) Any SYT nucleic acid or variant thereof, as defined hereinabove;
(ii) One or more control sequences capable of driving expression of the nucleic acid sequence of (i); and optionally
(iii) A transcription termination sequence.

A preferred construct is one whether the control sequence is a promoter derived from a plant, preferably from a monocotyledonous plant.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a nucleic acid encoding a SYT polypeptide or homologue thereof). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions. Additionally or alternatively, the promoter may be a tissue-preferred promoter, i.e. one that is capable of preferentially initiating transcription in certain tissues, such as the leaves, roots, seed tissue etc. Promoters able to initiate transcription in certain tissues only are referred to herein as "tissue-specific".

Preferably, the SYT nucleic acid or variant thereof is operably linked to a constitutive promoter. A constitutive promoter is transcriptionally active during most, but not necessarily all, phases of its growth and development and is substantially ubiquitously expressed. Preferably the promoter is derived from a plant, further preferably a monocotyledonous plant. Most preferred is use of a GOS2 promoter (from rice) (SEQ ID NO: 89). It should be clear that the applicability of the present invention is not restricted to the SYT nucleic acid represented by SEQ ID NO: 3, SEQ ID NO: 5 or SEQ ID NO: 7, nor is the applicability of the invention restricted to expression of a SYT nucleic acid when driven by a GOS2 promoter. Examples of other constitutive promoters which may also be used to drive expression of a SYT nucleic acid are shown in Table 4 below.

TABLE 4

Examples of constitutive promoters

| Gene Source | Expression Pattern | Reference |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant. 100: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689, 1992 |
| Rice cyclophilin | Constitutive | Buchholz et al, Plant Mol Biol. 25(5): 837-43, 1994 |
| Maize H3 histone | Constitutive | Lepetit et al, Mol. Gen. Genet. 231: 276-285, 1992 |
| Actin 2 | Constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene that confers a phenotype on a cell in which it is expressed to facilitate the identification and/or selection of cells that are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

The present invention also encompasses plants obtainable by the methods according to the present invention. The present invention therefore provides plants, plant parts and plant cells obtainable by the methods according to the present invention, which plants have introduced therein a SYT nucleic acid or variant thereof and which plants, plant parts and plant cells are preferably from a crop plant, further preferably from a monocotyledonous plant.

The invention also provides a method for the production of transgenic plants having increased yield, comprising introduction and expression in a plant of a SYT nucleic acid or a variant thereof.

More specifically, the present invention provides a method for the production of transgenic plants, preferably monocotyledonous plants, having increased yield, which method comprises:
 (i) introducing and expressing in a plant or plant cell a SYT nucleic acid or variant thereof; and
 (ii) cultivating the plant cell under conditions promoting plant growth and development.

Subsequent generations of the plants obtained from cultivating step (ii) may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The nucleic acid may be introduced directly into a plant cell or into the plant itself (including introduction into a tissue, organ or any other part of a plant). According to a preferred feature of the present invention, the nucleic acid is introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated from there. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. at al., (1982) Nature 296, 72-74; Negrutiu I at al. (1987) Plant Mol Biol 8: 363-373); electroporation of protoplasts (Shillito R. D. et al., 1985 Bio/Technol 3, 1099-1102); microinjection into plant material (Crossway A at al., (1986) Mol. Gen Genet 202: 179-185); DNA or RNA-coated particle bombardment (Klein T M at al., (1987) Nature 327: 70) infection with (non-integrative) viruses and the like. Transgenic rice plants expressing a SYT nucleic acid/gene are preferably produced via *Agrobacterium*-mediated transformation using any of the well known methods for rice transformation, such as described in any of the following: published European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, quantitative PCR, such techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention dearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention. The invention also includes host cells containing an isolated SYT nucleic acid or variant thereof. Preferred host cells according to the invention are plant cells. The invention also extends to harvestable parts of a plant such as, but not limited to seeds, leaves, fruits, flowers, stem cultures, rhizomes, tubers and bulbs. The invention furthermore relates to products derived, preferably directly derived, from a harvestable part of such a plant, such as dry pellets or powders, meal, oil, fat and fatty acids, starch or proteins.

The present invention also encompasses use of SYT nucleic acids or variants thereof and use of SYT polypeptides or homologues thereof and to use of a construct as defined hereinabove in increasing plant yield, especially seed yield. The seed yield is as defined above and preferably includes increased total seed yield or increased TKW.

SYT nucleic acids or variants thereof, or SYT polypeptides or homologues thereof may find use in breeding programmes in which a DNA marker is identified which may be genetically linked to a SYT gene or variant thereof. The SYT nucleic acids/genes or variants thereof, or SYT polypeptides or homologues thereof may be used to define a molecular marker. This DNA or protein marker may then be used in breeding programmes to select plants having increased yield. The SYT gene or variant thereof may, for example, be a nucleic acid as represented by any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87.

Allelic variants of a SYT nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question, for example, different allelic variants of any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87. Growth performance may be monitored in a greenhouse or in the field. Further optional steps include crossing plants, in which the superior allelic variant was identified, with another plant. This could be used, for example, to make a combination of interesting phenotypic features.

A SYT nucleic acid or variant thereof may also be used as probes for genetically and physically mapping the genes that they are a part of, and as markers for traits linked to those genes. Such information may be useful in plant breeding in order to develop lines with desired phenotypes. Such use of SYT nucleic acids or variants thereof requires only a nucleic acid sequence of at least 15 nucleotides in length. The SYT nucleic acids or variants thereof may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the SYT nucleic acids or variants thereof. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the SYT nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet 7:149-154). Although current methods of FISH mapping favor use of large clones (several kb to several hundred kb; see Laan of al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield at al. (1993) Genomics 16:325-332), allele-specific ligation (Landegren of al. (1988) Science 241:1077-1080), nucleotide extension reactions (Sokolov (1990) Nucleic Acid Res. 18:3671), Radiation Hybrid Mapping (Walter of al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield, as described hereinbefore. These yield-enhancing traits may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 1 shows the typical domain structure of SYT polypeptides from plants and mammals. The conserved SNH domain is located at the N-terminal end of the protein. The C-terminal remainder of the protein domain consists of a QG-rich domain in plant SYT polypeptides, and of a QPGY-rich domain in mammalian SYT polypeptides. A Met-rich domain is typically comprised within the first half of the QG-rich (from the N-term to the C-term) in plants or QPGY-rich in mammals. A second Met-rich domain may precede the SNH domain in plant SYT polypeptides FIG. 2 shows a multiple alignment of the N-terminal end of several SYT polypeptides, using VNTI AlignX multiple alignment program, based on a modified ClustalW algorithm (InforMax, Bethesda, Md., at informaxinc.com), with default settings for gap opening penalty of 10 and a gap extension of 0.05). The SNH domain is boxed across the plant and human SYT polypeptides. The last line in the alignment consists of a consensus sequence derived from the aligned sequences. The following polypeptides are shown: Brana_SYT1 (SEQ ID NO: 12); Brana_SYT2 (SEQ ID NO: 40); Bradi_SYT3 (SEQ ID NO: 38); Aqufo_SYT1 (SEQ ID NO: 36); Allce_SYT2 (SEQ ID NO: 34); Pinta_SYT1 (SEQ ID NO: 68); Picsi_SYT1 (SEQ ID NO: 66); Sorbi_SYT3 (SEQ ID NO: 80); Lacse_SYT2 (SEQ ID NO: 56); Horvu_SYT2 (SEQ ID NO: 54); Sacof_SYT2 (SEQ ID NO: 74); Zeama_SYT3 (SEQ ID NO: 88); Triae_SYT2 (SEQ ID NO: 82); Poptr_SYT1 (SEQ ID NO: 70); Vitvi_SYT1 (SEQ ID NO: 86); Triae_SYT3 (SEQ ID NO: 84); Soltu_SYT1 (SEQ ID NO: 78); Sacof_SYT3 (SEQ ID NO: 76); Sacof_SYT1 (SEQ ID NO: 72); Panvi_SYT3 (SEQ ID NO: 64); Maldo_SYT2 (SEQ ID NO: 60); Lyces_SYT1 (SEQ ID NO: 58); Goshi_SYT2 (SEQ ID NO: 52); Goshi_SYT1 (SEQ ID NO: 50); Glyso_SYT2 (SEQ ID NO: 48); Glyma_SYT2 (SEQ ID NO: 46); Eupes_SYT2 (SEQ ID NO: 44); Citsi_SYT2 (SEQ ID NO: 42); Orysa_SYT3 (SEQ ID NO: 24); Arath_SYT2 (SEQ ID NO: 6); Zeama_SYT1 (SEQ ID NO: 28); Medtr_SYT1 (SEQ ID NO: 18); Citsi_SYT1 (SEQ ID NO: 14); Arath_SYT1 (SEQ ID NO: 4); Zeama_SYT2 (SEQ ID NO: 30); Aspof_SYT1 (SEQ ID NO: 10); Orysa_SYT2 (SEQ ID NO: 22); Arath_SYT3 (SEQ ID NO: 8); Orysa_SYT1 (SEQ ID NO: 20); Soltu_SYT2 (SEQ ID NO: 26); Medtr_SYT2 (SEQ ID NO: 62); Homsa_SYT (SEQ ID NO: 32)_; and a consensus sequence (SEQ ID NO: 99).

Figure 3:
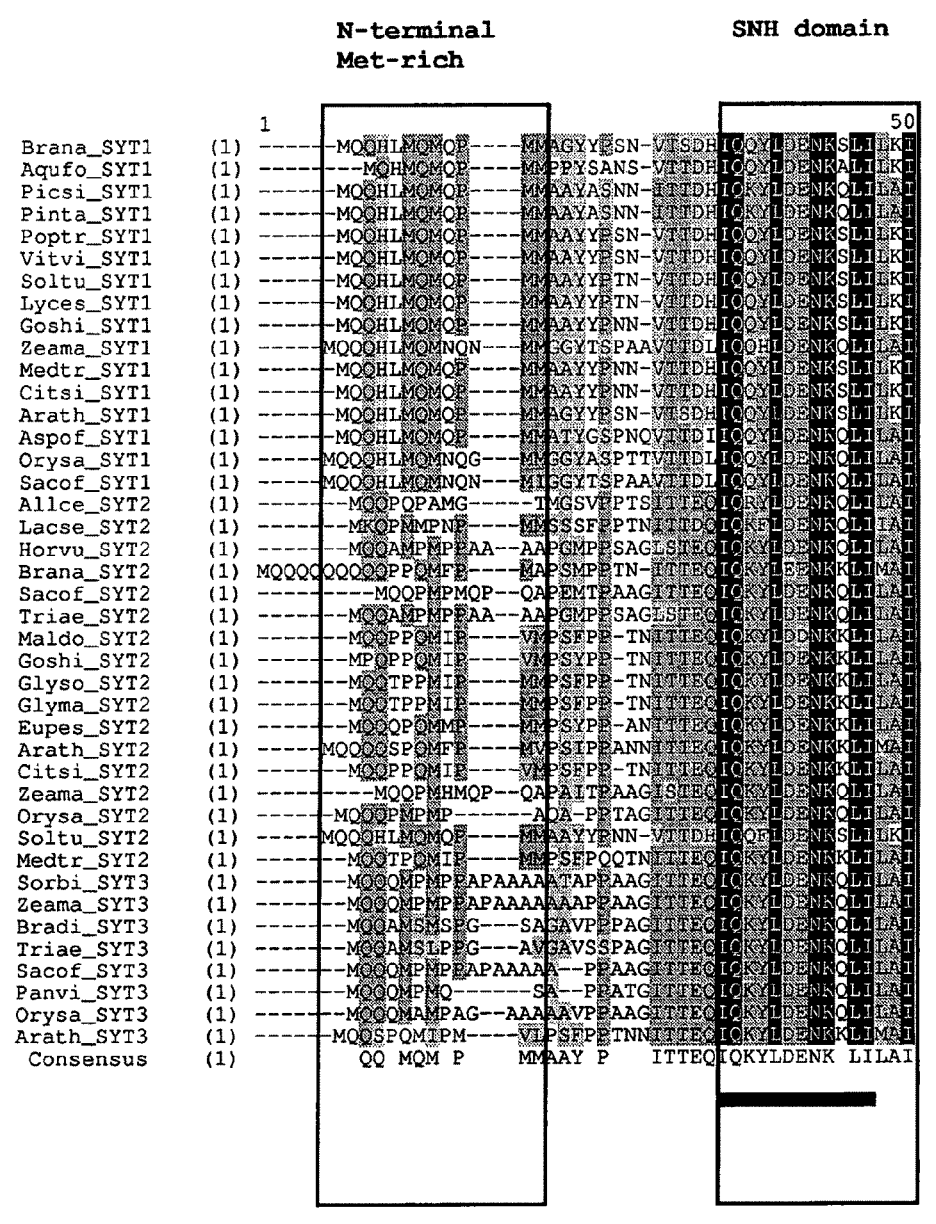

FIG. 3 shows a multiple alignment of several plant SYT polypeptides, using VNTI AlignX multiple alignment program, based on a modified ClustalW algorithm (InforMax, Bethesda, Md., at informaxinc.com), with default settings for gap opening penalty of 10 and a gap extension of 0.05). The two main domains, from N-terminal to C-terminal, are boxed and identified as SNH domain and the Met-rich/QG-rich domain. Additionally, the N-terminal Met-rich domain is also boxed, and the positions of SEQ ID NO: 90 and SEQ ID NO 91 are underlined in bold. The following polypeptides are shown: Brana_SYT1 (SEQ ID NO: 12); Aqufo_SYT1 (SEQ ID NO: 36); Picsi_SYT1 (SEQ ID NO: 66); Pinta_SYT1 (SEQ ID NO: 68); Poptr_SYT1 (SEQ ID NO: 70); Vitvi_SYT1 (SEQ ID NO: 86); Soltu_SYT1 (SEQ ID NO: 78); Lyces_SYT1 (SEQ ID NO: 58); Goshi_SYT1 (SEQ ID NO: 50); Zeama_SYT1 (SEQ ID NO: 28); Medtr_SYT1 (SEQ ID NO: 18); Citsi_SYT1 (SEQ ID NO: 14); Arath_SYT1 (SEQ ID NO: 4); Aspof_SYT1 (SEQ ID NO: 10); Orysa_SYT1 (SEQ ID NO: 20); Sacof_SYT1 (SEQ ID NO: 72); Allce_SYT2 (SEQ ID NO: 34); Lacse_SYT2 (SEQ ID NO: 56); Horvu_SYT2 (SEQ ID NO: 54); Brana_SYT2 (SEQ ID NO: 40); Sacof_SYT2 (SEQ ID NO: 74); Triae_SYT2 (SEQ ID NO: 82); Maldo_SYT2 (SEQ ID NO: 60); Goshi_SYT2 (SEQ ID NO: 52); Glyso_SYT2 (SEQ ID NO: 48); Glyma_SYT2 (SEQ ID NO: 46); Eupes_SYT2 (SEQ ID NO: 44); Arath_SYT2 (SEQ ID NO: 6); Citsi_SYT2 (SEQ ID NO: 42); Zeama_SYT2 (SEQ ID NO: 30); Orysa_SYT2 (SEQ ID NO: 22); Soltu_SYT2 (SEQ ID NO: 26); Medtr_SYT2 (SEQ ID NO: 62); Sorbi_SYT3 (SEQ ID NO: 80); Zeama_SYT3 (SEQ ID NO: 88); Bradi_SYT3 (SEQ ID NO: 38); Triae_SYT3 (SEQ ID NO: 84); Sacof_SYT3 (SEQ ID NO: 76); Panvi_SYT3 (SEQ ID NO: 64); Orysa_SYT3 (SEQ ID NO: 24); Arath_SYT3(SEQ ID NO: 8); and a consensus sequence (SEQ ID NO: 100).

FIG. 8 details examples of sequences useful in performing the methods according to the present invention. SYT nucleic acid sequences are presented from start to stop. The majority of these sequences are derived from EST sequencing, which is of lower quality. Therefore, nucleic acid substitutions may be encountered.

EXAMPLES

Figure 4:
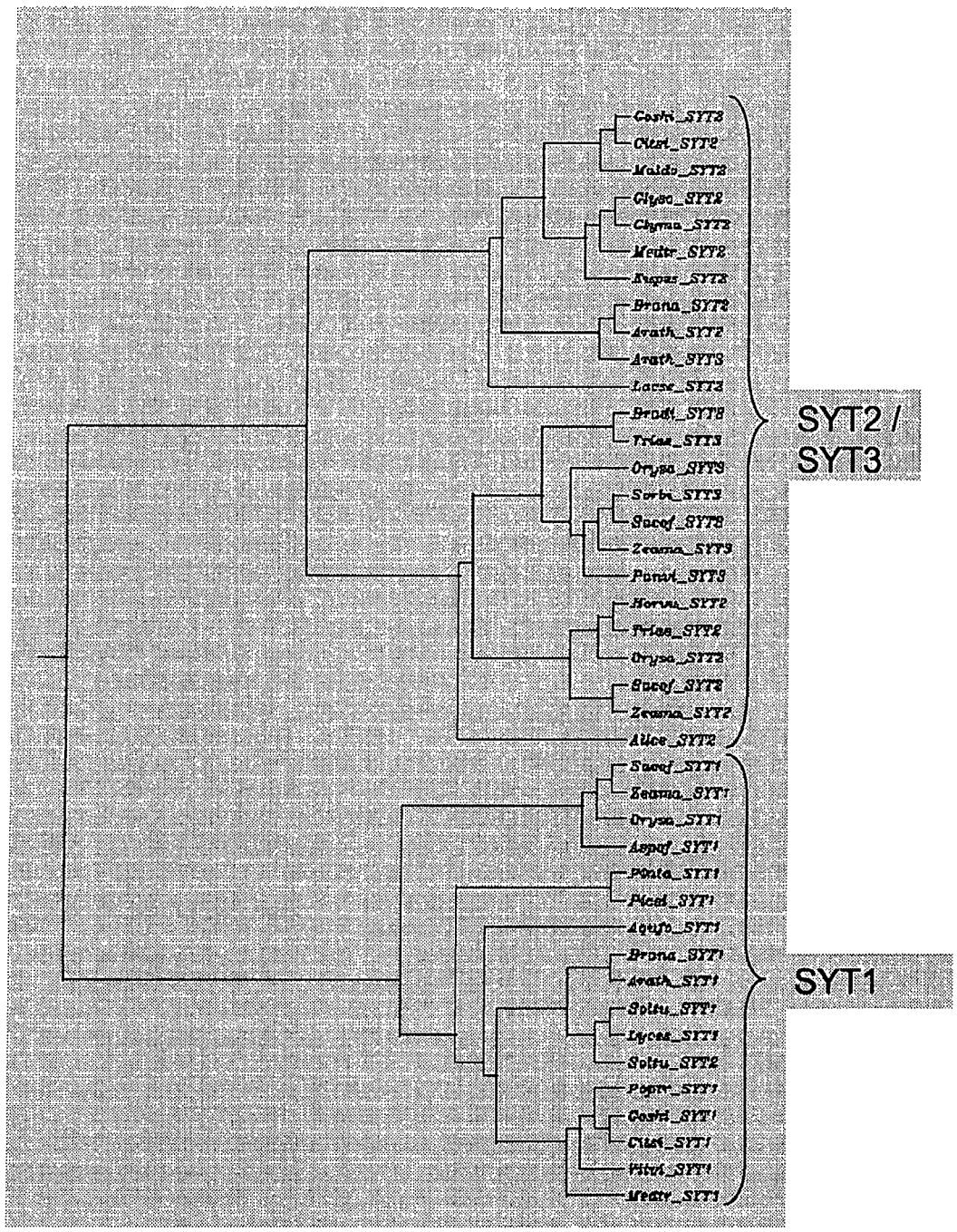
FIG. 4 shows a Neighbour joining tree resulting from the alignment of multiple SYT polypeptides using CLUSTALW 1.83 (align.genome.jp/sit-bin/clustalw). The SYT1 and SYT2/SYT3 clades are identified with brackets.

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Gene Cloning of AtSYT1, AtSYT2 and AtSYT3

The *Arabidopsis thaliana* AtSYT1 gene was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb and the original number of clones was of the order of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 µl PCR mix. Primers prm06681 (SEQ ID NO: 92; sense, start codon in bold, AttB1 site in italic: 5'-GGGGACAAGTTTGTA-CAAAAAAGCAGGCTTAAACAATGCAA-CAGCACCTGATG-3') and prm06682 (SEQ ID NO: 93; reverse, complementary, AttB2 site in italic: 5'-GGGGAC-CACTTTGTACAAGAAAGCTGGGTCAT-CATTAAGATTCCTTGTGC-3'), which include the AttB sites for Gateway recombination, were used for PCR amplification. PCR was performed using Hifi Taq DNA polymerase in standard conditions. A PCR fragment of 727 bp (including attB sites) was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p07466. Plasmid pDONR201 was purchased from Invitrogen, as part of the Gateway® technology.

The *Arabidopsis thaliana* AtSYT2 gene was amplified by PCR using the same method as the *Arabidopsis thaliana* AtSYT1 gene. Primers prm06685 (SEQ ID NO: 94; sense, start codon in bold, AttB1 site in italic: 5'-GGGGA-CAAGTTTGTACAAAAAAGCAGG CTTAAACAATG-CAGCAGCAGCAGTCT 3') and prm06686 (SEQ ID NO: 95); reverse, stop codon in bold, complementary, AttB2 site in italic: 5' GGGGACCACTTTGTACAAGAAAG CTGGGT-TCTTTGGATCCTTTTCACTTG 3'), which include the AttB sites for Gateway recombination, were used for PCR amplification. PCR was performed using Hifi Taq DNA polymerase in standard conditions. A PCR fragment of 666 bp (including attB sites) was amplified and purified as above. The entry clone was numbered p07467.

The *Arabidopsis thaliana* AtSYT3 gene was amplified by PCR using the same method as the *Arabidopsis thaliana* AtSYT1 and AtSYT2 genes. Primers prm06683 (SEQ ID NO: 96; sense, start codon in bold, AttB1 site in italic: 5' GGGGACAAGTTTGTACAAAAAAG CAGGCTTAAA-CAATGCAGCAATCTCCACAGAT 3') and prm06684 (SEQ ID NO: 97; reverse, stop codon in bold, complementary, AttB2 site in italic: 5' GGGGACCACTTTGTAC AAGAAAGCTGGGTTCCTCTATTTCATTTTCCTTCAG 3'), which include the MB sites for Gateway recombination, were used for PCR amplification. PCR was performed using Hifi Taq DNA polymerase in standard conditions. A PCR fragment of 745 bp (including attB sites) was amplified and purified as above. The entry clone was numbered p07604.

Example 2

Vector Construction

The entry clones p07466, p07467 and p07604 were subsequently used in an LR reaction with p00640, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry done. A rice GOS2 promoter (SEQ ID NO: 89) for constitutive expression (PRO0129) was located upstream of this Gateway cassette.

Figure 5:
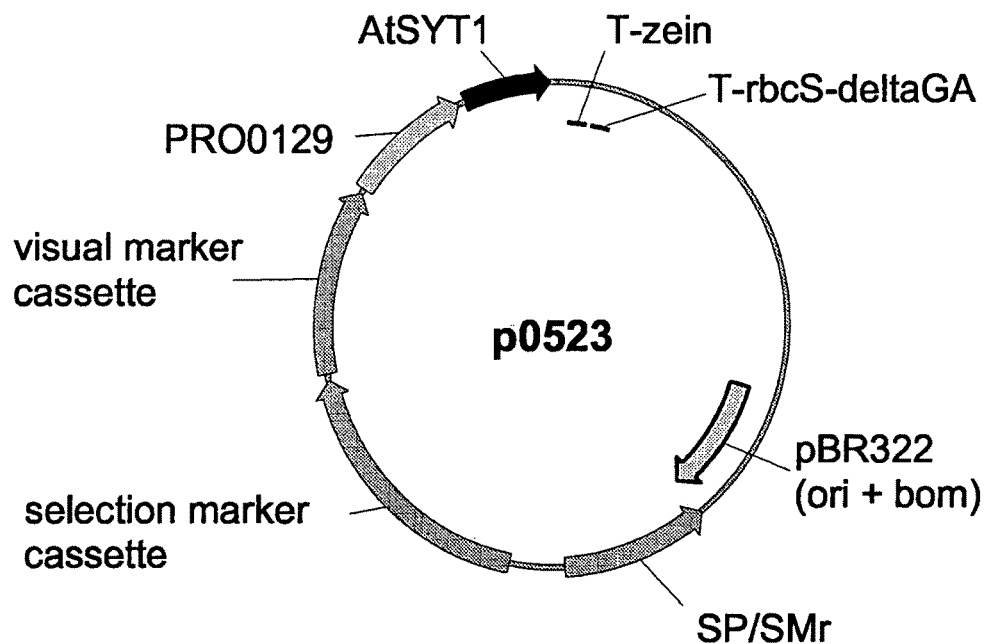
FIG. 5 shows a binary vector p0523, for expression in *Oryza sativa* of an *Arabidopsis thaliana* AtSYT1 under the control of a GOS2 promoter (internal reference PRO0129).
Figure 6:
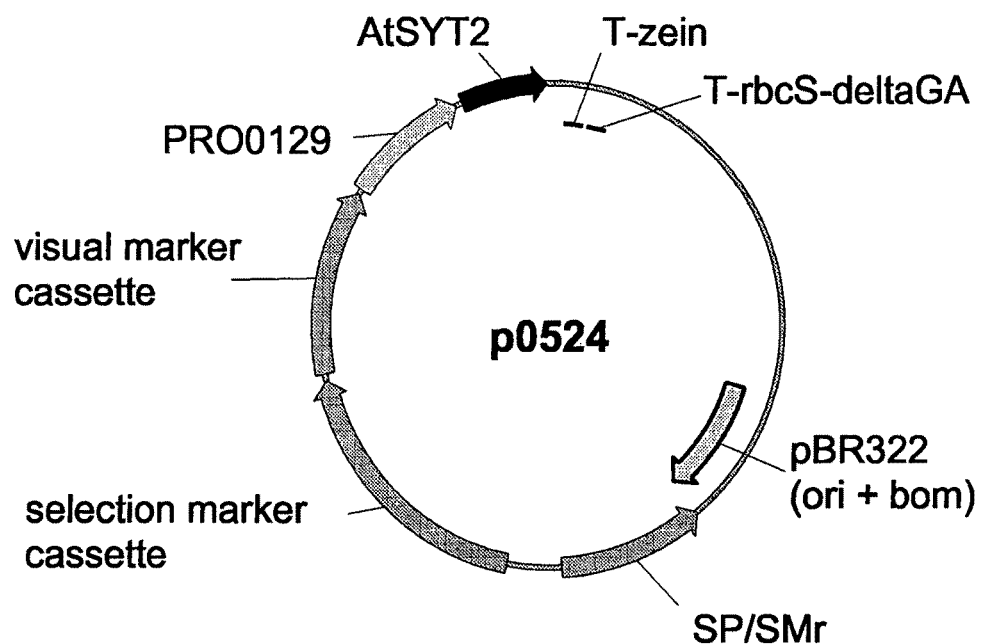
FIG. 6 shows a binary vector p0524, for expression in *Oryza sativa* of an *Arabidopsis thaliana* AtSYT2 under the control of a GOS2 promoter (internal reference PRO0129).
Figure 7:
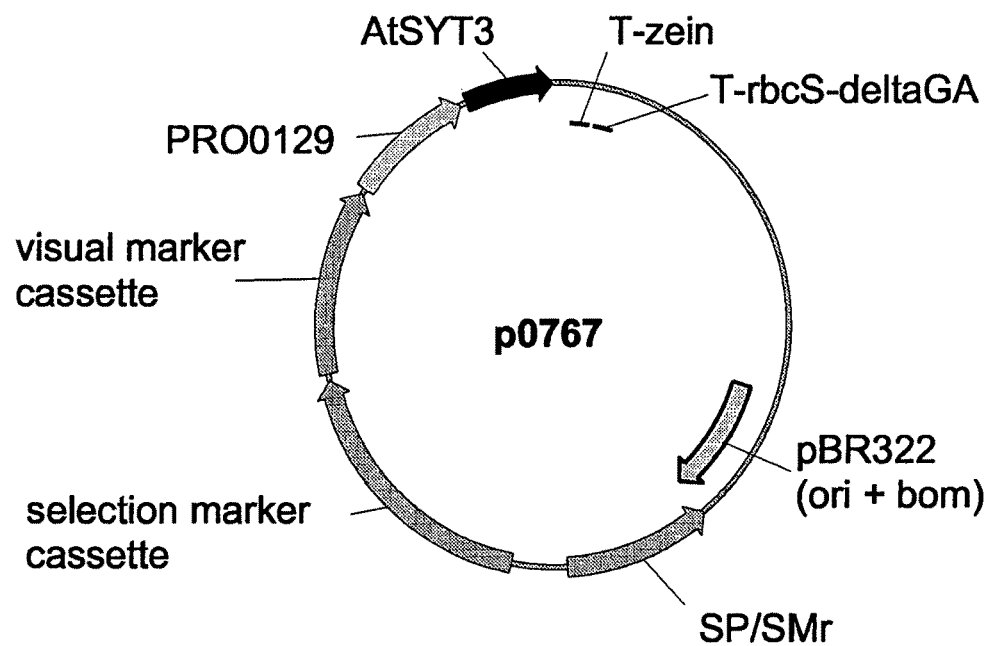
FIG. 7 shows a binary vector p0767, for expression in *Oryza sativa* of an *Arabidopsis thaliana* AtSYT3 under the control of a GOS2 promoter (internal reference PRO0129).

After the LR recombination step, the resulting expression vectors, respectively p0523 for AtSYT1, p0524 for AtSYT2 and p0767 for AtSYT3 (FIGS. 5 to 7) were transformed into *Agrobacterium* strain LBA4044 and subsequently to *Oryza sativa* plants. Transformed rice plants were allowed to grow and were then examined for the parameters described in Example 3.

Example 3

Evaluation and Results of AtSYT1, AtSYT2 and AtSYT3 under the Control of the Rice GOS2 Promoter Approximately 15 to 20 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression.

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

Seed-Related Parameter Measurements

The mature primary panicles were harvested, bagged, barcode-labeled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight.

Individual seed parameters (including width, length, area, weight) were measured using a custom-made device consisting of two main components, a weighing and imaging device, coupled to software for image analysis.

3.1 Total Seed Yield and TKW Measurement Results for Transgenic Plants Grown in the Greenhouse The total seed yield and TKW measurement results for AtSYT1, AtSYT2 and AtSYT3 transgenic plants for the T1 generation are shown in Tables 5 to 7, respectively. The number of lines with an increase in either parameter is indicated. The percentage difference between the transgenics and the corresponding nullizygotes is also shown, as well as the P values from the F test.

Both the total seed yield and TKW are significantly increased in the T1 generation for AtSYT1, AtSYT2 and ATSYT3 transgenic plants (Tables 5 to 7, respectively).

TABLE 5

Results of total seed yield and TKW measurements in the T1 generation of AtSYT1 transgenic plants.

| | Number of events showing an increase | % Difference | P value of F test |
|---|---|---|---|
| Total seed yield | 5 out of 6 | 19 | 0.005 |
| TKW | 6 out of 6 | 11 | <0.0001 |

TABLE 6

Results of total seed yield and TKW measurements in the T1 generation of AtSYT2 transgenic plants.

| | Number of events showing an increase | % Difference | P value of F test |
|---|---|---|---|
| Total seed yield | 4 out of 6 | 37 | 0.05 |
| TKW | 6 out of 6 | 5 | <0.0001 |

TABLE 7

Results of total seed yield and TKW measurements in the T1 generation of AtSYT3 transgenic plants.

| | Number of events showing an increase | % Difference | P value of F test |
|---|---|---|---|
| Total seed yield | 5 out of 6 | 22 | 0.0074 |
| TKW | 5 out of 6 | 7 | <0.0001 |

3.2 Seed Size Measurements Results of Seeds from T2 Generation AtSYT1 Transgenic Plants Individual seed parameters (width, length and area) were measured on the seeds from the T2 plants, using a custom-made device consisting of two main components, a weighing and an imaging device, coupled to software for image analysis. Measurements were performed on both husked and dehusked seeds.

The average individual seed area, length and width measurement results of the T3 seeds (harvested from the T2 plants) for the *Oryza saliva* AtSYT1 transgenic plants are shown in Table 8. The percentage difference between the transgenics and the corresponding nullizygotes is shown, as well as the number of events with an increase in a given parameter and the p values from the F test.

The average individual seed area, length and width of the T3 husked and dehusked seeds (harvested from the T2 transgenic *Oryza sativa* AtSYT1 plants) were all significantly increased compared to their null counterparts (Table 8).

TABLE 8

Individual seed area, length and width measurements of the T3 husked and dehusked seeds (harvested from the T2 plants) of the *Oryza sativa* AtSYT1 transgenic plants compared to their null counterparts.

| | Number of events showing an increase | % Difference | P value of F test |
|---|---|---|---|
| Average seed area | 6 out of 6 | 11% | <0.0001 |
| Average dehusked seed area | 6 out of 6 | 10% | <0.0001 |
| Average seed length | 6 out of 6 | 6% | <0.0001 |
| Average dehusked seed length | 6 out of 6 | 5% | <0.0001 |
| Average seed width | 6 out of 6 | 5% | <0.0001 |
| Average dehusked seed width | 6 out of 6 | 4% | <0.0001 |

3.3 Embryo and Endosperm Size Measurement Results of Seeds from T2 Generation AtSYT1 Transgenic Plants Embryo and endosperm size were also measured by longitudinally cutting in half dehusked seeds and staining the seed halves for 2 to 3 hours at 35° C. with colouring agent, 2,3,5-triphenyltetrazolium chloride. Following staining, the two halves were placed on agarose gel in a Petri dish ready for imaging. Three independent events were taken, and from each event 120 seeds homozygous for the transgene and 120 seeds without the transgene were analysed. Digital photographs of the seeds were taken and the images analysed with ImagePro software. The results for the three events are given below.

For all three events, embryos of seeds homozygous for the transgene were bigger than the embryos of seeds without the transgene. There was a significant increase in the average area of the embryo for the seeds of each of the three events, with p values from the t-test of 0.0325, <0.0001 and <0.0001. Similarly, there was a significant increase in the average perimeter of the embryo for the seeds of each of the three events, with p values from the t-test of 0.0176, <0.0001 and <0.0001. Furthermore, there was a significant increase in the average area and perimeter of the endosperm for the seeds of each of the three events, all giving p values of <0.0001.

3.4 TKW Measurement Results for AtSYT1 Transgenic Plants Grown in the Field

The AtSYT1 homozygous transgenic plants and their corresponding controls were transplanted into the field in September and harvested in December. Four repetitions were planted for each entry (four events) with 104 plants per repeat. The spacing between plants was of 20 by 20 cm. The field was flooded and irrigated. After seed harvest, the seeds were measured for TKW as described above. Results of these measurements are presented in Table 9.

TABLE 9

Results of TKW measurements in the T3 generation of AtSYT1 transgenic plants grown in the field.

| Event | Percentage increase (%) in TKW |
|---|---|
| Event 1 | 8 |
| Event 2 | 6 |
| Event 3 | 5 |
| Event 4 | 10 |

The TKW is increased in all the transgenic events evaluated in the field.

The invention claimed is:

1. A method for increasing plant yield relative to a corresponding wild type plant, comprising:
   (a) introducing and expressing in a plant or plant cell a recombinant nucleic acid encoding a plant synovial sarcoma translocation (SYT) polypeptide,
   (b) cultivating the plant or plant cell under conditions promoting plant growth and development; and
   (c) selecting a plant from step (b) having increased yield relative to a corresponding wild type plant,
wherein said plant SYT polypeptide comprises the amino acid sequence of SEQ ID NO: 4, SEQ ID NO: 20, SEQ ID NO: 28 or SEQ ID NO: 62, or comprises from N-terminal to C-terminal: (i) an SNH domain having at least 70% sequence identity to the SNH domain of SEQ ID NO: 2; (ii) a Met-rich domain; and (iii) a QG-rich domain; and wherein the increased yield is selected from the group consisting of increased seed yield, increased root biomass, and increased biomass of fruit, nuts and/or pulses.

2. The method of claim 1, wherein said plant SYT polypeptide further comprises one or more of the following: (i) SEQ ID NO: 90; (ii) SEQ ID NO: 91; (iii) a Met-rich domain at the N-terminus preceding the SNH domain.

3. The method of claim 1, wherein said recombinant nucleic acid is overexpressed in a plant.

4. The method of claim 1, wherein said recombinant nucleic acid is of plant origin.

5. The method of claim 1, wherein said SYT polypeptide comprises the amino acid sequence of SEQ ID NO: 2, SEQ ID NO: 4, SEQ ID NO: 6, SEQ ID NO: 8, SEQ ID NO: 20, SEQ ID NO: 28, or SEQ ID NO: 62.

6. The method of claim 1, wherein said recombinant nucleic acid is operably linked to a constitutive promoter.

7. The method of claim 6, wherein said constitutive promoter is of plant origin.

8. The method of claim 6, wherein said constitutive promoter is a GOS2 promoter.

9. The method of claim 1, wherein said increased yield is increased seed yield.

10. The method according to claim 9, wherein said increased seed yield is increased Thousand Kernel Weight (TKW).

11. A transgenic plant, plant part or plant cell produced by the method according to claim 1, wherein the plant, plant part or plant cell comprises said recombinant nucleic acid and wherein expression of said SYT polypeptide in said plant, plant part or plant cell confers increased yield relative to a corresponding wild type plant, plant part or plant.

12. A construct comprising:
   (i) a recombinant nucleic acid encoding a plant SYT polypeptide;

(ii) one or more control sequences capable of driving expression of the recombinant nucleic acid sequence of (i); and (iii) a transcription termination sequence, wherein said one or more control sequence is of plant origin and heterologous to said recombinant nucleic acid, wherein said construct is a plant transformation construct, and wherein said SYT polypeptide comprises the amino acid sequence of SEQ ID NO: 4, SEQ ID NO: 20, SEQ ID NO: 28, or SEQ ID NO: 62, or comprises from N-terminal to C-terminal: (i) an SNH domain having at least 70% sequence identity to the SNH domain of SEQ ID NO: 2; (ii) a Met-rich domain; and (iii) a QG-rich domain;

wherein the construct expressed in a plant confers increased yield relative to a corresponding wild type plant, and wherein the increased yield is selected from the group consisting of increased seed yield, increased root biomass, and increased biomass of fruit, nuts and/or pulses.

13. The construct according to claim 12, wherein said control sequence is a constitutive promoter obtained from a monocot plant.

14. The construct according to claim 13, wherein said constitutive promoter is a GOS2 promoter.

15. The construct according to claim 14, wherein said GOS2 promoter comprises the sequence of SEQ ID NO: 89.

16. A transgenic plant, plant part or plant cell comprising the construct of claim 12, wherein said transgenic plant, plant part or plant cell expresses said SYT polypeptide which confers increased yield relative to a corresponding wild type plant, plant part or plant cell.

17. A method for the production of a transgenic plant having increased yield relative to a corresponding wild type plant, which method comprises:
(i) introducing and expressing in a plant or plant cell a recombinant nucleic acid encoding a plant synovial sarcoma translocation (SYT) polypeptide;
(ii) cultivating the plant or plant cell under conditions promoting plant growth and development;
(iii) selecting a transgenic plant from step (ii) having increased yield relative to a corresponding wild type plant; and
(iv) producing a progeny plant from said transgenic plant, wherein said progeny plant comprises said recombinant nucleic acid and has increased yield relative to a corresponding wild type plant;
wherein said SYT polypeptide comprises the amino acid sequence of SEQ ID NO: 4, SEQ ID NO: 20, SEQ ID NO: 28 or SEQ ID NO: 62, or comprises from N-terminal to C-terminal: (i) an SNH domain having at least 70% sequence identity to the SNH domain of SEQ ID NO: 2; (ii) a Met-rich domain; and (iii) a QG-rich domain; and wherein the increased yield is selected from the group consisting of increased seed yield, increased root biomass, and increased biomass of fruit, nuts and/or pulses.

18. The method according to claim 17, comprising generating one or more subsequent generations of plants and parts thereof including seeds by crossing plants obtained by said cultivating step (ii).

19. A transgenic plant or part thereof having increased yield, wherein said transgenic plant or part thereof comprises a recombinant nucleic acid encoding a plant synovial sarcoma translocation (SYT) polypeptide introduced into said plant or plant part, wherein said transgenic plant or part thereof expresses said recombinant nucleic acid encoding said SYT polypeptide which confers said increased yield relative to a corresponding wild type plant, wherein said nucleic acid is operably linked to a promoter obtained from a plant, wherein said plant SYT polypeptide comprises the amino acid sequence of SEQ ID NO: 4, SEQ ID NO: 20, SEQ ID NO: 28 or SEQ ID NO: 62, or comprises from N-terminal to C-terminal: (i) an SNH domain having at least 70% sequence identity to the SNH domain of SEQ ID NO: 2; (ii) a Met-rich domain; and (iii) a QG-rich domain; and wherein the increased yield is selected from the group consisting of increased seed yield, increased root biomass, and increased biomass of fruit, nuts and/or pulses.

20. The transgenic plant according to claim 11, wherein said plant is a monocotyledonous plant.

21. Harvestable parts of the transgenic plant of claim 11, wherein said harvestable parts comprise said recombinant nucleic acid encoding the plant SYT polypeptide.

22. The harvestable parts of claim 21, wherein said harvestable parts are seeds.

23. Products obtained from the transgenic plant of claim 19 and/or from harvestable parts of said plant, wherein said products comprise said recombinant nucleic acid encoding the plant SYT polypeptide.

24. The method of claim 1, wherein said recombinant nucleic acid is from a dicotyledonous plant.

25. The method of claim 6, wherein the constitutive promoter is from a monocotyledonous plant.

26. The method of claim 17, wherein said plant is a monocotyledonous plant.

27. The method of claim 17, wherein the increased yield is increased seed yield.

28. The transgenic plant of claim 19, wherein the plant is selected from the group consisting of sugar cane, rice, maize, wheat, barley, millet, rye, oats, and sorghum.

29. The method of claim 1, wherein the SNH domain has at least 85% sequence identity to the SNH domain of SEQ ID NO: 2.

30. The method of claim 1, wherein the SNH domain comprises the SNH domain of SEQ ID NO: 2.

31. The construct of claim 12, wherein the SNH domain has at least 85% sequence identity to the SNH domain of SEQ ID NO: 2.

32. The construct of claim 12, wherein the SNH domain comprises the SNH domain of SEQ ID NO: 2.

33. The transgenic plant or part thereof of claim 19, wherein the SNH domain has at least 85% sequence identity to the SNH domain of SEQ ID NO: 2.

34. The transgenic plant or part thereof of claim 19, wherein the SNH domain comprises the SNH domain of SEQ ID NO: 2.

35. The method of claim 17, wherein the SNH domain has at least 85% sequence identity to the SNH domain of SEQ ID NO: 2.

36. The method of claim 17, wherein the SNH domain comprises the SNH domain of SEQ ID NO: 2.

37. The construct of claim 12, wherein said SYT polypeptide comprises the amino acid sequence of SEQ ID NO: 2, SEQ ID NO: 4, SEQ ID NO: 6, SEQ ID NO: 8, SEQ ID NO: 20, SEQ ID NO: 28, or SEQ ID NO: 62.

38. The method of claim 17, wherein said SYT polypeptide comprises the amino acid sequence of SEQ ID NO: 2, SEQ ID NO: 4, SEQ ID NO: 6, SEQ ID NO: 8, SEQ ID NO: 20, SEQ ID NO: 28, or SEQ ID NO: 62.

39. The transgenic plant or part thereof of claim 19, wherein said SYT polypeptide comprises the amino acid sequence of SEQ ID NO: 2, SEQ ID NO: 4, SEQ ID NO: 6, SEQ ID NO: 8, SEQ ID NO: 20, SEQ ID NO: 28, or SEQ ID NO: 62.

* * * * *

UNITED STATES PATENT AND TRADEMARK OFFICE
CERTIFICATE OF CORRECTION

PATENT NO.        : 8,426,683 B2
APPLICATION NO.   : 11/795976
DATED             : April 23, 2013
INVENTOR(S)       : Valerie Frankard It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1442 days.

Signed and Sealed this
Eighth Day of September, 2015

Michelle K. Lee
*Director of the United States Patent and Trademark Office*

SEQUENCE LISTING

```
<160> NUMBER OF SEQ ID NOS: 100

<210> SEQ ID NO 1
<211> LENGTH: 46
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa can be either Gln or Lys
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be either Asp or Glu
<220> FEATURE:
<221> NAME/KEY: MISC_FEATURE
<222> LOCATION: (7)..(7)
<223> OTHER INFORMATION: Xaa can be either Glu or Asp
<220> FEATURE:
<221> NAME/KEY: MISC_FEATURE
<222> LOCATION: (9)..(9)
<223> OTHER INFORMATION: Xaa can be either Lys or Asn
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid
```

```
<220> FEATURE:
<221> NAME/KEY: MISC_FEATURE
<222> LOCATION: (14)..(14)
<223> OTHER INFORMATION: Xaa can be either Cys, Ala and Lys
<220> FEATURE:
<221> NAME/KEY: MISC_FEATURE
<222> LOCATION: (16)..(16)
<223> OTHER INFORMATION: Xaa can be either Leu, Val or Met
<220> FEATURE:
<221> NAME/KEY: MISC_FEATURE
<222> LOCATION: (17)..(17)
<223> OTHER INFORMATION: Xaa can be either Glu, Asp or Ser
<220> FEATURE:
<221> NAME/KEY: MISC_FEATURE
<222> LOCATION: (18)..(18)
<223> OTHER INFORMATION: Xaa can be either Ser or Asn
<220> FEATURE:
<221> NAME/KEY: MISC_FEATURE
<222> LOCATION: (19)..(19)
<223> OTHER INFORMATION: Xaa can be either Gln or Leu
<220> FEATURE:
<221> NAME/KEY: MISC_FEATURE
<222> LOCATION: (21)..(21)
<223> OTHER INFORMATION: Xaa can be any amino acid
<220> FEATURE:
<221> NAME/KEY: MISC_FEATURE
<222> LOCATION: (23)..(23)
<223> OTHER INFORMATION: Xaa can be either Lys or Arg
<220> FEATURE:
<221> NAME/KEY: MISC_FEATURE
<222> LOCATION: (24)..(25)
<223> OTHER INFORMATION: Xaa can be any amino acid
<220> FEATURE:
<221> NAME/KEY: MISC_FEATURE
<222> LOCATION: (28)..(28)
<223> OTHER INFORMATION: Xaa can be either Ala, Glu or Ser
<220> FEATURE:
<221> NAME/KEY: MISC_FEATURE
<222> LOCATION: (29)..(30)
<223> OTHER INFORMATION: Xaa can be any amino acid
<220> FEATURE:
<221> NAME/KEY: MISC_FEATURE
<222> LOCATION: (32)..(32)
<223> OTHER INFORMATION: Xaa can be any either Ala, Ser or Gln
<220> FEATURE:
<221> NAME/KEY: MISC_FEATURE
<222> LOCATION: (33)..(33)
<223> OTHER INFORMATION: Xaa can be any amino acid
<220> FEATURE:
<221> NAME/KEY: MISC_FEATURE
<222> LOCATION: (35)..(35)
<223> OTHER INFORMATION: Xaa can be either Gln or His
<220> FEATURE:
<221> NAME/KEY: MISC_FEATURE
<222> LOCATION: (36)..(36)
<223> OTHER INFORMATION: Xaa can be any amino acid
<220> FEATURE:
<221> NAME/KEY: MISC_FEATURE
<222> LOCATION: (39)..(39)
<223> OTHER INFORMATION: Xaa can be either Met, Leu or Val
<220> FEATURE:
<221> NAME/KEY: MISC_FEATURE
<222> LOCATION: (43)..(43)
<223> OTHER INFORMATION: Xaa can be either Ala or Thr

<400> SEQUENCE: 1

Ile Gln Xaa Xaa Leu Xaa Xaa Asn Xaa Xaa Leu Ile Xaa Xaa Ile Xaa
1               5                   10                  15

Xaa Xaa Xaa Asn Xaa Gly Xaa Xaa Xaa Glu Cys Xaa Xaa Xaa Gln Xaa
                20                  25                  30

Xaa Leu Xaa Xaa Asn Leu Xaa Tyr Leu Ala Xaa Ile Ala Asp
            35                  40                  45

<210> SEQ ID NO 2
<211> LENGTH: 46
<212> TYPE: PRT
```

<213> ORGANISM: Arabidopsis thaliana

<400> SEQUENCE: 2

```
Ile Gln Gln Tyr Leu Asp Glu Asn Lys Ser Leu Ile Leu Lys Ile Val
1               5                   10                  15

Glu Ser Gln Asn Ser Gly Lys Leu Ser Glu Cys Ala Glu Asn Gln Ala
            20                  25                  30

Arg Leu Gln Arg Asn Leu Met Tyr Leu Ala Ala Ile Ala Asp
        35                  40                  45
```

<210> SEQ ID NO 3
<211> LENGTH: 633
<212> TYPE: DNA
<213> ORGANISM: Arabidopsis thaliana
<220> FEATURE:
<221> NAME/KEY: misc_feature
<223> OTHER INFORMATION: a at position 386 AND t at position 425 can be changed to g at position 386 AND c at position 425

<400> SEQUENCE: 3

```
atgcaacagc acctgatgca gatgcagccc atgatggctg gttactaccc cagcaatgtt    60
acctctgatc atatccaaca gtacttggac gaaaacaaat cgttgattct gaagattgtt   120
gagtctcaaa actctggaaa gcttagcgaa tgcgccgaga tcaagcaag gcttcaacgc    180
aacctaatgt acctagctgc aatagcagat tctcagcctc agccaccaag tgtgcatagc   240
cagtatggat ctgctggtgg tgggatgatt cagggagaag gagggtcaca ctatttgcag   300
cagcaacaag cgactcaaca gcaacagatg actcagcagt ctctaatggc ggctcgatct   360
tcaatgttgt atgctcagca acagcagcag cagcagcctt acgcgacgct tcagcatcag   420
caattgcacc atagccagct tggaatgagc tcgagcagcg gaggaggagg aagcagtggt   480
ctccatatcc ttcagggaga ggctggtggg tttcatgatt ttggccgtgg gaagccggaa   540
atgggaagtg gtggtggcgg tgaaggcaga ggaggaagtt caggggatgg tggagaaacc   600
ctttacttga aatcatcaga tgatgggaat tga                                633
```

<210> SEQ ID NO 4
<211> LENGTH: 210
<212> TYPE: PRT
<213> ORGANISM: Arabidopsis thaliana
<220> FEATURE:
<221> NAME/KEY: MISC_FEATURE
<223> OTHER INFORMATION: Gln at position 129 AND Leu at position 141 can be changed to Arg at position 129 AND Ser at position 141

<400> SEQUENCE: 4

```
Met Gln Gln His Leu Met Gln Met Gln Pro Met Met Ala Gly Tyr Tyr
1               5                   10                  15

Pro Ser Asn Val Thr Ser Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ser Gln Pro Gln Pro Pro Ser Val His Ser
65                  70                  75                  80

Gln Tyr Gly Ser Ala Gly Gly Gly Met Ile Gln Gly Glu Gly Gly Ser
                85                  90                  95

His Tyr Leu Gln Gln Gln Gln Ala Thr Gln Gln Gln Met Thr Gln
            100                 105                 110
```

```
Gln Ser Leu Met Ala Ala Arg Ser Ser Met Leu Tyr Ala Gln Gln Gln
            115                 120                 125

Gln Gln Gln Gln Pro Tyr Ala Thr Leu Gln His Gln Gln Leu His His
        130                 135                 140

Ser Gln Leu Gly Met Ser Ser Ser Gly Gly Gly Ser Ser Gly
145                 150                 155                 160

Leu His Ile Leu Gln Gly Glu Ala Gly Gly Phe His Asp Phe Gly Arg
                165                 170                 175

Gly Lys Pro Glu Met Gly Ser Gly Gly Gly Glu Gly Arg Gly Gly
            180                 185                 190

Ser Ser Gly Asp Gly Gly Glu Thr Leu Tyr Leu Lys Ser Asp Asp
        195                 200                 205

Gly Asn
    210

<210> SEQ ID NO 5
<211> LENGTH: 588
<212> TYPE: DNA
<213> ORGANISM: Arabidopsis thaliana

<400> SEQUENCE: 5
atgcagcagc agcagtctcc gcaaatgttt ccgatggttc cgtcgattcc ccctgctaac     60
aacatcacta ccgaacagat ccaaaagtac cttgatgaga caagaagct gattatggcc    120
atcatggaaa accagaatct cggtaaactt gctgagtgcg cccagtacca agctcttctc    180
cagaagaact tgatgtatct tgctgcaatt gctgatgctc aacccccacc acctacgcca    240
ggaccttcac catctacagc tgtcgctgcc cagatggcaa caccgcattc tgggatgcaa    300
ccacctagct acttcatgca acacccacaa gcatccctg cagggatttt cgctccaagg    360
ggtcctttac agtttggtag cccactccag tttcaggatc cgcaacagca gcagcagata    420
catcagcaag ctatgcaagg acacatgggg attagaccaa tgggtatgac caacaacggg    480
atgcagcatg cgatgcaaca accagaaacc ggtcttggag aaacgtgggg cttagagga    540
ggaaagcaag atggagcaga tggacaagga aagatgatg gcaagtga              588

<210> SEQ ID NO 6
<211> LENGTH: 195
<212> TYPE: PRT
<213> ORGANISM: Arabidopsis thaliana

<400> SEQUENCE: 6

Met Gln Gln Gln Gln Ser Pro Gln Met Phe Pro Met Val Pro Ser Ile
1               5                   10                  15

Pro Pro Ala Asn Asn Ile Thr Thr Glu Gln Ile Gln Lys Tyr Leu Asp
            20                  25                  30

Glu Asn Lys Lys Leu Ile Met Ala Ile Met Glu Asn Gln Asn Leu Gly
        35                  40                  45

Lys Leu Ala Glu Cys Ala Gln Tyr Gln Ala Leu Leu Gln Lys Asn Leu
    50                  55                  60

Met Tyr Leu Ala Ala Ile Ala Asp Ala Gln Pro Pro Pro Thr Pro
65                  70                  75                  80

Gly Pro Ser Pro Ser Thr Ala Val Ala Ala Gln Met Ala Thr Pro His
                85                  90                  95

Ser Gly Met Gln Pro Pro Ser Tyr Phe Met Gln His Pro Gln Ala Ser
            100                 105                 110

Pro Ala Gly Ile Phe Ala Pro Arg Gly Pro Leu Gln Phe Gly Ser Pro
        115                 120                 125
```

```
Leu Gln Phe Gln Asp Pro Gln Gln Gln Gln Ile His Gln Ala
    130                 135                 140
Met Gln Gly His Met Gly Ile Arg Pro Met Gly Met Thr Asn Asn Gly
145                 150                 155                 160
Met Gln His Ala Met Gln Pro Glu Thr Gly Leu Gly Gly Asn Val
                165                 170                 175
Gly Leu Arg Gly Gly Lys Gln Asp Gly Ala Asp Gly Gly Lys Asp
            180                 185                 190
Asp Gly Lys
        195

<210> SEQ ID NO 7
<211> LENGTH: 672
<212> TYPE: DNA
<213> ORGANISM: Arabidopsis thaliana

<400> SEQUENCE: 7
atgcagcaat ctccacagat gattccgatg gttcttcctt catttccgcc accaataat       60
atcaccaccg aacagatcca aaagtatctt gatgagaaca agaagctgat aatggcgatc      120
ttggaaaatc agaacctcgg taaacttgca gaatgtgctc agtatcaagc tcttctccag      180
aagaatttga tgtatctcgc tgcaattgcg gatgctcaac ctcagccacc agcagctaca      240
ctaacatcag gagccatgac tccccaagca atggctccta tccgtcatc aatgcagcca       300
ccaccaagct acttcatgca gcaacatcaa gctgtgggaa tggctcaaca aatacctcct      360
gggattttcc ctcctagagg tccattgcaa tttggtagcc cgcatcagtt tctggatccg      420
cagcaacagt acatcaaca agctatgcaa gggcacatgg ggattagacc aatgggtttg      480
aataataaca acggactgca acatcaaatg caccaccatg aaactgctct tgccgcaaac      540
aatgcgggtc ctaacgatgc tagtggagga ggtaaaccgg atgggaccaa tatgagccag      600
agtggagctg atgggcaagg tggctcagcc gctagacatg cggtggtga tgcaaaaact       660
gaaggaaaat ga                                                         672

<210> SEQ ID NO 8
<211> LENGTH: 223
<212> TYPE: PRT
<213> ORGANISM: Arabidopsis thaliana

<400> SEQUENCE: 8

Met Gln Gln Ser Pro Gln Met Ile Pro Met Val Leu Pro Ser Phe Pro
1               5                   10                  15
Pro Thr Asn Asn Ile Thr Thr Glu Gln Ile Gln Lys Tyr Leu Asp Glu
                20                  25                  30
Asn Lys Lys Leu Ile Met Ala Ile Leu Glu Asn Gln Asn Leu Gly Lys
            35                  40                  45
Leu Ala Glu Cys Ala Gln Tyr Gln Ala Leu Leu Gln Lys Asn Leu Met
        50                  55                  60
Tyr Leu Ala Ala Ile Ala Asp Ala Gln Pro Gln Pro Pro Ala Ala Thr
65                  70                  75                  80
Leu Thr Ser Gly Ala Met Thr Pro Gln Ala Met Ala Pro Asn Pro Ser
                85                  90                  95
Ser Met Gln Pro Pro Ser Tyr Phe Met Gln His Gln Ala Val
                100                 105                 110
Gly Met Ala Gln Gln Ile Pro Pro Gly Ile Phe Pro Pro Arg Gly Pro
            115                 120                 125
```

```
Leu Gln Phe Gly Ser Pro His Gln Phe Leu Asp Pro Gln Gln Gln Leu
        130                 135                 140

His Gln Gln Ala Met Gln Gly His Met Gly Ile Arg Pro Met Gly Leu
145                 150                 155                 160

Asn Asn Asn Asn Gly Leu Gln His Gln Met His His His Glu Thr Ala
                165                 170                 175

Leu Ala Ala Asn Asn Ala Gly Pro Asn Asp Ala Ser Gly Gly Gly Lys
                180                 185                 190

Pro Asp Gly Thr Asn Met Ser Gln Ser Gly Ala Asp Gly Gln Gly Gly
            195                 200                 205

Ser Ala Ala Arg His Gly Gly Gly Asp Ala Lys Thr Glu Gly Lys
        210                 215                 220

<210> SEQ ID NO 9
<211> LENGTH: 633
<212> TYPE: DNA
<213> ORGANISM: Aspergillus officinalis

<400> SEQUENCE: 9
atgcagcagc acctgatgca gatgcagccc atgatggcaa cctacggttc accgaatcag      60
gtcaccaccg atatcattca gcagtatctg gacgagaaca agcagttgat tctggctatt     120
cttgaaaacc aaaattcagg aaaagctgat gaatgtgctg agaatcaggc taagcttcag     180
aggaatctga tgtatcttgc agccattgcg gatagccagc ccaagttcc taccattgct     240 cagtatcctc ccaacgctgt tgctgctatg caatcgagtg ctcgctacat gcaacaacac     300
caagcagctc aacagatgac ccctcaatct ctcatggctg ctcgctcctc aatgctctac     360
tcacagtccc caatgtctgc actccagcag caacagcagc aagcagcaat gcatagccag     420
ctcgccatga gctccggagg caacaacagc agcaccggag gattcaccat tcttcatggt     480
gaagctagca taggaggcaa tggctcaatg aattctggtg gagtctttgg agattttgga     540
cggagcagcg gtgggaagca agagactggg agcgaagggc acgggacaga gactcctatg     600
tacctgaaag gctctgaaga agaaggaaac tga                                 633

<210> SEQ ID NO 10
<211> LENGTH: 210
<212> TYPE: PRT
<213> ORGANISM: Aspergillus officinalis

<400> SEQUENCE: 10

Met Gln Gln His Leu Met Gln Met Gln Pro Met Met Ala Thr Tyr Gly
1               5                   10                  15

Ser Pro Asn Gln Val Thr Thr Asp Ile Ile Gln Gln Tyr Leu Asp Glu
            20                  25                  30

Asn Lys Gln Leu Ile Leu Ala Ile Leu Glu Asn Gln Asn Ser Gly Lys
        35                  40                  45

Ala Asp Glu Cys Ala Glu Asn Gln Ala Lys Leu Gln Arg Asn Leu Met
    50                  55                  60

Tyr Leu Ala Ala Ile Ala Asp Ser Gln Pro Gln Val Pro Thr Ile Ala
65                  70                  75                  80

Gln Tyr Pro Pro Asn Ala Val Ala Ala Met Gln Ser Ser Ala Arg Tyr
                85                  90                  95

Met Gln Gln His Gln Ala Ala Gln Gln Met Thr Pro Gln Ser Leu Met
            100                 105                 110

Ala Ala Arg Ser Ser Met Leu Tyr Ser Gln Ser Pro Met Ser Ala Leu
        115                 120                 125
```

Gln Gln Gln Gln Gln Gln Ala Ala Met His Ser Gln Leu Ala Met Ser
                130                 135                 140

Ser Gly Gly Asn Asn Ser Ser Thr Gly Gly Phe Thr Ile Leu His Gly
145                 150                 155                 160

Glu Ala Ser Ile Gly Gly Asn Gly Ser Met Asn Ser Gly Gly Val Phe
                165                 170                 175

Gly Asp Phe Gly Arg Ser Ser Gly Gly Lys Gln Glu Thr Gly Ser Glu
                180                 185                 190

Gly His Gly Thr Glu Thr Pro Met Tyr Leu Lys Gly Ser Glu Glu Glu
                195                 200                 205

Gly Asn
    210

<210> SEQ ID NO 11
<211> LENGTH: 591
<212> TYPE: DNA
<213> ORGANISM: Brassica napus

<400> SEQUENCE: 11
atgcagccca tgatggctgg ttactacccc agcaatgtca cctctgatca tatccagcag    60
tacttggatg agaacaagtc tttgattctg aagatagttg agtctcaaaa ctcaggaaag   120
ctcagcgagt gtgccgagaa tcaggcaagg cttcaacgca acctcatgta cttggctgca   180
atagcagatt ctcagcctca acctccaagc gtgcatagcc agtatggatc tgctggtggt   240
gggttgattc agggagaagg agcgtcacac tatttgcagc agcaacaggc gactcaacag   300
cagcagatga ctcagcagtc tcttatggca gctcgttctt caatgatgta tcagcagcag   360
caacagcctt atgcaacgct tcagcatcag cagttgcacc atagccagct tgggatgagc   420
tctagcagcg aggaggaag cagtggtctc catatccttc agggagaggc tggtgggttt   480
catgaatttg ccgtgggaa gccggagatg ggaagtggtg aaggcagggg tggaagctca   540
ggggatggtg gagaaacact ctacttgaag tcatcagatg atgggaactg a            591

<210> SEQ ID NO 12
<211> LENGTH: 203
<212> TYPE: PRT
<213> ORGANISM: Brassica napus

<400> SEQUENCE: 12

Met Gln Gln His Leu Met Gln Met Gln Pro Met Met Ala Gly Tyr Tyr
1                5                  10                  15

Pro Ser Asn Val Thr Ser Asp His Ile Gln Gln Tyr Leu Asp Glu Asn
                20                  25                  30

Lys Ser Leu Ile Leu Lys Ile Val Glu Ser Gln Asn Ser Gly Lys Leu
            35                  40                  45

Ser Glu Cys Ala Glu Asn Gln Ala Arg Leu Gln Arg Asn Leu Met Tyr
50                  55                  60

Leu Ala Ala Ile Ala Asp Ser Gln Pro Gln Pro Pro Ser Val His Ser
65                  70                  75                  80

Gln Tyr Gly Ser Ala Gly Gly Gly Leu Ile Gln Gly Glu Gly Ala Ser
                85                  90                  95

His Tyr Leu Gln Gln Gln Gln Ala Thr Gln Gln Gln Met Thr Gln
            100                 105                 110

Gln Ser Leu Met Ala Ala Arg Ser Ser Met Met Tyr Gln Gln Gln Gln
        115                 120                 125

Gln Pro Tyr Ala Thr Leu Gln His Gln Gln Leu His His Ser Gln Leu
    130                 135                 140

Gly Met Ser Ser Ser Gly Gly Ser Gly Leu His Ile Leu
145                 150                 155                 160

Gln Gly Glu Ala Gly Gly Phe His Glu Phe Gly Arg Gly Lys Pro Glu
                165                 170                 175

Met Gly Ser Gly Glu Gly Arg Gly Ser Ser Gly Asp Gly Glu
            180                 185                 190

Thr Leu Tyr Leu Lys Ser Ser Asp Asp Gly Asn
        195                 200

<210> SEQ ID NO 13
<211> LENGTH: 663
<212> TYPE: DNA
<213> ORGANISM: Citrus sinensis

<400> SEQUENCE: 13
atgcaacagc acctgatgca gatgcagccc atgatggcag cttattatcc caacaacgtc      60
actactgacc acattcaaca gtatctagat gagaacaaat cattgatttt gaagattgtt     120
gagagccaga attcagggaa actgagcgag tgtgcagaga ccaggcaag attgcagcgg      180 aatctcatgt acctggctgc tattgctgat gctcaacccc aaccacctag cgttcatgcc     240
cagttctctt ctggtggcat tatgcagcca ggagctcact atatgcaaca ccagcaatct     300
cagccaatga caccacagtc acttatggct gcacgctcat ccatggtgta ctctcaacag     360
caattttcag tgcttcagca acagcaagcc ttgcatggtc agcttggcat gagctctggt     420
ggtagctcag gacttcacat gctgcaaagt gagggtagta ctgcaggagg tagtggttca     480
cttgggggtg gggattccc tgattttggc cgtggctcat ctggtgaagg cttgcactca      540
aggggaatgg ggagcaagca tgatataggc agttctggat ctgctgaagg acgaggaggg     600
agctcaggaa gccaagatgg aggcgaaact ctctacttga aggggctga tgatggaaat      660 taa                                                                   663

<210> SEQ ID NO 14
<211> LENGTH: 219
<212> TYPE: PRT
<213> ORGANISM: Citrus sinensis

<400> SEQUENCE: 14

Met Gln Gln His Leu Met Gln Met Gln Pro Met Met Ala Ala Tyr Tyr
1               5                   10                  15

Pro Asn Asn Val Thr Thr Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ala Gln Pro Gln Pro Pro Ser Val His Ala
65                  70                  75                  80

Gln Phe Ser Ser Gly Gly Ile Met Gln Pro Gly Ala His Tyr Met Gln
                85                  90                  95

His Gln Gln Ser Gln Pro Met Thr Pro Gln Ser Leu Met Ala Ala Arg
            100                 105                 110

Ser Ser Met Val Tyr Ser Gln Gln Phe Ser Val Leu Gln Gln Gln
        115                 120                 125

Gln Ala Leu His Gly Gln Leu Gly Met Ser Ser Gly Gly Ser Ser Gly
    130                 135                 140

```
Leu His Met Leu Gln Ser Glu Gly Ser Thr Ala Gly Ser Gly Ser
145                 150                 155                 160

Leu Gly Gly Gly Phe Pro Asp Phe Gly Arg Gly Ser Ser Gly Glu
            165                 170                 175

Gly Leu His Ser Arg Gly Met Gly Ser Lys His Asp Ile Gly Ser Ser
        180                 185                 190

Gly Ser Ala Glu Gly Arg Gly Gly Ser Gly Ser Gln Asp Gly Gly
        195                 200                 205

Glu Thr Leu Tyr Leu Lys Gly Ala Asp Asp Gly
    210                 215
```

<210> SEQ ID NO 15
<211> LENGTH: 660
<212> TYPE: DNA
<213> ORGANISM: Gossypium arboreum
<220> FEATURE:
<221> NAME/KEY: misc_feature
<222> LOCATION: (309)..(309)
<223> OTHER INFORMATION: n is a, c, g, or t

<400> SEQUENCE: 15

```
atgcagcagc acctgatgca gatgcagccc atgatggcag cttattatcc caacaacgtc      60
actactgatc atattcaaca gtatctcgat gagaacaagt cattgatctt aaagattgtt     120
gagagccaga attctgggaa attgagtgaa tgtgctgaga accaagcaag gctgcagcga     180
aacctcatgt acctggctgc cattgcggat ctcaaccccc aaccacccac cgtgcatgca     240
cagtttccat ctggtggtat catgcagcaa ggagctgggc actacatgca gcaccaacaa     300
gctcaacana tgacacaaca gtcgcttatg gctgctcggt cctcaatgtt gtattctcag     360
caaccatttt ctgcactgca acaacaacaa caacaaggct tgcacagtc agcttggcat     420
gagctctggc gggagcacag gcctttcata tgctgcaaac tgaatctagt actgcagggg     480
gcagtgagac accttgggcc cgagggttgt cctgatttgg acgggggtct tttggagagg     540
catccctggt ggcaggccaa tggccggggg aacaaccaaa aatccgggga ggccggctca     600
cctaagggcc gggaggagcc cttggggcag ggggggtga tggggggaac ctcttcttaa     660
```

<210> SEQ ID NO 16
<211> LENGTH: 219
<212> TYPE: PRT
<213> ORGANISM: Gossypium arboreum
<220> FEATURE:
<221> NAME/KEY: misc_feature
<222> LOCATION: (103)..(103)
<223> OTHER INFORMATION: Xaa can be any naturally occurring amino acid

<400> SEQUENCE: 16

```
Met Gln Gln His Leu Met Gln Met Gln Pro Met Met Ala Ala Tyr Tyr
1               5                   10                  15

Pro Asn Asn Val Thr Thr Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ser Gln Pro Gln Pro Thr Val His Ala
65                  70                  75                  80

Gln Phe Pro Ser Gly Gly Ile Met Gln Gln Gly Ala Gly His Tyr Met
                85                  90                  95

Gln His Gln Gln Ala Gln Xaa Met Thr Gln Gln Ser Leu Met Ala Ala
```

```
              100                 105                 110
Arg Ser Ser Met Leu Tyr Ser Gln Gln Pro Phe Ser Ala Leu Gln Gln
            115                 120                 125

Gln Gln Gln Gln Gly Phe Ala Gln Ser Ala Trp His Glu Leu Trp Arg
        130                 135                 140

Glu His Arg Pro Phe Ile Cys Cys Lys Leu Asn Leu Val Leu Gln Gly
145                 150                 155                 160

Ala Val Arg His Leu Gly Pro Glu Gly Cys Pro Asp Leu Asp Gly Gly
                165                 170                 175

Leu Leu Glu Arg His Pro Trp Trp Gln Ala Asn Gly Arg Gly Asn Asn
            180                 185                 190

Gln Lys Ser Gly Glu Ala Gly Ser Pro Lys Gly Arg Glu Glu Pro Leu
        195                 200                 205

Gly Gln Gly Gly Val Met Gly Thr Ser Ser
    210                 215

<210> SEQ ID NO 17
<211> LENGTH: 636
<212> TYPE: DNA
<213> ORGANISM: Medicago trunculata

<400> SEQUENCE: 17
atgcagcagc acctgatgca gatgcagccc atgatggcag cttactatcc taacaacgtc      60
actactgatc atattcaaca gtatcttgat gagaacaagt ccttgattct caagattgtt     120
gaaagccaga cactggcaa gctcaccgag tgtgctgaga accaatcaag gcttcagaga      180
aatctcatgt acctagctgc aatagctgat tctcaacccc aaccacctac tatgcctggc     240
cagtacccct tcaagtggaat gatgcagcag ggaggacact catgcaggc tcaacaagct     300 cagcagatga cacaacaaca attaatggct gcacgttcct ctcttatgta tgctcaacag     360
cttcaacagc agcaagcctt gcaaagccaa cttggtatga attccagtgg aagtcaaggc     420
cttcacatgt tgcatagtga aggggctaat gttggaggca attcatctct aggggctggt     480
tttcctgatt ttggccgtag ctcagccggt gatggtttgc acggcagtgg taagcaagac     540
attggaagca ctgatggccg cggtggaagc tctagtggtc actctggtga tggcggcgaa     600
acactttacc tgaaatcttc tggtgatggg aattag                                636

<210> SEQ ID NO 18
<211> LENGTH: 211
<212> TYPE: PRT
<213> ORGANISM: Medicago trunculata

<400> SEQUENCE: 18

Met Gln Gln His Leu Met Gln Met Gln Pro Met Ala Ala Tyr Tyr
1               5                   10                  15

Pro Asn Asn Val Thr Thr Asp His Ile Gln Gln Tyr Leu Asp Glu Asn
                20                  25                  30

Lys Ser Leu Ile Leu Lys Ile Val Glu Ser Gln Asn Thr Gly Lys Leu
            35                  40                  45

Thr Glu Cys Ala Glu Asn Gln Ser Arg Leu Gln Arg Asn Leu Met Tyr
        50                  55                  60

Leu Ala Ala Ile Ala Asp Ser Gln Pro Gln Pro Pro Thr Met Pro Gly
65                  70                  75                  80

Gln Tyr Pro Ser Ser Gly Met Met Gln Gln Gly Gly His Tyr Met Gln
                85                  90                  95

Ala Gln Gln Ala Gln Gln Met Thr Gln Gln Gln Leu Met Ala Ala Arg
```

```
                   100                 105                 110
Ser Ser Leu Met Tyr Ala Gln Gln Leu Gln Gln Gln Ala Leu Gln
        115                 120                 125

Ser Gln Leu Gly Met Asn Ser Ser Gly Ser Gln Gly Leu His Met Leu
        130                 135                 140

His Ser Glu Gly Ala Asn Val Gly Gly Asn Ser Ser Leu Gly Ala Gly
145                 150                 155                 160

Phe Pro Asp Phe Gly Arg Ser Ser Ala Gly Asp Gly Leu His Gly Ser
                165                 170                 175

Gly Lys Gln Asp Ile Gly Ser Thr Asp Gly Arg Gly Gly Ser Ser Ser
            180                 185                 190

Gly His Ser Gly Asp Gly Gly Glu Thr Leu Tyr Leu Lys Ser Ser Gly
        195                 200                 205

Asp Gly Asn
    210

<210> SEQ ID NO 19
<211> LENGTH: 684
<212> TYPE: DNA
<213> ORGANISM: Oryza sativa

<400> SEQUENCE: 19
atgcagcagc aacacctgat gcagatgaac cagggcatga tggggggata tgcttcccct      60
accaccgtca ccactgatct cattcagcag tatctggatg agaacaagca gctgatcctg     120
gccatccttg acaaccagaa caatgggaag gtggaagagt gcgctcggaa ccaagctaag     180
ctccagcaca atctcatgta cctcgccgcc atcgccgaca gccagccgcc gcagacggcc     240
gccatgtccc agtatccgtc gaacctgatg atgcagtccg ggcgaggta catgccgcag      300 cagtcggcgc agatgatggc gccgcagtcg ctgatggcgg cgaggtcttc gatgatgtac     360
gcgcagccgg cgctgtcgcc gctccagcag cagcagcagc agcaggcggc ggcggcgcac     420
gggcagctgg gcatgggctc ggggggcacc accagcgggt tcagcatcct ccacggcgag     480
gccagcatgg gcggcggcgg cggcggcggt ggcgccggta acagcatgat gaacgccggc     540
gtgttctccg acttcggacg cggcggcggc ggcggcggca aggagggtc cacctcgctg      600 tccgtcgacg tccggggcgc caactccggc gcccagagcg cgacggggga gtacctcaag     660
ggcaccgagg aggaaggcag ctag                                             684

<210> SEQ ID NO 20
<211> LENGTH: 227
<212> TYPE: PRT
<213> ORGANISM: Oryza sativa

<400> SEQUENCE: 20

Met Gln Gln Gln His Leu Met Gln Met Asn Gln Gly Met Met Gly Gly
1               5                   10                  15

Tyr Ala Ser Pro Thr Thr Val Thr Thr Asp Leu Ile Gln Gln Tyr Leu
            20                  25                  30

Asp Glu Asn Lys Gln Leu Ile Leu Ala Ile Leu Asp Asn Gln Asn Asn
        35                  40                  45

Gly Lys Val Glu Glu Cys Ala Arg Asn Gln Ala Lys Leu Gln His Asn
    50                  55                  60

Leu Met Tyr Leu Ala Ala Ile Ala Asp Ser Gln Pro Pro Gln Thr Ala
65                  70                  75                  80

Ala Met Ser Gln Tyr Pro Ser Asn Leu Met Met Gln Ser Gly Ala Arg
                85                  90                  95
```

Tyr Met Pro Gln Gln Ser Ala Gln Met Met Ala Pro Gln Ser Leu Met
            100                 105                 110

Ala Ala Arg Ser Ser Met Met Tyr Ala Gln Pro Ala Leu Ser Pro Leu
        115                 120                 125

Gln Gln Gln Gln Gln Gln Ala Ala Ala His Gly Gln Leu Gly
    130                 135                 140

Met Gly Ser Gly Gly Thr Thr Ser Gly Phe Ser Ile Leu His Gly Glu
145                 150                 155                 160

Ala Ser Met Gly Gly Gly Gly Gly Gly Ala Gly Asn Ser Met
                165                 170                 175

Met Asn Ala Gly Val Phe Ser Asp Phe Gly Arg Gly Gly Gly Gly
            180                 185                 190

Gly Lys Glu Gly Ser Thr Ser Leu Ser Val Asp Val Arg Gly Ala Asn
        195                 200                 205

Ser Gly Ala Gln Ser Gly Asp Gly Glu Tyr Leu Lys Gly Thr Glu Glu
    210                 215                 220

Glu Gly Ser
225

<210> SEQ ID NO 21
<211> LENGTH: 558
<212> TYPE: DNA
<213> ORGANISM: Oryza sativa

<400> SEQUENCE: 21
atgcagcagc agccgatgcc gatgcccgcg caggcgccgc cgacggccgg aatcaccacc      60
gagcagatcc aaaagtatct ggatgaaaac aagcagctta ttttggctat tttggaaaat     120
cagaatctgg gaaagttggc agaatgtgct cagtatcaag cgcagcttca gaagaatctc     180
ttgtacttgg ctgcaattgc tgatactcaa ccgcagacca ctataagccg tccccagatg     240
gtgccgcatg gtgcatcgcc ggggttaggg gggcaataca tgtcgcaggt gccaatgttc     300
ccccccagga cccctctaac gccccagcag atgcaggagc agcagctgca gcaacagcaa     360
gcccagctgc tctcgttcgg cggtcagatg gttatgaggc ctggcgttgt gaatggcatt     420
cctcagcttc tgcaaggcga aatgcaccgc ggagcagatc accagaacgc tggcggggcc     480
acctcggagc cttccgagag ccacaggagc accggcaccg aaaatgacgg tggaagcgac     540
ttcggcgatc aatcctaa                                                    558

<210> SEQ ID NO 22
<211> LENGTH: 185
<212> TYPE: PRT
<213> ORGANISM: Oryza sativa

<400> SEQUENCE: 22

Met Gln Gln Gln Pro Met Pro Met Pro Ala Gln Ala Pro Pro Thr Ala
1               5                   10                  15

Gly Ile Thr Thr Glu Gln Ile Gln Lys Tyr Leu Asp Glu Asn Lys Gln
            20                  25                  30

Leu Ile Leu Ala Ile Leu Glu Asn Gln Asn Leu Gly Lys Leu Ala Glu
        35                  40                  45

Cys Ala Gln Tyr Gln Ala Gln Leu Gln Lys Asn Leu Leu Tyr Leu Ala
    50                  55                  60

Ala Ile Ala Asp Thr Gln Pro Gln Thr Thr Ile Ser Arg Pro Gln Met
65                  70                  75                  80

Val Pro His Gly Ala Ser Pro Gly Leu Gly Gly Gln Tyr Met Ser Gln

```
                    85                  90                  95
Val Pro Met Phe Pro Pro Arg Thr Pro Leu Thr Pro Gln Gln Met Gln
                100                 105                 110

Gln Gln Gln Leu Gln Gln Gln Ala Gln Leu Leu Ser Phe Gly Gly
            115                 120                 125

Gln Met Val Met Arg Pro Gly Val Val Asn Gly Ile Pro Gln Leu Leu
    130                 135                 140

Gln Gly Glu Met His Arg Gly Ala Asp His Gln Asn Ala Gly Gly Ala
145                 150                 155                 160

Thr Ser Glu Pro Ser Glu Ser His Arg Ser Thr Gly Thr Glu Asn Asp
                165                 170                 175

Gly Gly Ser Asp Phe Gly Asp Gln Ser
            180                 185

<210> SEQ ID NO 23
<211> LENGTH: 618
<212> TYPE: DNA
<213> ORGANISM: Oryza sativa

<400> SEQUENCE: 23
atgcagcagc agatggccat gccggcgggg gccgccgccg ccgcggtgcc gccggcggcc      60
ggcatcacca ccgagcagat ccaaaagtat ttggatgaaa ataaacagct aattttggcc     120
atcctggaaa atcaaaacct agggaagttg gctgaatgtg ctcagtacca agctcagctt     180
caaaagaatc tcttgtatct ggctgccatt gcagatgccc aaccacctca gaatccagga     240
agtcgccctc agatgatgca gcctggtgct accccaggtg ctgggcatta catgtcccaa     300
gtaccgatgt tccctccaag aactcccttt accccacaac agatgcaaga gcagcagcag     360
cagcaactcc agcaacagca agctcaggct ctagccttcc ccggccagat gctaatgaga     420
ccaggtactg tcaatggcat gcaatctatc ccagttgctg accctgctcg cgcagccgat     480
cttcagacgg cagcaccggg ctcggtagat ggccgaggaa acaagcagga tgcaacctcg     540
gagccttccg ggaccgagag ccacaagagt gcgggagcag ataacgacgc aggcggtgac     600
atagcggaga agtcctga                                                   618

<210> SEQ ID NO 24
<211> LENGTH: 205
<212> TYPE: PRT
<213> ORGANISM: Oryza sativa

<400> SEQUENCE: 24

Met Gln Gln Gln Met Ala Met Pro Ala Gly Ala Ala Ala Ala Ala Val
1               5                   10                  15

Pro Pro Ala Ala Gly Ile Thr Thr Glu Gln Ile Gln Lys Tyr Leu Asp
            20                  25                  30

Glu Asn Lys Gln Leu Ile Leu Ala Ile Leu Glu Asn Gln Asn Leu Gly
        35                  40                  45

Lys Leu Ala Glu Cys Ala Gln Tyr Gln Ala Gln Leu Gln Lys Asn Leu
    50                  55                  60

Leu Tyr Leu Ala Ala Ile Ala Asp Ala Gln Pro Pro Gln Asn Pro Gly
65                  70                  75                  80

Ser Arg Pro Gln Met Met Gln Pro Gly Ala Thr Pro Gly Ala Gly His
                85                  90                  95

Tyr Met Ser Gln Val Pro Met Phe Pro Pro Arg Thr Pro Leu Thr Pro
            100                 105                 110

Gln Gln Met Gln Glu Gln Gln Gln Gln Leu Gln Gln Gln Gln Ala
```

Gln Ala Leu Ala Phe Pro Gly Gln Met Leu Met Arg Pro Gly Thr Val
        130                 135                 140

Asn Gly Met Gln Ser Ile Pro Val Ala Asp Pro Ala Arg Ala Ala Asp
145                 150                 155                 160

Leu Gln Thr Ala Ala Pro Gly Ser Val Asp Gly Arg Gly Asn Lys Gln
                165                 170                 175

Asp Ala Thr Ser Glu Pro Ser Gly Thr Glu Ser His Lys Ser Ala Gly
            180                 185                 190

Ala Asp Asn Asp Ala Gly Gly Asp Ile Ala Glu Lys Ser
        195                 200                 205

<210> SEQ ID NO 25
<211> LENGTH: 540
<212> TYPE: DNA
<213> ORGANISM: Solanum tuberosum

<400> SEQUENCE: 25
atgcagcagc agcacctgat gcagatgcag cccatgatgg cagcctatta tcccaacaat    60
gtcactactg atcatattca acagttcctg gatgagaaca aatcacttat tctgaagatt   120
gttgagagcc agaactctgg gaaaataagt gaatgtgcag agtcccaagc taaacttcag   180
agaaatctta tgtaccttgc agctattgct gattcacagc cccagcctcc tagtatgcat   240
tcacagttag cttctggtgg gatgatgcag ggaggggcac attatatgca gcaacaacaa   300
gctcaacaac tcacaacgca atcgcttatg gctgcagcaa gatcctcctc ctcaatgctc   360
tatggacaac aacaacaaca caacaacaa caactatcat cattgcaaca acagcaagca   420
gcctttcata gccagcaact cggaatgagc agctctggtg gaggaagcag tagtggactt   480
cacatgctac aaagcgaaaa cactcatagt gctagcactg gtggtgggtg gtttccctga   540

<210> SEQ ID NO 26
<211> LENGTH: 179
<212> TYPE: PRT
<213> ORGANISM: Solanum tuberosum

<400> SEQUENCE: 26

Met Gln Gln Gln His Leu Met Gln Met Gln Pro Met Met Ala Ala Tyr
1               5                   10                  15

Tyr Pro Asn Asn Val Thr Thr Asp His Ile Gln Gln Phe Leu Asp Glu
            20                  25                  30

Asn Lys Ser Leu Ile Leu Lys Ile Val Glu Ser Gln Asn Ser Gly Lys
        35                  40                  45

Ile Ser Glu Cys Ala Glu Ser Gln Ala Lys Leu Gln Arg Asn Leu Met
50                  55                  60

Tyr Leu Ala Ala Ile Ala Asp Ser Gln Pro Gln Pro Pro Ser Met His
65                  70                  75                  80

Ser Gln Leu Ala Ser Gly Gly Met Met Gln Gly Gly Ala His Tyr Met
                85                  90                  95

Gln Gln Gln Gln Ala Gln Gln Leu Thr Thr Gln Ser Leu Met Ala Ala
            100                 105                 110

Ala Arg Ser Ser Ser Ser Met Leu Tyr Gly Gln Gln Gln Gln Gln Gln
        115                 120                 125

Gln Gln Gln Leu Ser Ser Leu Gln Gln Gln Ala Ala Phe His Ser
    130                 135                 140

Gln Gln Leu Gly Met Ser Ser Ser Gly Gly Gly Ser Ser Gly Leu
145                 150                 155                 160

His Met Leu Gln Ser Glu Asn Thr His Ser Ala Ser Thr Gly Gly Gly
              165                 170                 175

Trp Phe Pro

<210> SEQ ID NO 27
<211> LENGTH: 684
<212> TYPE: DNA
<213> ORGANISM: Zea mays

<400> SEQUENCE: 27
atgcagcagc aacacctgat gcagatgaac cagaacatga tggggggcta caccctctcct      60
gccgccgtga ccaccgatct catccagcag cacctggacg agaacaagca gctgatcctg     120
gccatcctcg acaaccagaa caatggcaag gcggaggagt gcgaacggca ccaagctaag     180
ctccagcaca acctcatgta cctggccgcc atcgctgaca gccagccgcc acagaccgcg     240
ccactatcac agtacccgtc caacctgatg atgcagccgg gccctcggta catgccaccg     300
cagtccgggc agatgatgaa cccgcagtcg ctgatggcgg cgcggtcctc catgatgtac     360
gcgcacccgt ccctgtcgcc actccagcag cagcaggcgg cgcacggaca gctgggtatg     420
gctccagggg gcggcggtgg cggcacgacc agcgggttca gcatcctcca cggcgaggcc     480
agcatgggcg gtggtggtgc tggcgcaggc gccggcaaca acatgatgaa cgccggcatg     540
ttctcgggct ttggccgcag cggcagtggc gccaaggaag ggtcgacctc tctgtcggtt     600
gacgtccggg gtggaaccag ctccggcgcg cagagcgggg acggcgagta cctcaaagtc     660
ggcaccgagg aagaaggcag ttag                                            684

<210> SEQ ID NO 28
<211> LENGTH: 227
<212> TYPE: PRT
<213> ORGANISM: Zea mays

<400> SEQUENCE: 28

Met Gln Gln Gln His Leu Met Gln Met Asn Gln Asn Met Met Gly Gly
1               5                   10                  15

Tyr Thr Ser Pro Ala Ala Val Thr Thr Asp Leu Ile Gln Gln His Leu
            20                  25                  30

Asp Glu Asn Lys Gln Leu Ile Leu Ala Ile Leu Asp Asn Gln Asn Asn
        35                  40                  45

Gly Lys Ala Glu Glu Cys Glu Arg His Gln Ala Lys Leu Gln His Asn
    50                  55                  60

Leu Met Tyr Leu Ala Ala Ile Ala Asp Ser Gln Pro Pro Gln Thr Ala
65                  70                  75                  80

Pro Leu Ser Gln Tyr Pro Ser Asn Leu Met Met Gln Pro Gly Pro Arg
                85                  90                  95

Tyr Met Pro Pro Gln Ser Gly Gln Met Met Asn Pro Gln Ser Leu Met
            100                 105                 110

Ala Ala Arg Ser Ser Met Met Tyr Ala His Pro Ser Leu Ser Pro Leu
        115                 120                 125

Gln Gln Gln Gln Ala Ala His Gly Gln Leu Gly Met Ala Pro Gly Gly
    130                 135                 140

Gly Gly Gly Gly Thr Thr Ser Gly Phe Ser Ile Leu His Gly Glu Ala
145                 150                 155                 160

Ser Met Gly Gly Gly Gly Ala Gly Ala Gly Ala Gly Asn Asn Met Met
                165                 170                 175

Asn Ala Gly Met Phe Ser Gly Phe Gly Arg Ser Gly Ser Gly Ala Lys

```
                180              185              190
Glu Gly Ser Thr Ser Leu Ser Val Asp Val Arg Gly Gly Thr Ser Ser
                195              200              205
Gly Ala Gln Ser Gly Asp Gly Glu Tyr Leu Lys Val Gly Thr Glu Glu
    210              215              220
Glu Gly Ser
225

<210> SEQ ID NO 29
<211> LENGTH: 549
<212> TYPE: DNA
<213> ORGANISM: Zea mays

<400> SEQUENCE: 29
atgcagcagc cgatgcacat gcagccacag gcgccggcga taaccccagc tgccggaatc    60
agcacggagc agatccaaaa gtatctggat gagaataagc agcttatttt ggctattttg   120
gaaaatcaga acctaggaaa attggcagaa tgtgctcagt atcaatcaca acttcagaag   180
aacctcttgt atctcgctgc aatcgcagat gctcaaccgc agactgctgt aagccgccct   240
cagatggcgc cgcctggtgg atcgcctgga gtagggcagt acatgtcaca ggtgcctatg   300
ttcccaccga ggacacctct tacaccccag cagatgcagg agcagcagct tcagcagcag   360
caggctcagt tgctaaactt cagtggccaa atggttgcta gaccaggcat ggtcaacggc   420
atggctcagt ccatgcaagc tcagctacca ccgggtgtga acaagcagga tgctggtggg   480
gtcgcctctg agccctcggg caccgagagc cacaggagca ctggtggtga cgatggtgga   540
agcgactag                                                            549

<210> SEQ ID NO 30
<211> LENGTH: 182
<212> TYPE: PRT
<213> ORGANISM: Zea mays

<400> SEQUENCE: 30

Met Gln Gln Pro Met His Met Gln Pro Gln Ala Pro Ala Ile Thr Pro
1               5                   10                  15

Ala Ala Gly Ile Ser Thr Glu Gln Ile Gln Lys Tyr Leu Asp Glu Asn
                20                  25                  30

Lys Gln Leu Ile Leu Ala Ile Leu Glu Asn Gln Asn Leu Gly Lys Leu
            35                  40                  45

Ala Glu Cys Ala Gln Tyr Gln Ser Gln Leu Gln Lys Asn Leu Leu Tyr
        50                  55                  60

Leu Ala Ala Ile Ala Asp Ala Gln Pro Gln Thr Ala Val Ser Arg Pro
65                  70                  75                  80

Gln Met Ala Pro Pro Gly Gly Ser Pro Gly Val Gly Gln Tyr Met Ser
                85                  90                  95

Gln Val Pro Met Phe Pro Pro Arg Thr Pro Leu Thr Pro Gln Gln Met
                100                 105                 110

Gln Glu Gln Gln Leu Gln Gln Gln Ala Gln Leu Leu Asn Phe Ser
            115                 120                 125

Gly Gln Met Val Ala Arg Pro Gly Met Val Asn Gly Met Ala Gln Ser
        130                 135                 140

Met Gln Ala Gln Leu Pro Pro Gly Val Asn Lys Gln Asp Ala Gly Gly
145                 150                 155                 160

Val Ala Ser Glu Pro Ser Gly Thr Glu Ser His Arg Ser Thr Gly Gly
                165                 170                 175
```

Asp Asp Gly Gly Ser Asp
                180

<210> SEQ ID NO 31
<211> LENGTH: 1173
<212> TYPE: DNA
<213> ORGANISM: Homo sapiens

<400> SEQUENCE: 31
atgggcggca acatgtctgt ggctttcgcg gccccgaggc agcgaggcaa gggggagatc      60
actcccgctg cgattcagaa gatgttggat gacaataacc atcttattca gtgtataatg     120
gactctcaga ataaaggaaa gacctcagag tgttctcagt atcagcagat gttgcacaca     180
aacttggtat accttgctac aatagcagat tctaatcaaa atatgcagtc tcttttacca     240
gcaccaccca cacagaatat gcctatgggt cctggaggga tgaatcagag cggccctccc     300
ccacctccac gctctcacaa catgccttca gatggaatgg taggtggggg tcctcctgca     360
ccgcacatgc agaaccagat gaacggccag atgcctgggc taaccatat gcctatgcag     420 ggacctggac ccaatcaact caatatgaca aacagttcca tgaatatgcc ttcaagtagc     480
catggatcca tgggaggtta caaccattct gtgccatcat cacagagcat gccagtacag     540
aatcagatga caatgagtca gggacaacca atgggaaact atggtccag accaaatatg     600 agtatgcagc aaaccaagg tccaatgatg catcagcagc tccttctca gcaatacaat     660 atgccacagg gaggcggaca gcattaccaa ggacagcagc cacctatggg aatgatgggt     720
caagttaacc aaggcaatca tatgatgggt cagagacaga ttcctcccta tagacctcct     780
caacagggcc caccacagca gtactcaggc caggaagact attacgggga ccaatacagt     840
catggtggac aaggtcctcc agaaggcatg aaccagcaat attaccctga tggaaattca     900
cagtatggcc aacagcaaga tgcataccag ggaccacctc acaacaggg atatccaccc     960 cagcagcagc agtacccagg cagcaaggt tacccaggac agcagcaggg ctacggtcct    1020
tcacagggtg gtccaggtcc tcagtatcct aactacccac agggacaagg tcagcagtat    1080
ggaggatata gaccaacaca gcctggacca ccacagccac cccagcagag gccttatgga    1140
tatgaccagg gacagtatgg aaattaccag cag                                 1173

<210> SEQ ID NO 32
<211> LENGTH: 391
<212> TYPE: PRT
<213> ORGANISM: Homo sapiens

<400> SEQUENCE: 32

Met Gly Gly Asn Met Ser Val Ala Phe Ala Ala Pro Arg Gln Arg Gly
1               5                   10                  15

Lys Gly Glu Ile Thr Pro Ala Ala Ile Gln Lys Met Leu Asp Asp Asn
            20                  25                  30

Asn His Leu Ile Gln Cys Ile Met Asp Ser Gln Asn Lys Gly Lys Thr
        35                  40                  45

Ser Glu Cys Ser Gln Tyr Gln Gln Met Leu His Thr Asn Leu Val Tyr
    50                  55                  60

Leu Ala Thr Ile Ala Asp Ser Asn Gln Asn Met Gln Ser Leu Leu Pro
65                  70                  75                  80

Ala Pro Pro Thr Gln Asn Met Pro Met Gly Pro Gly Gly Met Asn Gln
                85                  90                  95

Ser Gly Pro Pro Pro Pro Arg Ser His Asn Met Pro Ser Asp Gly
            100                 105                 110

```
Met Val Gly Gly Gly Pro Pro Ala Pro His Met Gln Asn Gln Met Asn
            115                 120                 125
Gly Gln Met Pro Gly Pro Asn His Met Pro Met Gln Gly Pro Gly Pro
    130                 135                 140
Asn Gln Leu Asn Met Thr Asn Ser Ser Met Asn Met Pro Ser Ser Ser
145                 150                 155                 160
His Gly Ser Met Gly Gly Tyr Asn His Ser Val Pro Ser Ser Gln Ser
                165                 170                 175
Met Pro Val Gln Asn Gln Met Thr Met Ser Gln Gly Gln Pro Met Gly
            180                 185                 190
Asn Tyr Gly Pro Arg Pro Asn Met Ser Met Gln Pro Asn Gln Gly Pro
        195                 200                 205
Met Met His Gln Gln Pro Pro Ser Gln Gln Tyr Asn Met Pro Gln Gly
    210                 215                 220
Gly Gly Gln His Tyr Gln Gly Gln Pro Pro Met Gly Met Met Gly
225                 230                 235                 240
Gln Val Asn Gln Gly Asn His Met Met Gly Gln Arg Gln Ile Pro Pro
                245                 250                 255
Tyr Arg Pro Pro Gln Gln Gly Pro Pro Gln Gln Tyr Ser Gly Gln Glu
            260                 265                 270
Asp Tyr Tyr Gly Asp Gln Tyr Ser His Gly Gly Gln Gly Pro Pro Glu
        275                 280                 285
Gly Met Asn Gln Gln Tyr Tyr Pro Asp Gly Asn Ser Gln Tyr Gly Gln
    290                 295                 300
Gln Gln Asp Ala Tyr Gly Pro Pro Gln Gln Gly Tyr Pro Pro
305                 310                 315                 320
Gln Gln Gln Gln Tyr Pro Gly Gln Gln Gly Tyr Pro Gly Gln Gln Gln
                325                 330                 335
Gly Tyr Gly Pro Ser Gln Gly Gly Pro Gly Pro Gln Tyr Pro Asn Tyr
            340                 345                 350
Pro Gln Gly Gln Gly Gln Gln Tyr Gly Gly Tyr Arg Pro Thr Gln Pro
        355                 360                 365
Gly Pro Pro Gln Pro Gln Gln Arg Pro Tyr Gly Tyr Asp Gln Gly
    370                 375                 380
Gln Tyr Gly Asn Tyr Gln Gln
385                 390

<210> SEQ ID NO 33
<211> LENGTH: 627
<212> TYPE: DNA
<213> ORGANISM: Allium cepa

<400> SEQUENCE: 33
atgcagcagc cgcagccagc gatgggaacc atgggctcgg tgccacctac tagcatcacc        60
accgaacaga ttcaaaggta cttggatgag aacaaacagt taatattggc aattttggat       120
aatcaaaatt taggaagact gaatgagtgt gctcaatatc aagctcagct tcaaaagaat       180
ctgctttacc tggcagcaat agctgatgct cagcctcagt ctcctgcggt gcgtctgcag       240
atgatgcctc aaggtgcagc tgccacgcct caagctggaa accaatttat gcagcagcag       300
agccctaatt tccctcccaa aacaggaatg caatttactc ctcaacaagt acaagaattg       360
cagcagcaac agctacaaca tcagccacat atgatgcctc catttcaagg tcaaatgggt       420
atgagaccta tgaatggaat gcaggcagca atgcatgcag attcatctct tgcttataac       480
actaacaata agcaagatgc aggaaacgca gcttatgaaa atactgctgc caacacagat       540
```

```
ggttccattc aaaagaaaac agcaaatgat gatttagacc cttctgcagc aaaccctaga    600
aggtctgaag atgccaaatc atcatga                                        627
```

<210> SEQ ID NO 34
<211> LENGTH: 208
<212> TYPE: PRT
<213> ORGANISM: Allium cepa

<400> SEQUENCE: 34

```
Met Gln Gln Pro Gln Pro Ala Met Gly Thr Met Gly Ser Val Pro Pro
1               5                   10                  15

Thr Ser Ile Thr Thr Glu Gln Ile Gln Arg Tyr Leu Asp Glu Asn Lys
            20                  25                  30

Gln Leu Ile Leu Ala Ile Leu Asp Asn Gln Asn Leu Gly Arg Leu Asn
        35                  40                  45

Glu Cys Ala Gln Tyr Gln Ala Gln Leu Gln Lys Asn Leu Leu Tyr Leu
    50                  55                  60

Ala Ala Ile Ala Asp Ala Gln Pro Gln Ser Pro Ala Val Arg Leu Gln
65                  70                  75                  80

Met Met Pro Gln Gly Ala Ala Thr Pro Gln Ala Gly Asn Gln Phe
                85                  90                  95

Met Gln Gln Gln Ser Pro Asn Phe Pro Pro Lys Thr Gly Met Gln Phe
            100                 105                 110

Thr Pro Gln Gln Val Gln Glu Leu Gln Gln Gln Leu Gln His Gln
        115                 120                 125

Pro His Met Met Pro Pro Phe Gln Gly Gln Met Gly Met Arg Pro Met
    130                 135                 140

Asn Gly Met Gln Ala Ala Met His Ala Asp Ser Ser Leu Ala Tyr Asn
145                 150                 155                 160

Thr Asn Asn Lys Gln Asp Ala Gly Asn Ala Ala Tyr Glu Asn Thr Ala
                165                 170                 175

Ala Asn Thr Asp Gly Ser Ile Gln Lys Lys Thr Ala Asn Asp Asp Leu
            180                 185                 190

Asp Pro Ser Ala Ala Asn Pro Arg Arg Ser Glu Asp Ala Lys Ser Ser
        195                 200                 205
```

<210> SEQ ID NO 35
<211> LENGTH: 633
<212> TYPE: DNA
<213> ORGANISM: Aquilegia formosa x Aquilegia pubescens

<400> SEQUENCE: 35

```
atgcaacaca tgcagatgca gcccatgatg ccaccttata gtgccaacag cgtcactact    60
gatcatatcc aacagtactt ggatgaaaat aaggcgttga ttctgaagat acttgagaac   120
caaaattcgg gaaaagttag tgaatgtgca gagaaccaag caagacttca acgaaatctt   180
atgtatctgg ctgcaattgc tgattctcaa ccacagcctc caatatgca tgctcagtac    240 tctaatgcgg gtataccacc tggtgcacat tacctacaac accaacaggc ccaacagatg   300
acacaacagt cgctcatggc tgctcgatca aatatgctgt atgctcagcc aatcacagga   360
atgcagcaac agcaagcaat gcatagccag cttggcatga gctctggtgg taacagtgga   420
ctccacatga tgcacaatga gggcagcatg ggaggtagtg gggcacttgg aagctattct   480
gattatggcc gtggcagtgg tggtggagta actatcgcta gcaaacaaga tggtggaagt   540
ggttctggtg aaggacgagg tggaaactct ggaggccaaa gtgcagatgg aggtgaatct   600
ctttacctga aaaacagtga cgaagggaac taa                                633
```

<210> SEQ ID NO 36
<211> LENGTH: 210
<212> TYPE: PRT
<213> ORGANISM: Aquilegia formosa x Aquilegia pubescens

<400> SEQUENCE: 36

```
Met Gln His Met Gln Met Gln Pro Met Met Pro Pro Tyr Ser Ala Asn
1               5                   10                  15

Ser Val Thr Thr Asp His Ile Gln Gln Tyr Leu Asp Glu Asn Lys Ala
            20                  25                  30

Leu Ile Leu Lys Ile Leu Glu Asn Gln Asn Ser Gly Lys Val Ser Glu
        35                  40                  45

Cys Ala Glu Asn Gln Ala Arg Leu Gln Arg Asn Leu Met Tyr Leu Ala
50                  55                  60

Ala Ile Ala Asp Ser Gln Pro Gln Pro Pro Asn Met His Ala Gln Tyr
65                  70                  75                  80

Ser Asn Ala Gly Ile Pro Pro Gly Ala His Tyr Leu Gln His Gln Gln
                85                  90                  95

Ala Gln Gln Met Thr Gln Gln Ser Leu Met Ala Ala Arg Ser Asn Met
            100                 105                 110

Leu Tyr Ala Gln Pro Ile Thr Gly Met Gln Gln Gln Gln Ala Met His
        115                 120                 125

Ser Gln Leu Gly Met Ser Ser Gly Gly Asn Ser Gly Leu His Met Met
130                 135                 140

His Asn Glu Gly Ser Met Gly Gly Ser Gly Ala Leu Gly Ser Tyr Ser
145                 150                 155                 160

Asp Tyr Gly Arg Gly Ser Gly Gly Gly Val Thr Ile Ala Ser Lys Gln
                165                 170                 175

Asp Gly Gly Ser Gly Ser Gly Glu Gly Arg Gly Gly Asn Ser Gly Gly
            180                 185                 190

Gln Ser Ala Asp Gly Gly Glu Ser Leu Tyr Leu Lys Asn Ser Asp Glu
        195                 200                 205

Gly Asn
    210
```

<210> SEQ ID NO 37
<211> LENGTH: 615
<212> TYPE: DNA
<213> ORGANISM: Brachypodium distachyon

<400> SEQUENCE: 37

```
atgcagcagg cgatgtccat gtccccgggg tcggccggcg cggtgccgcc tccggccggc    60
atcaccacag agcagatcca aaagtatttg gatgaaaata gcaacttat tttggccatc     120 ctggaaaatc agaacctagg aaagttgact gaatgtgctc agtatcaagc tcaacttcag    180
aagaatctct tgtatctggc tgccattgcg gatgcccaac caccacagaa ccctggaagt    240 cgccccccaga tggtgcagcc tggtggtatg ccaggtgcag gcattacat gtcgcaagta    300 ccaatgttcc ctccaagaac ccctttaacc ccacaacaga tgcaagagca acagcaccag    360
cagcttcagc agcagcaagc acaggctctt gctttcccca gccagatggt catgagacca    420
ggtactgtga acggcatgca gcctatgcaa gctgatctcc aagcagcagc agcagcacct    480
ggcctggcag acagccgagg aagtaagcag gacgcagcgg tagctggggc catctcggaa    540
ccttctggca ccgagagtca aagagtaca ggagcggatc atgaggcagg tggcgatgta    600
gctgagcaat cctaa                                                     615
```

<210> SEQ ID NO 38
<211> LENGTH: 204
<212> TYPE: PRT
<213> ORGANISM: Brachypodium distachyon

<400> SEQUENCE: 38

```
Met Gln Gln Ala Met Ser Met Ser Pro Gly Ser Ala Gly Ala Val Pro
1               5                   10                  15

Pro Pro Ala Gly Ile Thr Thr Glu Gln Ile Gln Lys Tyr Leu Asp Glu
            20                  25                  30

Asn Lys Gln Leu Ile Leu Ala Ile Leu Glu Asn Gln Asn Leu Gly Lys
        35                  40                  45

Leu Thr Glu Cys Ala Gln Tyr Gln Ala Gln Leu Gln Lys Asn Leu Leu
    50                  55                  60

Tyr Leu Ala Ala Ile Ala Asp Ala Gln Pro Pro Gln Asn Pro Gly Ser
65                  70                  75                  80

Arg Pro Gln Met Val Gln Pro Gly Gly Met Pro Ala Gly His Tyr
                85                  90                  95

Met Ser Gln Val Pro Met Phe Pro Pro Arg Thr Pro Leu Thr Pro Gln
                100                 105                 110

Gln Met Gln Glu Gln Gln His Gln Leu Gln Gln Gln Ala Gln
            115                 120                 125

Ala Leu Ala Phe Pro Ser Gln Met Val Met Arg Pro Gly Thr Val Asn
        130                 135                 140

Gly Met Gln Pro Met Gln Ala Asp Leu Gln Ala Ala Ala Ala Pro
145                 150                 155                 160

Gly Leu Ala Asp Ser Arg Gly Ser Lys Gln Asp Ala Ala Val Ala Gly
                165                 170                 175

Ala Ile Ser Glu Pro Ser Gly Thr Glu Ser His Lys Ser Thr Gly Ala
            180                 185                 190

Asp His Glu Ala Gly Gly Asp Val Ala Glu Gln Ser
        195                 200
```

<210> SEQ ID NO 39
<211> LENGTH: 636
<212> TYPE: DNA
<213> ORGANISM: Brassica napus

<400> SEQUENCE: 39

```
atgcagcagc agcagcagca gcagcagcag cctccgcaaa tgtttccgat ggctccttcg    60
atgccgccaa ctaacatcac caccgaacag atccaaaagt accttgagga gaacaagaag   120
ctgataatgg caatcatgga aaatcagaat cttggcaagc ttgcagagtg tgcacagtac   180
caagctcttc tccagaagaa cttaatgtac ctcgctgcta ttgctgatgc tcaacctcct   240
ccatctaccg ctggagctac accaccacca gctatggctt cccagatggg ggcaccgcat   300
cctgggatgc aaccgccgag ctactttatg caacacccac aagcttcagg gatggctcaa   360
caagcaccac ccgctggtat cttccctccg agaggtcctt tgcagtttgg tagcccacac   420
cagcttcagg atccgcaaca gcagcatatg catcaacagg ctatgcaagg acacatgggg   480
atgcgaccaa tgggtatcaa caacaacaat gggatgcagc atcagatgca gcaacaacaa   540 ccagaaaacct ctcttggagg aagcgctgca acgtggggc ttagaggtgg aaagcaagat   600
ggagcagatg gacaaggaaa agatgatggc aaatga                             636
```

<210> SEQ ID NO 40

<211> LENGTH: 203
<212> TYPE: PRT
<213> ORGANISM: Brassica napus

<400> SEQUENCE: 40

| Met | Gln | Gln | His | Leu | Met | Gln | Met | Gln | Pro | Met | Met | Ala | Gly | Tyr | Tyr |
|---|---|---|---|---|---|---|---|---|---|---|---|---|---|---|---|
| 1 | | | | 5 | | | | | 10 | | | | | 15 | |

| Pro | Ser | Asn | Val | Thr | Ser | Asp | His | Ile | Gln | Gln | Tyr | Leu | Asp | Glu | Asn |
| | | | 20 | | | | | 25 | | | | | 30 | | |

| Lys | Ser | Leu | Ile | Leu | Lys | Ile | Val | Glu | Ser | Gln | Asn | Ser | Gly | Lys | Leu |
| | | | 35 | | | | 40 | | | | | 45 | | | |

| Ser | Glu | Cys | Ala | Glu | Asn | Gln | Ala | Arg | Leu | Gln | Arg | Asn | Leu | Met | Tyr |
| | 50 | | | | | 55 | | | | | 60 | | | | |

| Leu | Ala | Ala | Ile | Ala | Asp | Ser | Gln | Pro | Gln | Pro | Ser | Val | His | Ser |
| 65 | | | | | 70 | | | | 75 | | | | | 80 |

| Gln | Tyr | Gly | Ser | Ala | Gly | Gly | Leu | Ile | Gln | Gly | Glu | Ala | Ser |
| | | | | 85 | | | | 90 | | | | 95 | |

| His | Tyr | Leu | Gln | Gln | Gln | Ala | Thr | Gln | Gln | Gln | Met | Thr | Gln |
| | | | 100 | | | | 105 | | | | 110 | | |

| Gln | Ser | Leu | Met | Ala | Ala | Arg | Ser | Ser | Met | Met | Tyr | Gln | Gln | Gln |
| | | 115 | | | | | 120 | | | | | 125 | | |

| Gln | Pro | Tyr | Ala | Thr | Leu | Gln | His | Gln | Gln | Leu | His | His | Ser | Gln | Leu |
| | 130 | | | | | 135 | | | | | 140 | | | | |

| Gly | Met | Ser | Ser | Ser | Ser | Gly | Gly | Ser | Ser | Gly | Leu | His | Ile | Leu |
| 145 | | | | | 150 | | | | | 155 | | | | 160 |

| Gln | Gly | Glu | Ala | Gly | Gly | Phe | His | Glu | Phe | Gly | Arg | Gly | Lys | Pro | Glu |
| | | | | 165 | | | | | 170 | | | | | 175 | |

| Met | Gly | Ser | Gly | Glu | Gly | Arg | Gly | Gly | Ser | Ser | Gly | Asp | Gly | Gly | Glu |
| | | | 180 | | | | | 185 | | | | | 190 | | |

| Thr | Leu | Tyr | Leu | Lys | Ser | Ser | Asp | Asp | Gly | Asn |
| | | | 195 | | | | | 200 | | |

<210> SEQ ID NO 41
<211> LENGTH: 636
<212> TYPE: DNA
<213> ORGANISM: Citrus sinensis

<400> SEQUENCE: 41

```
atgcagcagc accgcaaat gatccctgtt atgccttcat ttccacccac caacatcacc        60
acagagcaga ttcaaaagta ccttgatgag aacaaaaagt tgattttggc aattttggac      120
aatcaaaatc ttggaaagct tacagaatgt gcccactatc aagctcagct tcaaaagaat      180
ttaatgtatt tagctgcaat tgctgatgca caaccacaag caccaacaat gcctcctcag      240
atggctccac atcctgcaat gcaagctagt gggtattaca tgcaacatcc tcaggcggca      300
gcaatggctc agcaacaagg aatctttccc caaaagatgc cattacaatt caataaccct      360
catcaactac aggatcctca acagcagcta caccaacatc aagccatgca agcacaaatg      420
ggaatgagac cggtgccac taacaatggt atgcatccca tgcatgctga aagctctctt       480
ggaggtggca gcagtggagg accccttca gcatcaggcc caggtgacat acgtggtgga       540
aataagcaag atgcctcgga ggctgggact actggtgctg atggccaggg cagttcggct      600
ggtgggcatg gtgggatgg agaggaggca aagtga                                 636
```

<210> SEQ ID NO 42
<211> LENGTH: 211
<212> TYPE: PRT
<213> ORGANISM: Citrus sinensis

<400> SEQUENCE: 42

| | | | | | | | | | | | | | | |
|---|---|---|---|---|---|---|---|---|---|---|---|---|---|---|
|Met|Gln|Gln|Pro|Pro|Gln|Met|Ile|Pro|Val|Met|Pro|Ser|Phe|Pro|Pro|
|1| | | |5| | | |10| | | |15| | |

Thr Asn Ile Thr Thr Glu Gln Ile Gln Lys Tyr Leu Asp Glu Asn Lys
            20                  25                  30

Lys Leu Ile Leu Ala Ile Leu Asp Asn Gln Asn Leu Gly Lys Leu Thr
        35                  40                  45

Glu Cys Ala His Tyr Gln Ala Gln Leu Gln Lys Asn Leu Met Tyr Leu
    50                  55                  60

Ala Ala Ile Ala Asp Ala Gln Pro Gln Ala Pro Thr Met Pro Pro Gln
65                  70                  75                  80

Met Ala Pro His Pro Ala Met Gln Ala Ser Gly Tyr Tyr Met Gln His
                85                  90                  95

Pro Gln Ala Ala Ala Met Ala Gln Gln Gly Ile Phe Pro Gln Lys
            100                 105                 110

Met Pro Leu Gln Phe Asn Asn Pro His Gln Leu Gln Asp Pro Gln Gln
        115                 120                 125

Gln Leu His Gln His Gly Ala Met Gln Ala Gln Met Gly Met Arg Pro
    130                 135                 140

Gly Ala Thr Asn Asn Gly Met His Pro Met His Ala Glu Ser Ser Leu
145                 150                 155                 160

Gly Gly Gly Ser Ser Gly Gly Pro Pro Ser Ala Ser Gly Pro Gly Asp
                165                 170                 175

Ile Arg Gly Gly Asn Lys Gln Asp Ala Ser Glu Ala Gly Thr Thr Gly
            180                 185                 190

Ala Asp Gly Gln Gly Ser Ser Ala Gly Gly His Gly Gly Asp Gly Glu
        195                 200                 205

Glu Ala Lys
    210

<210> SEQ ID NO 43
<211> LENGTH: 597
<212> TYPE: DNA
<213> ORGANISM: Euphorbia esula

<400> SEQUENCE: 43

```
atgcagcagc aaccgcagat gatgcctatg atgccttcat atccaccagc aaacattacc      60
acggagcaaa tccaaaagta tcttgatgaa aataaaaaat tgattttggc gatcttggat     120
aatcaaaatc ttggaaaact cgctgagtgt gcacagtatc aagccctgct gcaaaaaaat     180
ctgatgtatt tagccgcaat tgctgatgca caaccccaga ccccacccat gccacctcag     240
atgtccccac atccggctat gcaacaagga gcatattaca tgcaacatcc tcaggctgca     300
gcagcagcaa tggctcatca gtcgggtatt ttcccaccaa agatgtctcc gttacaattc     360
aataatcctc atcaaataca ggaccccag cagttacatc aagcagccct ccaagggcaa     420
atgggaatga ggcccatggg cccaataac gggatgcatc cgatgcaccc cgaggcaaat     480
cttggaggat ctaatgatgg tcgtggagga acaaacagg atgctccgga acgggagca     540
tcgggaggtg atgggcaagg caattctggt ggtgatgggg ctgaagatgg gaaatga      597
```

<210> SEQ ID NO 44
<211> LENGTH: 198
<212> TYPE: PRT
<213> ORGANISM: Euphorbia esula

<400> SEQUENCE: 44

Met Gln Gln Pro Gln Met Met Pro Met Met Pro Ser Tyr Pro Pro
1               5                   10                  15

Ala Asn Ile Thr Thr Glu Gln Ile Gln Lys Tyr Leu Asp Glu Asn Lys
        20                  25                  30

Lys Leu Ile Leu Ala Ile Leu Asp Asn Gln Asn Leu Gly Lys Leu Ala
            35                  40                  45

Glu Cys Ala Gln Tyr Gln Ala Leu Leu Gln Lys Asn Leu Met Tyr Leu
50                  55                  60

Ala Ala Ile Ala Asp Ala Gln Pro Gln Thr Pro Pro Met Pro Pro Gln
65                  70                  75                  80

Met Ser Pro His Pro Ala Met Gln Gln Gly Ala Tyr Tyr Met Gln His
                85                  90                  95

Pro Gln Ala Ala Ala Ala Met Ala His Gln Ser Gly Ile Phe Pro
            100                 105                 110

Pro Lys Met Ser Pro Leu Gln Phe Asn Asn Pro His Gln Ile Gln Asp
        115                 120                 125

Pro Gln Gln Leu His Gln Ala Ala Leu Gln Gly Gln Met Gly Met Arg
    130                 135                 140

Pro Met Gly Pro Asn Asn Gly Met His Pro Met His Pro Glu Ala Asn
145                 150                 155                 160

Leu Gly Gly Ser Asn Asp Gly Arg Gly Gly Asn Lys Gln Asp Ala Pro
                165                 170                 175

Glu Thr Gly Ala Ser Gly Gly Asp Gly Gln Gly Asn Ser Gly Gly Asp
            180                 185                 190

Gly Ala Glu Asp Gly Lys
        195

<210> SEQ ID NO 45
<211> LENGTH: 642
<212> TYPE: DNA
<213> ORGANISM: Glycine max

<400> SEQUENCE: 45
atgcagcaga caccgccaat gattcctatg atgccttctt tcccacctac gaacataacc      60
accgagcaga ttcaaaaata ccttgatgag aacaagaagc tgattctggc aatattggac    120
aatcaaaatc ttggaaaact tgcagaatgt gcccagtacc aagctcagct tcaaaagaat    180
ttgatgtatt tagctgcaat tgctgatgcc cagcctcaaa ccccggccat gcctccgcag    240
atggcaccgc accctgccat gcaaccagga ttctatatgc aacatcctca ggctgctgca    300
gcagcaatgg ctcagcagca gcaaggaatg ttcccccaga aaatgccatt gcaatttggc    360
aatccacatc aaatgcagga acaacaacag cagctacacc agcaggccat ccaaggtcaa    420
atgggactta gacctggaga tataaataat ggcatgcatc caatgcacag tgaggctgct    480 cttgaggtg aaacagcgg tggtccacct tcggctactg gtccaaacga tgcacgtggt    540
ggaagcaagc aagatgcctc tgaggctgga acagctggtg agacggcca aggcagctcc    600 gcggctgctc ataacagtgg agatggtgaa gaggcaaagt ga                        642

<210> SEQ ID NO 46
<211> LENGTH: 213
<212> TYPE: PRT
<213> ORGANISM: Glycine max

<400> SEQUENCE: 46

Met Gln Gln Thr Pro Pro Met Ile Pro Met Met Pro Ser Phe Pro Pro
1               5                   10                  15

Thr Asn Ile Thr Thr Glu Gln Ile Gln Lys Tyr Leu Asp Glu Asn Lys
            20                  25                  30

Lys Leu Ile Leu Ala Ile Leu Asp Asn Gln Asn Leu Gly Lys Leu Ala
        35                  40                  45

Glu Cys Ala Gln Tyr Gln Ala Gln Leu Gln Lys Asn Leu Met Tyr Leu
    50                  55                  60

Ala Ala Ile Ala Asp Ala Gln Pro Gln Thr Pro Ala Met Pro Pro Gln
65                  70                  75                  80

Met Ala Pro His Pro Ala Met Gln Pro Gly Phe Tyr Met Gln His Pro
                85                  90                  95

Gln Ala Ala Ala Ala Met Ala Gln Gln Gln Gly Met Phe Pro
            100                 105                 110

Gln Lys Met Pro Leu Gln Phe Gly Asn Pro His Gln Met Gln Glu Gln
            115                 120                 125

Gln Gln Gln Leu His Gln Ala Ile Gln Gly Gln Met Gly Leu Arg
        130                 135                 140

Pro Gly Asp Ile Asn Asn Gly Met His Pro Met His Ser Glu Ala Ala
145                 150                 155                 160

Leu Gly Gly Gly Asn Ser Gly Gly Pro Pro Ser Ala Thr Gly Pro Asn
                165                 170                 175

Asp Ala Arg Gly Gly Ser Lys Gln Asp Ala Ser Glu Ala Gly Thr Ala
            180                 185                 190

Gly Gly Asp Gly Gln Gly Ser Ser Ala Ala Ala His Asn Ser Gly Asp
        195                 200                 205

Gly Glu Glu Ala Lys
210

<210> SEQ ID NO 47
<211> LENGTH: 633
<212> TYPE: DNA
<213> ORGANISM: Glycine soya

<400> SEQUENCE: 47
atgcagcaga caccgcctat gattcctatg atgccttcgt tcccacctac gaacataacc     60
accgagcaga ttcaaaaata ccttgatgag aacaagaagc tgattctggc aatattggac    120
aatcaaaatc ttggaaaact tgcagaatgt gcccagtacc aagctcagct tcaaaagaat    180
ttgatgtatt tagctgcaat tgctgatgcc cagcctcaaa caccagccat gcctccacag    240
atggcaccac accctgccat gcaaccagga ttctatatgc aacatcctca ggctgcagca    300
gcagcaatgg ctcagcagca gcagcaagga atgttccccc agaaaatgcc attgcaattt    360
ggcaatccac atcaaatgca ggaacaacag cagcagctac accagcaagc catccaaggt    420
caaatgggac tgagacctgg aggaataaat aatggcatgc atccaatgca caatgagggc    480
ggcaacagcg gtggtccacc ctcggctacc ggtccgaacg acgcacgtgg tggaagcaag    540
caagatgctt ctgaggctgg aacagctggt ggagatggcc aaggcagctc tgcagctgct    600
cataacagtg gagatggtga agaggcaaag tga                                 633

<210> SEQ ID NO 48
<211> LENGTH: 210
<212> TYPE: PRT
<213> ORGANISM: Glycine soya

<400> SEQUENCE: 48

Met Gln Gln Thr Pro Pro Met Ile Pro Met Met Pro Ser Phe Pro Pro
1               5                   10                  15

Thr Asn Ile Thr Thr Glu Gln Ile Gln Lys Tyr Leu Asp Glu Asn Lys
            20                  25                  30

Lys Leu Ile Leu Ala Ile Leu Asp Asn Gln Asn Leu Gly Lys Leu Ala
        35                  40                  45

Glu Cys Ala Gln Tyr Gln Ala Gln Leu Gln Lys Asn Leu Met Tyr Leu
50                  55                  60

Ala Ala Ile Ala Asp Ala Gln Pro Gln Thr Pro Ala Met Pro Pro Gln
65                  70                  75                  80

Met Ala Pro His Pro Ala Met Gln Pro Gly Phe Tyr Met Gln His Pro
            85                  90                  95

Gln Ala Ala Ala Ala Met Ala Gln Gln Gln Gln Gly Met Phe
        100                 105                 110

Pro Gln Lys Met Pro Leu Gln Phe Gly Asn Pro His Gln Met Gln Glu
            115                 120                 125

Gln Gln Gln Gln Leu His Gln Ala Ile Gln Gly Gln Met Gly Leu
        130                 135                 140

Arg Pro Gly Gly Ile Asn Asn Gly Met His Pro Met His Asn Glu Gly
145                 150                 155                 160

Gly Asn Ser Gly Gly Pro Pro Ser Ala Thr Gly Pro Asn Asp Ala Arg
            165                 170                 175

Gly Gly Ser Lys Gln Asp Ala Ser Glu Ala Gly Thr Ala Gly Gly Asp
            180                 185                 190

Gly Gln Gly Ser Ser Ala Ala Ala His Asn Ser Gly Asp Gly Glu Glu
        195                 200                 205

Ala Lys
210

<210> SEQ ID NO 49
<211> LENGTH: 690
<212> TYPE: DNA
<213> ORGANISM: Gossypium hirsutum

<400> SEQUENCE: 49

```
atgcagcagc acctgatgca gatgcagccc atgatggcag cttattatcc caacaacgtc    60
actactgatc atattcaaca gtatctcgat gagaacaagt cattgatctt aaagattgtt   120
gagagccaga attctgggaa attgagtgaa tgtgctgaga accaagcaag ctgcagcga   180
aacctcatgt acctggctgc cattgcggat tctcaacccc aaccacccac cgtgcatgca   240
cagtttccat ctggtggtat catgcagcca ggagctgggc actacatgca gcaccaacaa   300
gctcaacaaa tgacacaaca gtcgcttatg gctgctcggt cctcaatgtt gtattctcag   360
caaccatttt ctgcactgca acaacaacag cagcaagctt tgcacagtca gcttggcatg   420
agctctggcg gaagcacagg ccttcatatg ctgcaaactg aatctagtac tgcaggtggc   480
agtggagcac ttgggccgg agggtttcct gatttggac gtggttcttc tggagaaggc   540
atccatggtg gcaggccaat ggcaggtgga agcaagcaag atatcgggag tgccggctca   600
gctgaaggtc gtggaggaag ctctggtggt cagggtggtg gtgatggggg tgaaaccctt   660
tacttaaaag cagccgatga tgggaactga                                    690
```

<210> SEQ ID NO 50
<211> LENGTH: 229
<212> TYPE: PRT
<213> ORGANISM: Gossypium hirsutum

<400> SEQUENCE: 50

Met Gln Gln His Leu Met Gln Met Gln Pro Met Met Ala Ala Tyr Tyr
1               5                   10                  15

Pro Asn Asn Val Thr Thr Asp His Ile Gln Gln Tyr Leu Asp Glu Asn
                20                  25                  30

Lys Ser Leu Ile Leu Lys Ile Val Glu Ser Gln Asn Ser Gly Lys Leu
            35                  40                  45

Ser Glu Cys Ala Glu Asn Gln Ala Arg Leu Gln Arg Asn Leu Met Tyr
        50                  55                  60

Leu Ala Ala Ile Ala Asp Ser Gln Pro Gln Pro Thr Val His Ala
65                  70                  75                  80

Gln Phe Pro Ser Gly Gly Ile Met Gln Pro Ala Gly His Tyr Met
                85                  90                  95

Gln His Gln Gln Ala Gln Gln Met Thr Gln Gln Ser Leu Met Ala Ala
                100                 105                 110

Arg Ser Ser Met Leu Tyr Ser Gln Gln Pro Phe Ser Ala Leu Gln Gln
            115                 120                 125

Gln Gln Gln Gln Ala Leu His Ser Gln Leu Gly Met Ser Ser Gly Gly
        130                 135                 140

Ser Thr Gly Leu His Met Leu Gln Thr Glu Ser Ser Thr Ala Gly Gly
145                 150                 155                 160

Ser Gly Ala Leu Gly Ala Gly Gly Phe Pro Asp Phe Gly Arg Gly Ser
                165                 170                 175

Ser Gly Glu Gly Ile His Gly Gly Arg Pro Met Ala Gly Gly Ser Lys
                180                 185                 190

Gln Asp Ile Gly Ser Ala Gly Ser Ala Glu Gly Arg Gly Gly Ser Ser
            195                 200                 205

Gly Gly Gln Gly Gly Gly Asp Gly Gly Glu Thr Leu Tyr Leu Lys Ala
        210                 215                 220

Ala Asp Asp Gly Asn
225

<210> SEQ ID NO 51
<211> LENGTH: 642
<212> TYPE: DNA
<213> ORGANISM: Gossypium hirsutum

<400> SEQUENCE: 51
atgccgcagc caccgcaaat gattcctgtg atgccttcat atccacctac taatatcact    60
actgaacaga ttcagaagta ccttgatgag aataagaagt tgattttggc aattttggac   120
aatcagaatc ttggaaaact cgctgaatgc gcccagtatc aagctcagct gcaaaagaat   180
ttgatgtatt tagctgcaat tgcggatgct caacctcaat caacgccagc aatgtcgcct   240
cagatggcac cgcatccagc aatgcaaccc ggaggatatt ttatgcaaca tcctcaagct   300
gctgcaatgt cacagcaacc tggcatgtac cctcaaaagg tgccattgca attcaatagt   360
ccgcatcaaa tgcaggaccc tcagcacctc ctatatcagc agcatcaaca agcaatgcaa   420
ggtcaaatgg gaatcaggcc tgggggaccc aataatagca tgcatcccat gcattcagag   480
gctagccttg gaggcggcag cagtggtggt ccccctcaac cttcaggccc aagtgatgga   540
cgtgctggaa acaagcaaga gggctccgaa gctggtggta atgggcaggg cagcacaact   600
ggtgggcatg gtggcggtga tggagcggat gaggcaaagt ga                     642

<210> SEQ ID NO 52
<211> LENGTH: 213
<212> TYPE: PRT
<213> ORGANISM: Gossypium hirsutum

<400> SEQUENCE: 52

```
Met Pro Gln Pro Gln Met Ile Pro Val Met Pro Ser Tyr Pro Pro
1               5                   10                  15

Thr Asn Ile Thr Thr Glu Gln Ile Gln Lys Tyr Leu Asp Glu Asn Lys
            20                  25                  30

Lys Leu Ile Leu Ala Ile Leu Asp Asn Gln Asn Leu Gly Lys Leu Ala
            35                  40                  45

Glu Cys Ala Gln Tyr Gln Ala Gln Leu Gln Lys Asn Leu Met Tyr Leu
50                  55                  60

Ala Ala Ile Ala Asp Ala Gln Pro Gln Ser Thr Pro Ala Met Ser Pro
65                  70                  75                  80

Gln Met Ala Pro His Pro Ala Met Gln Pro Gly Gly Tyr Phe Met Gln
                85                  90                  95

His Pro Gln Ala Ala Ala Met Ser Gln Pro Gly Met Tyr Pro Gln
            100                 105                 110

Lys Val Pro Leu Gln Phe Asn Ser Pro His Gln Met Gln Asp Pro Gln
            115                 120                 125

His Leu Leu Tyr Gln Gln His Gln Gln Ala Met Gln Gly Gln Met Gly
130                 135                 140

Ile Arg Pro Gly Gly Pro Asn Asn Ser Met His Pro Met His Ser Glu
145                 150                 155                 160

Ala Ser Leu Gly Gly Gly Ser Ser Gly Pro Gln Pro Ser Gly
                165                 170                 175

Pro Ser Asp Gly Arg Ala Gly Asn Lys Gln Glu Gly Ser Glu Ala Gly
            180                 185                 190

Gly Asn Gly Gln Gly Ser Thr Thr Gly Gly His Gly Gly Asp Gly
            195                 200                 205

Ala Asp Glu Ala Lys
    210
```

<210> SEQ ID NO 53
<211> LENGTH: 561
<212> TYPE: DNA
<213> ORGANISM: Hordeum vulgare

<400> SEQUENCE: 53

| | | |
|---|---|---|
| atgcagcaag cgatgcccat gccgccggcg cggcggcgc ctgggatgcc tccttctgcc | 60 |
| ggcctcagca ccgagcagat ccaaaagtac ctggatgaaa ataaacaact aattttggct | 120 |
| atcttggaaa atcagaacct gggaaagttg gcggaatgtg ctcagtatca agctcagctt | 180 |
| cagaagaatc ttttgtattt ggctgcgatt gctgatactc agccacagac ctctgtaagc | 240 |
| cgtcctcaga tggcaccacc tgctgcatcc ccaggggcag ggcattacat gtcacaggtg | 300 |
| ccaatgttcc ctccgaggac ccctctaacg cctcagcaga tgcaggagca gcaactacag | 360 |
| caacaacagg ctcagatgct tccgtttgct ggtcaaatgg ttgcgagacc cggggctgtc | 420 |
| aatggcattc cccaggcccc tcaagttgaa caaccagcct atgcagcagg tggggccagt | 480 |
| tccgagcctt ctggcaccga gagccacagg agcactggcg ccgataacga tggtgggagc | 540 |
| ggcttggctg accagtccta a | 561 |

<210> SEQ ID NO 54
<211> LENGTH: 186
<212> TYPE: PRT
<213> ORGANISM: Hordeum vulgare

<400> SEQUENCE: 54

Met Gln Gln Ala Met Pro Met Pro Pro Ala Ala Ala Pro Gly Met
1               5                  10                 15

Pro Pro Ser Ala Gly Leu Ser Thr Glu Gln Ile Gln Lys Tyr Leu Asp
           20                  25                  30

Glu Asn Lys Gln Leu Ile Leu Ala Ile Leu Glu Asn Gln Asn Leu Gly
       35                  40                  45

Lys Leu Ala Glu Cys Ala Gln Tyr Gln Ala Gln Leu Gln Lys Asn Leu
   50                  55                  60

Leu Tyr Leu Ala Ala Ile Ala Asp Thr Gln Pro Gln Thr Ser Val Ser
65                  70                  75                  80

Arg Pro Gln Met Ala Pro Pro Ala Ala Ser Pro Gly Ala Gly His Tyr
               85                  90                  95

Met Ser Gln Val Pro Met Phe Pro Pro Arg Thr Pro Leu Thr Pro Gln
           100                 105                 110

Gln Met Gln Glu Gln Gln Leu Gln Gln Gln Ala Gln Met Leu Pro
       115                 120                 125

Phe Ala Gly Gln Met Val Ala Arg Pro Gly Ala Val Asn Gly Ile Pro
130                 135                 140

Gln Ala Pro Gln Val Glu Gln Pro Ala Tyr Ala Ala Gly Gly Ala Ser
145                 150                 155                 160

Ser Glu Pro Ser Gly Thr Glu Ser His Arg Ser Thr Gly Ala Asp Asn
               165                 170                 175

Asp Gly Gly Ser Gly Leu Ala Asp Gln Ser
           180                 185

<210> SEQ ID NO 55
<211> LENGTH: 555
<212> TYPE: DNA
<213> ORGANISM: Lactuca serriola
<220> FEATURE:
<221> NAME/KEY: misc_feature
<222> LOCATION: (253)..(253)
<223> OTHER INFORMATION: n is a, c, g, or t

<400> SEQUENCE: 55

```
atgaagcagc cgatgatgcc gaatccaatg atgtcttctt cgtttcctcc tacaaacatc      60
accaccgatc agatccaaaa gttccttgat gaaaacaagc aactaattat agcaataatg     120
agcaacctaa atcttggaaa gcttgctgaa tgtgcccagt accaagctct actccaaaaa     180
aatttgatgt atctagcagc cattgcagat gctcaaccac ctacacctac accaacacta     240
aatatctctt atnagatggg cccggttcca catccaggga tgccacagca aggtggattt     300
tacatggcgc agcagcaccc tcaggcggct gtaatgacgg ctcagccacc ttctggtttt     360
ccacaaccga tgcctggtat gcaatttaac agcccacagg ctattcaagg cagatgggc      420 gggaggtccg gtgggccgcc aagctcagcc gctagtgatg tctggagagg aagcatgcaa     480
gatggtggtg gtggtgctgc tgctgatggt ggtaaggatg tcatgctgg  cggtggacct     540 gaggaagcaa agtaa                                                      555
```

<210> SEQ ID NO 56
<211> LENGTH: 184
<212> TYPE: PRT
<213> ORGANISM: Lactuca serriola
<220> FEATURE:
<221> NAME/KEY: misc_feature
<222> LOCATION: (85)..(85)
<223> OTHER INFORMATION: Xaa can be any naturally occurring amino acid

<400> SEQUENCE: 56

Met Lys Gln Pro Met Met Pro Asn Pro Met Met Ser Ser Ser Phe Pro
1               5                   10                  15

Pro Thr Asn Ile Thr Thr Asp Gln Ile Gln Lys Phe Leu Asp Glu Asn
                20                  25                  30

Lys Gln Leu Ile Ile Ala Ile Met Ser Asn Leu Asn Gly Lys Leu
            35                  40                  45

Ala Glu Cys Ala Gln Tyr Gln Ala Leu Leu Gln Lys Asn Leu Met Tyr
50                  55                  60

Leu Ala Ala Ile Ala Asp Ala Gln Pro Thr Pro Thr Pro Thr Leu
65                  70                  75                  80

Asn Ile Ser Tyr Xaa Met Gly Pro Val Pro His Pro Gly Met Pro Gln
                85                  90                  95

Gln Gly Gly Phe Tyr Met Ala Gln His Pro Gln Ala Ala Val Met
                100                 105                 110

Thr Ala Gln Pro Pro Ser Gly Phe Pro Gln Pro Met Pro Gly Met Gln
            115                 120                 125

Phe Asn Ser Pro Gln Ala Ile Gln Gly Gln Met Gly Gly Arg Ser Gly
        130                 135                 140

Gly Pro Pro Ser Ser Ala Ala Ser Asp Val Trp Arg Gly Ser Met Gln
145                 150                 155                 160

Asp Gly Gly Gly Ala Ala Ala Asp Gly Gly Lys Asp Gly His Ala
                165                 170                 175

Gly Gly Gly Pro Glu Glu Ala Lys
                180

<210> SEQ ID NO 57
<211> LENGTH: 627
<212> TYPE: DNA
<213> ORGANISM: Lycopersicon esculentum

<400> SEQUENCE: 57
atgcagcagc acctgatgca gatgcagccc atgatggcag cttactatcc aacgaacgtc      60
actactgacc atattcaaca gtatttggat gaaaacaaat cactcattct gaagattgtt     120
gagagccaga actctgggaa actcagtgaa tgtgcggaga accaagctag gcttcagagg     180
aatctgatgt accttgctgc gattgctgat tcacaacctc aaccttctag catgcattct     240
cagttctctt ctggtgggat gatgcagcca gggacacaca gttacttgca gcagcagcag     300
cagcaacaac aagcgcaaca aatggcaaca caacaactca tggctgcaag atcctcgtcg     360
atgctctatg gacaacagca gcagcaatct cagttatcgc aatatcaaca aggcttgcat     420
agtagccaac tcggcatgag ttctggcagt ggcggaagca ctggacttca tcacatgctt     480
caaagtgaat catcacctca tggtggtggt ttctctcatg acttcggccg cgcaaataag     540
caagacattg ggagtagtat gtctgctgaa gggcgcggcg aagttcagg tggtgagaat     600
ctttatctga aagcttctga ggattga                                         627

<210> SEQ ID NO 58
<211> LENGTH: 208
<212> TYPE: PRT
<213> ORGANISM: Lycopersicon esculentum

<400> SEQUENCE: 58

Met Gln Gln His Leu Met Gln Met Gln Pro Met Met Ala Ala Tyr Tyr
1               5                   10                  15

Pro Thr Asn Val Thr Thr Asp His Ile Gln Gln Tyr Leu Asp Glu Asn
                20                  25                  30

Lys Ser Leu Ile Leu Lys Ile Val Glu Ser Gln Asn Ser Gly Lys Leu
            35                  40                  45

Ser Glu Cys Ala Glu Asn Gln Ala Arg Leu Gln Arg Asn Leu Met Tyr
 50                  55                  60

Leu Ala Ala Ile Ala Asp Ser Gln Pro Gln Pro Ser Ser Met His Ser
 65                  70                  75                  80

Gln Phe Ser Ser Gly Gly Met Met Gln Pro Gly Thr His Ser Tyr Leu
                 85                  90                  95

Gln Gln Gln Gln Gln Gln Gln Ala Gln Met Ala Thr Gln Gln
             100                 105                 110

Leu Met Ala Ala Arg Ser Ser Met Leu Tyr Gly Gln Gln Gln
             115                 120                 125

Gln Ser Gln Leu Ser Gln Tyr Gln Gln Gly Leu His Ser Ser Gln Leu
            130                 135                 140

Gly Met Ser Ser Gly Ser Gly Gly Ser Thr Gly Leu His His Met Leu
145                 150                 155                 160

Gln Ser Glu Ser Ser Pro His Gly Gly Phe Ser His Asp Phe Gly
                165                 170                 175

Arg Ala Asn Lys Gln Asp Ile Gly Ser Ser Met Ser Ala Glu Gly Arg
            180                 185                 190

Gly Gly Ser Ser Gly Gly Glu Asn Leu Tyr Leu Lys Ala Ser Glu Asp
            195                 200                 205

<210> SEQ ID NO 59
<211> LENGTH: 624
<212> TYPE: DNA
<213> ORGANISM: Malus domestica

<400> SEQUENCE: 59
atgcagcagc caccacaaat gatccccgtc atgccttcat tcctcccac caacatcacc      60 accgaacaaa ttcagaagta ccttgatgac aacaaaaagt tgattctggc aatattggat    120
aatcaaaatc ttggaaaact tgctgagtgt gctcagtacc aggctctgct tcaaaagaat    180
ctgatgtatt tagcagcaat tgccgatgcg caaccacagg caccagctgc ccctccccag    240
atggccccac atcctgctat gcaacaggca ggatattaca tgcaacatcc tcaggcagca    300
gcaatggctc agcaacaggg tattttctcc ccaaagatgc cgatgcaatt caataacatg    360
catcaaatgc acgatccaca gcagcaccaa caagccatgc aagggcaaat gggaatgaga    420
cctggagggc taacggcat gccttccatg cttcatactg aggccacaca tggtggtggt      480
agtggcggcc caaattcagc tggagaccca atgatgggc gtggaggaag caagcaagac     540
gcctctgagt ctggggcagg tgtgatggc aggggacct cagccggcgg cgtggaact       600 ggtgatggag aggacggcaa gtga                                            624

<210> SEQ ID NO 60
<211> LENGTH: 207
<212> TYPE: PRT
<213> ORGANISM: Malus domestica

<400> SEQUENCE: 60

Met Gln Gln Pro Pro Gln Met Ile Pro Val Met Pro Ser Phe Pro Pro
 1               5                  10                  15

Thr Asn Ile Thr Thr Glu Gln Ile Gln Lys Tyr Leu Asp Asp Asn Lys
            20                  25                  30

Lys Leu Ile Leu Ala Ile Leu Asp Asn Gln Asn Leu Gly Lys Leu Ala
            35                  40                  45

Glu Cys Ala Gln Tyr Gln Ala Leu Leu Gln Lys Asn Leu Met Tyr Leu
        50                  55                  60

Ala Ala Ile Ala Asp Ala Gln Pro Gln Ala Pro Ala Ala Pro Pro Gln
65                  70                  75                  80

Met Ala Pro His Pro Ala Met Gln Gln Ala Gly Tyr Tyr Met Gln His
                85                  90                  95

Pro Gln Ala Ala Ala Met Ala Gln Gln Gly Ile Phe Ser Pro Lys
            100                 105                 110

Met Pro Met Gln Phe Asn Asn Met His Gln Met His Asp Pro Gln Gln
        115                 120                 125

His Gln Gln Ala Met Gln Gly Gln Met Gly Met Arg Pro Gly Gly Pro
    130                 135                 140

Asn Gly Met Pro Ser Met Leu His Thr Glu Ala Thr His Gly Gly Gly
145                 150                 155                 160

Ser Gly Gly Pro Asn Ser Ala Gly Asp Pro Asn Asp Gly Arg Gly Gly
                165                 170                 175

Ser Lys Gln Asp Ala Ser Glu Ser Gly Ala Gly Gly Asp Gly Gln Gly
            180                 185                 190

Thr Ser Ala Gly Gly Arg Gly Thr Gly Asp Gly Glu Asp Gly Lys
        195                 200                 205

<210> SEQ ID NO 61
<211> LENGTH: 639
<212> TYPE: DNA
<213> ORGANISM: Medicago trunculata

<400> SEQUENCE: 61
atgcagcaga cacctcaaat gattcctatg atgccttcat tcccacaaca aacaaacata      60
accactgagc agattcaaaa atatcttgat gagaacaaga agctgatcct ggcaatattg     120
gacaatcaaa atcttggaaa acttgcagaa tgtgcccagt accaagctca gcttcagaag     180
aatttgatgt atttagctgc aattgctgac gcgcagccac aaacaccggc cttgcctcca     240
cagatggccc cgcaccctgc gatgcaacaa ggattctata tgcaacatcc tcaggctgca     300
gcaatggctc agcaacaagg aatgttcccc caaaaaatgc caatgcagtt cggtaatccg     360
catcaaatgc aggatcagca gcatcagcag caacaacagc agctacatca gcaagctatg     420
caaggtcaaa tgggacttag acctggaggg ataaataacg gcatgcatcc aatgcacaac     480
gaggctgctc tcggaggtag cggcagtggt ggtcaaatga cgggcgtggt ggtgagcaa      540 gcaagatgct tcggagctgg gacagccggc ggtgatggtc aaggaacctc tgccgcagct     600
gcgcacaaca gtggagatgc ttcagaagaa ggaaagtaa                            639

<210> SEQ ID NO 62
<211> LENGTH: 213
<212> TYPE: PRT
<213> ORGANISM: Medicago trunculata

<400> SEQUENCE: 62

Met Gln Gln Thr Pro Gln Met Ile Pro Met Met Pro Ser Phe Pro Gln
1               5                   10                  15

Gln Thr Asn Ile Thr Thr Glu Gln Ile Gln Lys Tyr Leu Asp Glu Asn
            20                  25                  30

Lys Lys Leu Ile Leu Ala Ile Leu Asp Asn Gln Asn Leu Gly Lys Leu
        35                  40                  45

Ala Glu Cys Ala Gln Tyr Gln Ala Gln Leu Gln Lys Asn Leu Met Tyr
    50                  55                  60

Leu Ala Ala Ile Ala Asp Ala Gln Pro Gln Thr Pro Ala Leu Pro Pro
65                  70                  75                  80

Gln Met Ala Pro His Pro Ala Met Gln Gln Gly Phe Tyr Met Gln His
            85                  90                  95

Pro Gln Ala Ala Ala Met Ala Gln Gln Gly Met Phe Pro Gln Lys
        100                 105                 110

Met Pro Met Gln Phe Gly Asn Pro His Gln Met Gln Asp Gln Gln His
    115                 120                 125

Gln Gln Gln Gln Gln Leu His Gln Ala Met Gln Gly Gln Met
    130                 135                 140

Gly Leu Arg Pro Gly Gly Ile Asn Asn Gly Met His Pro Met His Asn
145                 150                 155                 160

Glu Ala Ala Leu Gly Gly Ser Gly Ser Gly Pro Asn Asp Gly Arg
                165                 170                 175

Gly Gly Gly Ser Lys Gln Asp Ala Ser Glu Ala Gly Thr Ala Gly
            180                 185                 190

Asp Gly Gln Gly Thr Ser Ala Ala Ala His Asn Ser Gly Asp Ala
        195                 200                 205

Ser Glu Glu Gly Lys
    210

<210> SEQ ID NO 63
<211> LENGTH: 624
<212> TYPE: DNA
<213> ORGANISM: Panicum virgatum

<400> SEQUENCE: 63
atgcagcagc agatgcccat gcagtcggcg ccccggcga ccggcatcac caccgagcag      60
atccaaaagt atttggatga aaataagcag cttatttggg ccatcctgga aaatcagaac     120
ttaggaaagt tggctgaatg tgctcagtat caagctcagc ttcaaaagaa tctcttgtac     180
ctggctgcga ttgcagatgc caacccccaa ccaccacaga accctgcaag tcgcccacag     240
atgatgcaac tggcatggt accaggtgca gggcattaca tgtcccaagt accaatgttc      300
ccgccaagaa caccattaac cccgcaacag atgcaagaac agcagcagca gcagcagcag     360
cttcaacagc agcaagcaca ggctcttgct ttcccgggac agatggtcat gagacctacc     420
attaatggca tgcagcctat gcaagccgac cctgctgccg ccgccgccag cctacagcag     480
tcagcacctg gccctactga tgggcgagga ggcaagcaag atgcaactgc tgggtgagc      540 acagagcctt ctggcaccga gccacaag agcacaaccg cagcagatca cgatgtgggc       600
actgatgtcg cggagaaatc ctaa                                             624

<210> SEQ ID NO 64
<211> LENGTH: 207
<212> TYPE: PRT
<213> ORGANISM: Panicum virgatum

<400> SEQUENCE: 64

Met Gln Gln Gln Met Pro Met Gln Ser Ala Pro Pro Ala Thr Gly Ile
1               5                   10                  15

Thr Thr Glu Gln Ile Gln Lys Tyr Leu Asp Glu Asn Lys Gln Leu Ile
            20                  25                  30

Leu Ala Ile Leu Glu Asn Gln Asn Leu Gly Lys Leu Ala Glu Cys Ala
        35                  40                  45

Gln Tyr Gln Ala Gln Leu Gln Lys Asn Leu Leu Tyr Leu Ala Ala Ile
    50                  55                  60

Ala Asp Ala Gln Pro Gln Pro Pro Gln Asn Pro Ala Ser Arg Pro Gln
 65                  70                  75                  80

Met Met Gln Pro Gly Met Val Pro Gly Ala Gly His Tyr Met Ser Gln
             85                  90                  95

Val Pro Met Phe Pro Pro Arg Thr Pro Leu Thr Pro Gln Gln Met Gln
            100                 105                 110

Glu Gln Gln Gln Gln Gln Gln Leu Gln Gln Gln Ala Gln Ala
            115                 120                 125

Leu Ala Phe Pro Gly Gln Met Val Met Arg Pro Thr Ile Asn Gly Met
130                 135                 140

Gln Pro Met Gln Ala Asp Pro Ala Ala Ala Ala Ser Leu Gln Gln
145                 150                 155                 160

Ser Ala Pro Gly Pro Thr Asp Gly Arg Gly Lys Gln Asp Ala Thr
                165                 170                 175

Ala Gly Val Ser Thr Glu Pro Ser Gly Thr Glu Ser His Lys Ser Thr
            180                 185                 190

Thr Ala Ala Asp His Asp Val Gly Thr Asp Val Ala Glu Lys Ser
            195                 200                 205

<210> SEQ ID NO 65
<211> LENGTH: 747
<212> TYPE: DNA
<213> ORGANISM: Picea sitchensis

<400> SEQUENCE: 65
atgcagcagc atctcatgca aatgcagccc atgatggcgg catacgcctc caacaacatc         60
accactgatc acatccagaa gtacctggat gagaacaagc agttgattct ggcaattctg        120
gacaaccaaa atcttggaaa gctcaatgag tgtgctcagt accaagcaaa acttcagcag        180
aatttgatgt atctggctgc gattgctgat tctcaaccac aagcacaaac tgcacatgct        240
cagattcctc ctaatgcagt gatgcagtct ggtgggcatt acatgcagca ccagcaggca        300
cagcaacaag tgactcctca gtctctgatg gcagctagat cttccatgct gtattctcag        360
cagccgatgg ctgctttgca tcaagctcag caacaacagc agcagcagca tcagcagcaa        420
caacaatctc ttcacagcca gcttggcata aattctggag gaagcagtgg attgcatatg        480
ttgcatggtg agacaaacat gggatgtaat gggcctctct catctggggg cttccctgaa        540
tttgggcgtg ggtctgctac ctctgctgaa ggtatgcagg ccaacagggg cttcactata        600
gatcgtggtt caaataagca ggatggagta ggatcagaga atgcccatcc aggtgctggt        660
gatggaagag ggagttcaac tggagggcag aatgcagatg agtcagaacc atcataccctg       720 aaagcctccg aagaagaagg aaactag                                             747

<210> SEQ ID NO 66
<211> LENGTH: 248
<212> TYPE: PRT
<213> ORGANISM: Picea sitchensis

<400> SEQUENCE: 66

Met Gln Gln His Leu Met Gln Met Gln Pro Met Met Ala Ala Tyr Ala
1               5                   10                  15

Ser Asn Asn Ile Thr Thr Asp His Ile Gln Lys Tyr Leu Asp Glu Asn
            20                  25                  30

Lys Gln Leu Ile Leu Ala Ile Leu Asp Asn Gln Asn Leu Gly Lys Leu
        35                  40                  45

Asn Glu Cys Ala Gln Tyr Gln Ala Lys Leu Gln Gln Asn Leu Met Tyr

Leu Ala Ala Ile Ala Asp Ser Gln Pro Gln Ala Gln Thr Ala His Ala
65                  70                  75                  80

Gln Ile Pro Pro Asn Ala Val Met Gln Ser Gly Gly His Tyr Met Gln
                85                  90                  95

His Gln Ala Gln Gln Val Thr Pro Gln Ser Leu Met Ala Ala
            100                 105                 110

Arg Ser Ser Met Leu Tyr Ser Gln Pro Met Ala Ala Leu His Gln
            115                 120                 125

Ala Gln Gln Gln Gln Gln Gln His Gln Gln Gln Gln Ser Leu
130                 135                 140

His Ser Gln Leu Gly Ile Asn Ser Gly Gly Ser Ser Gly Leu His Met
145                 150                 155                 160

Leu His Gly Glu Thr Asn Met Gly Cys Asn Gly Pro Leu Ser Ser Gly
                165                 170                 175

Gly Phe Pro Glu Phe Gly Arg Gly Ser Ala Thr Ser Ala Glu Gly Met
            180                 185                 190

Gln Ala Asn Arg Gly Phe Thr Ile Asp Arg Gly Ser Asn Lys Gln Asp
            195                 200                 205

Gly Val Gly Ser Glu Asn Ala His Pro Gly Ala Gly Asp Gly Arg Gly
210                 215                 220

Ser Ser Thr Gly Gly Gln Asn Ala Asp Glu Ser Glu Pro Ser Tyr Leu
225                 230                 235                 240

Lys Ala Ser Glu Glu Glu Gly Asn
                245

<210> SEQ ID NO 67
<211> LENGTH: 735
<212> TYPE: DNA
<213> ORGANISM: Pinus taeda

<400> SEQUENCE: 67
atgcagcagc acctcatgca aatgcagccc atgatggcgg cctacgcctc caacaatatc       60
accactgatc acatccagaa gtacctggat gagaacaagc agttgattct ggcaattttg      120
gacaaccaaa atctcggaaa gctcaatgag tgtgctcaat accaagcaaa acttcagcag      180
aatttgatgt atctggctgc tattgctgat tctcaacctc aagcacaaac tgcacatgct      240
cagattcctc caaatgcggt gatgcagtct ggtgggcatt acatgcagca tcaacaggca      300
cagcaacaag ttactcctca gtctctgatg cagctagat cttccatact gtatgctcag      360
caacaacagc agcagcagca tcagcagcat cagcagcaac agcagcaaca acagtctctt      420
cacagccagc ttggcataaa ttctggagga agcagcggtt gcatatgtt gcatggtgag       480
acaaacatgg gatgtaatgg gcctctgtca tctggggat ccctgaatt tgggcgtggg        540
tctgctacct ctgctgatgg tatgcaggtg aacaggggc ttgctataga tcgtggttca      600
aacaagcagg atggagttgg atcagagaat gcccatgctg gtgctggtga tggaagaggg     660
agttcaactg agggcagaa tgcagatgag tcagaaccat catacctgaa ggcctccgag      720
gaagaaggaa actag                                                      735

<210> SEQ ID NO 68
<211> LENGTH: 244
<212> TYPE: PRT
<213> ORGANISM: Pinus taeda

<400> SEQUENCE: 68

```
Met Gln Gln His Leu Met Gln Met Gln Pro Met Met Ala Ala Tyr Ala
1               5                   10                  15

Ser Asn Asn Ile Thr Thr Asp His Ile Gln Lys Tyr Leu Asp Glu Asn
                20                  25                  30

Lys Gln Leu Ile Leu Ala Ile Leu Asp Asn Gln Asn Leu Gly Lys Leu
            35                  40                  45

Asn Glu Cys Ala Gln Tyr Gln Ala Lys Leu Gln Gln Asn Leu Met Tyr
        50                  55                  60

Leu Ala Ala Ile Ala Asp Ser Gln Pro Gln Ala Gln Thr Ala His Ala
65                  70                  75                  80

Gln Ile Pro Pro Asn Ala Val Met Gln Ser Gly His Tyr Met Gln
                85                  90                  95

His Gln Gln Ala Gln Gln Val Thr Pro Gln Ser Leu Met Ala Ala
            100                 105                 110

Arg Ser Ser Ile Leu Tyr Ala Gln Gln Gln Gln Gln Gln His Gln
            115                 120                 125

Gln His Gln Gln Gln Gln Gln Gln Ser Leu His Ser Gln Leu
        130                 135             140

Gly Ile Asn Ser Gly Gly Ser Ser Gly Leu His Met Leu His Gly Glu
145                 150                 155                 160

Thr Asn Met Gly Cys Asn Gly Pro Leu Ser Ser Gly Phe Pro Glu
                165                 170                 175

Phe Gly Arg Gly Ser Ala Thr Ser Ala Asp Gly Met Gln Val Asn Arg
            180                 185                 190

Gly Phe Ala Ile Asp Arg Gly Ser Asn Lys Gln Asp Gly Val Gly Ser
            195                 200                 205

Glu Asn Ala His Ala Gly Ala Gly Asp Gly Arg Gly Ser Ser Thr Gly
210                 215                 220

Gly Gln Asn Ala Asp Glu Ser Glu Pro Ser Tyr Leu Lys Ala Ser Glu
225                 230                 235                 240

Glu Glu Gly Asn

<210> SEQ ID NO 69
<211> LENGTH: 663
<212> TYPE: DNA
<213> ORGANISM: Populus tremula

<400> SEQUENCE: 69
atgcaacagc acctgatgca gatgcagccc atgatggcag cctattaccc cagcaacgtc      60
actactgatc atattcaaca gtatctggac gaaaacaagt cattgatttt gaagattgtt     120
gagagccaga attcagggaa actcagtgag tgtgcagaga accaagcaag actgcaacaa     180
aatctcatgt acttggctgc aattgctgat tgtcagcccc aaccacctac catgcatgcc     240
cagttcccct tccagcggca tatgcagcca ggagcacatt acatgcagca tcaacaagct     300
caacagatga caccacaagc ccttatggct gcacgctctt ctatgctgca gtatgctcaa     360
cagccattct cagcgcttca acaacagcaa gccttacaca gccagctcgg catgagctct     420
ggtggaagcg caggacttca tatgatgcaa agcgaggcta acactgcagg aggcagtgga     480
gctcttggtg ctggacgatt tcctgatttt ggcatggatg cctccagtag aggaatcgca     540
agtgggagca agcaagatat tcggagtgca gggtctagtg aagggcgagg aggaagctct     600
ggaggccagg gtggtgatgg aggtgaaacc ctttacttga atctgctga tgatgggaac     660 tga                                                                   663
```

<210> SEQ ID NO 70
<211> LENGTH: 220
<212> TYPE: PRT
<213> ORGANISM: Populus tremula

<400> SEQUENCE: 70

Met Gln Gln His Leu Met Gln Met Gln Pro Met Met Ala Ala Tyr Tyr
1               5                   10                  15

Pro Ser Asn Val Thr Thr Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Gln Asn Leu Met Tyr
    50                  55                  60

Leu Ala Ala Ile Ala Asp Cys Gln Pro Gln Pro Thr Met His Ala
65                  70                  75                  80

Gln Phe Pro Ser Ser Gly Ile Met Gln Pro Gly Ala His Tyr Met Gln
                85                  90                  95

His Gln Gln Ala Gln Gln Met Thr Pro Gln Ala Leu Met Ala Ala Arg
            100                 105                 110

Ser Ser Met Leu Gln Tyr Ala Gln Gln Pro Phe Ser Ala Leu Gln Gln
        115                 120                 125

Gln Gln Ala Leu His Ser Gln Leu Gly Met Ser Ser Gly Gly Ser Ala
    130                 135                 140

Gly Leu His Met Met Gln Ser Glu Ala Asn Thr Ala Gly Gly Ser Gly
145                 150                 155                 160

Ala Leu Gly Ala Gly Arg Phe Pro Asp Phe Gly Met Asp Ala Ser Ser
                165                 170                 175

Arg Gly Ile Ala Ser Gly Ser Lys Gln Asp Ile Arg Ser Ala Gly Ser
            180                 185                 190

Ser Glu Gly Arg Gly Gly Ser Ser Gly Gly Gln Gly Gly Asp Gly Gly
        195                 200                 205

Glu Thr Leu Tyr Leu Lys Ser Ala Asp Asp Gly Asn
    210                 215                 220

<210> SEQ ID NO 71
<211> LENGTH: 678
<212> TYPE: DNA
<213> ORGANISM: Saccharum officinarum

<400> SEQUENCE: 71
atgcagcagc aacacctgat gcagatgaac cagaacatga ttgggggcta cacctctcct      60
gccgctgtga caaccgatct catccagcag tacctggatg agaacaagca gctgatcctg     120
gccatcctcg acaaccagaa caatggcaag gtggaggagt gcgaacggca ccaagctaag     180
ctccagcaca acctcatgta cctggccgcc atcgccgaca gccagccacc acagactgca     240
ccactatcac aatacccgtc caacctgatg atgcagccgg ccctcggta catgccaccg      300 cagtccgggc agatgatgag cccgcagtcg ctaatggcgg cgcggtcctc catgatgtac     360
gcgcacccgt ccatgtcacc actccagcag cagcaggcag cgcacgggca gctgggcatg     420
gcttcagggg gcggcggtgg cacgaccagt gggttcaaca tcctccatgg cgaggccagt     480
atgggcggtg ctggtggcgc ttgtgccggc aacaacatga tgaacgccgg catgttctca     540
ggctttggcc gcagcggcag tggcgccaag gagggatcga cctcgctgtc ggttgacgtc     600
cgtggtggca ccagctccgg cgcgcaaagc ggggacggcg agtacctgaa agcaggcacc     660
gaggaagaag gcagttaa                                                    678

<210> SEQ ID NO 72
<211> LENGTH: 225
<212> TYPE: PRT
<213> ORGANISM: Saccharum officinarum

<400> SEQUENCE: 72

```
Met Gln Gln Gln His Leu Met Gln Met Asn Gln Asn Met Ile Gly Gly
1               5                   10                  15

Tyr Thr Ser Pro Ala Ala Val Thr Thr Asp Leu Ile Gln Gln Tyr Leu
            20                  25                  30

Asp Glu Asn Lys Gln Leu Ile Leu Ala Ile Leu Asp Asn Gln Asn Asn
        35                  40                  45

Gly Lys Val Glu Glu Cys Glu Arg His Gln Ala Lys Leu Gln His Asn
    50                  55                  60

Leu Met Tyr Leu Ala Ala Ile Ala Asp Ser Gln Pro Pro Gln Thr Ala
65                  70                  75                  80

Pro Leu Ser Gln Tyr Pro Ser Asn Leu Met Gln Pro Gly Pro Arg
                85                  90                  95

Tyr Met Pro Pro Gln Ser Gly Met Met Ser Pro Gln Ser Leu Met
            100                 105                 110

Ala Ala Arg Ser Ser Met Met Tyr Ala His Pro Ser Met Ser Pro Leu
            115                 120                 125

Gln Gln Gln Gln Ala Ala His Gly Gln Leu Gly Met Ala Ser Gly Gly
    130                 135                 140

Gly Gly Gly Thr Thr Ser Gly Phe Asn Ile Leu His Gly Glu Ala Ser
145                 150                 155                 160

Met Gly Gly Ala Gly Gly Ala Cys Ala Gly Asn Asn Met Met Asn Ala
                165                 170                 175

Gly Met Phe Ser Gly Phe Gly Arg Ser Gly Ser Gly Ala Lys Glu Gly
            180                 185                 190

Ser Thr Ser Leu Ser Val Asp Val Arg Gly Gly Thr Ser Ser Gly Ala
        195                 200                 205

Gln Ser Gly Asp Gly Glu Tyr Leu Lys Ala Gly Thr Glu Glu Glu Gly
    210                 215                 220

Ser
225
```

<210> SEQ ID NO 73
<211> LENGTH: 561
<212> TYPE: DNA
<213> ORGANISM: Saccharum officinarum

<400> SEQUENCE: 73

```
atgcagcagc cgatgcccat gcagccgcag gcgccggaga tgaccccggc cgccggaatc      60
accacggagc agatccaaaa gtatctggat gagaataagc agcttatttt ggctattttg     120
gaaaatcaga acctaggaaa attggcagaa tgtgctcagt atcaatcaca acttcagaag     180
aacctcttgt atctcgctgc aatcgcagat gcccaaccac agactgctgt aagccgccct     240
cagatggcgc cgcctggtgc attgcctgga gtagggcagt acatgtcaca ggtgcctatg     300
ttcccaccga ggacacctct aacacccag cagatgcagg agcagcaact tcagcagcag     360
caggctcagc tgctaaattt cagtggccta atggttgcta gacctggcat ggtcaacggc     420
atgcctcagt ccattcaagt tcagcaagct cagccaccac cagcagggaa caaacaggat     480
gctggtgggg tcgcctcgga gccctcgggc attgagaacc acaggagcac tggtggtgat     540
```

```
aatgatggtg gaagcgacta g                                              561
```

<210> SEQ ID NO 74
<211> LENGTH: 186
<212> TYPE: PRT
<213> ORGANISM: Saccharum officinarum

<400> SEQUENCE: 74

```
Met Gln Gln Pro Met Pro Met Gln Pro Gln Ala Pro Glu Met Thr Pro
1               5                   10                  15

Ala Ala Gly Ile Thr Thr Glu Gln Ile Gln Lys Tyr Leu Asp Glu Asn
            20                  25                  30

Lys Gln Leu Ile Leu Ala Ile Leu Glu Asn Gln Asn Leu Gly Lys Leu
        35                  40                  45

Ala Glu Cys Ala Gln Tyr Gln Ser Gln Leu Gln Lys Asn Leu Leu Tyr
    50                  55                  60

Leu Ala Ala Ile Ala Asp Ala Gln Pro Gln Thr Ala Val Ser Arg Pro
65                  70                  75                  80

Gln Met Ala Pro Pro Gly Ala Leu Pro Gly Val Gly Gln Tyr Met Ser
                85                  90                  95

Gln Val Pro Met Phe Pro Pro Arg Thr Pro Leu Thr Pro Gln Gln Met
            100                 105                 110

Gln Glu Gln Gln Leu Gln Gln Gln Ala Gln Leu Leu Asn Phe Ser
        115                 120                 125

Gly Leu Met Val Ala Arg Pro Gly Met Val Asn Gly Met Pro Gln Ser
    130                 135                 140

Ile Gln Val Gln Gln Ala Gln Pro Pro Pro Ala Gly Asn Lys Gln Asp
145                 150                 155                 160

Ala Gly Gly Val Ala Ser Glu Pro Ser Gly Ile Glu Asn His Arg Ser
                165                 170                 175

Thr Gly Gly Asp Asn Asp Gly Gly Ser Asp
            180                 185
```

<210> SEQ ID NO 75
<211> LENGTH: 642
<212> TYPE: DNA
<213> ORGANISM: Saccharum officinarum

<400> SEQUENCE: 75

```
atgcagcagc agatgcccat gccgccggcg cccgctgcgg cggcggcgcc cccggcggcc    60
ggcatcacca ccgagcagat ccaaaagtat ttggacgaaa ataagcaact tattttggcc   120
atcctggaaa atcagaactt aggaaagttg gctgaatgtg ctcagtatca agctcaactt   180
caaaagaacc tcttgtacct ggctgcgatt gctgatgccc aacccagcc accacaaaac   240 cctgcaggtc gccctcagat gatgcaacct ggtatagtgc aggtgcggg gcattacatg   300 tcacaagtac caatgttccc tccaagaact ccattaaccc cacagcagat gcaagagcag   360
cagcagcaac agcttcagca gcagcaagcg caggctctta cattccctgg acagatggtc   420
atgagaccag ctaccatcaa cggcatacag cagcctatgc aagctgaccc tgcccgggca   480
gcggagctgc aacaaccacc acctatccca gctgacgggc gagtaagcaa gcagcaggac   540
acaacggctg gcgtgagctc agagcctttct gccaatgaga gccacaagac cacaactgga   600
gcagatagtg aggcaggtgg tgacgtggcg agaaatcct aa                       642
```

<210> SEQ ID NO 76
<211> LENGTH: 213
<212> TYPE: PRT

<213> ORGANISM: Saccharum officinarum

<400> SEQUENCE: 76

```
Met Gln Gln Gln Met Pro Met Pro Pro Ala Pro Ala Ala Ala Ala
1               5                   10                  15

Pro Pro Ala Ala Gly Ile Thr Thr Glu Gln Ile Gln Lys Tyr Leu Asp
            20                  25                  30

Glu Asn Lys Gln Leu Ile Leu Ala Ile Leu Glu Asn Gln Asn Leu Gly
        35                  40                  45

Lys Leu Ala Glu Cys Ala Gln Tyr Gln Ala Gln Leu Gln Lys Asn Leu
    50                  55                  60

Leu Tyr Leu Ala Ala Ile Ala Asp Ala Gln Pro Gln Pro Pro Gln Asn
65                  70                  75                  80

Pro Ala Gly Arg Pro Gln Met Met Gln Pro Gly Ile Val Pro Gly Ala
                85                  90                  95

Gly His Tyr Met Ser Gln Val Pro Met Phe Pro Pro Arg Thr Pro Leu
            100                 105                 110

Thr Pro Gln Gln Met Gln Glu Gln Gln Gln Gln Leu Gln Gln Gln
        115                 120                 125

Gln Ala Gln Ala Leu Thr Phe Pro Gly Gln Met Val Met Arg Pro Ala
    130                 135                 140

Thr Ile Asn Gly Ile Gln Gln Pro Met Gln Ala Asp Pro Ala Arg Ala
145                 150                 155                 160

Ala Glu Leu Gln Gln Pro Pro Ile Pro Ala Asp Gly Arg Val Ser
                165                 170                 175

Lys Gln Gln Asp Thr Thr Ala Gly Val Ser Ser Glu Pro Ser Ala Asn
            180                 185                 190

Glu Ser His Lys Thr Thr Thr Gly Ala Asp Ser Glu Ala Gly Gly Asp
        195                 200                 205

Val Ala Glu Lys Ser
    210
```

<210> SEQ ID NO 77
<211> LENGTH: 645
<212> TYPE: DNA
<213> ORGANISM: Solanum tuberosum

<400> SEQUENCE: 77

```
atgcagcagc acctgatgca gatgcagccc atgatggcag cttactatcc aacgaacgtc    60
actactgacc atattcaaca gtatttggat gagaacaaat cactcattct gaaaattgtt   120
gagagccaaa actcgggaaa actcagtgaa tgtgcagaga accaagctag gcttcagagg   180
aatctgatgt accttgctgc tattgctgat tcacaacctc agccttctag catgcattct   240
cagttctctt ctggtgggat gatgcagcca gggacacaca gttacctgca gcagcagcag   300
cagcaacaac aagcgcaaca aatggcaaca caacaactca tggctgcaag atcctcatca   360
atgctctatg acaacaaca gcagcagcag cagcagtctc agttatcaca atttcaacaa   420
ggcttgcata gtagccaact tggcatgagt tctggcagtg gtggaagcac tggacttcat   480
cacatgcttc aaagtgaatc atcacctcat ggtggtggtt tctctcatga cttcggccgt   540
gcaaataagc aagacattgg gagtagtatg tctgctgaag gcgcggcgg aagctcaggt   600
ggtgatggtg gtgagaatct ttatctgaaa gcttctgagg attga              645
```

<210> SEQ ID NO 78
<211> LENGTH: 214
<212> TYPE: PRT

<213> ORGANISM: Solanum tuberosum

<400> SEQUENCE: 78

```
Met Gln Gln His Leu Met Gln Met Gln Pro Met Met Ala Ala Tyr Tyr
1               5                   10                  15
Pro Thr Asn Val Thr Thr Asp His Ile Gln Gln Tyr Leu Asp Glu Asn
            20                  25                  30
Lys Ser Leu Ile Leu Lys Ile Val Glu Ser Gln Asn Ser Gly Lys Leu
        35                  40                  45
Ser Glu Cys Ala Glu Asn Gln Ala Arg Leu Gln Arg Asn Leu Met Tyr
50                  55                  60
Leu Ala Ala Ile Ala Asp Ser Gln Pro Gln Pro Ser Ser Met His Ser
65                  70                  75                  80
Gln Phe Ser Ser Gly Gly Met Met Gln Pro Gly Thr His Ser Tyr Leu
                85                  90                  95
Gln Gln Gln Gln Gln Gln Gln Ala Gln Gly Met Ala Thr Gln Gln
            100                 105                 110
Leu Met Ala Ala Arg Ser Ser Met Leu Tyr Gly Gln Gln Gln Gln
        115                 120                 125
Gln Gln Gln Gln Ser Gln Leu Ser Gln Phe Gln Gln Gly Leu His Ser
130                 135                 140
Ser Gln Leu Gly Met Ser Ser Gly Ser Gly Ser Thr Gly Leu His
145                 150                 155                 160
His Met Leu Gln Ser Glu Ser Ser Pro His Gly Gly Phe Ser His
                165                 170                 175
Asp Phe Gly Arg Ala Asn Lys Gln Asp Ile Gly Ser Ser Met Ser Ala
            180                 185                 190
Glu Gly Arg Gly Gly Ser Ser Gly Gly Asp Gly Glu Asn Leu Tyr
        195                 200                 205
Leu Lys Ala Ser Glu Asp
    210
```

<210> SEQ ID NO 79
<211> LENGTH: 645
<212> TYPE: DNA
<213> ORGANISM: Sorghum bicolor

<400> SEQUENCE: 79

```
atgcagcagc agatgcccat gccgccggcg cccgctgcgg cggcggcgac ggcgcccccg      60
gcggccggca tcaccaccga gcagatccag aagtatttgg acgaaaataa gcaacttatt     120
ttggccatcc tagaaaatca gaacttagga aagttggctg aatgtgctca gtatcaagct     180
caacttcaaa agaacctctt gtacctggct gcgattgctg atgcccaacc ccgaccaccg     240
caaaaccctg caggtcgccc tcagatgatg caacctggta tagtgccagg tgcagggcat     300
tacatgtcac aagtaccaat gttccctcca agaactccat taccccacaa gcaaatgcaa     360
gagcagcagc agcaacagct tcagcagcag caagcgcagg ctcttgcatt ccctgggcag     420
atggtcatga ccagctacat caacggc atgcagcagc ctatgcaggc tgaccctgcc     480
cgggcagcgg agctgcaaca gccagcatct gtcccagccg acgggcgagt aagcaagcag     540
gacacagcgg ctgggggtgag ctcagagcct tctgccaatg agagccacaa gaccacaacc     600
ggagcagata gtgaggcagg tggagacgtg gcggagaaat cctaa                    645
```

<210> SEQ ID NO 80
<211> LENGTH: 214
<212> TYPE: PRT

<213> ORGANISM: Sorghum bicolor

<400> SEQUENCE: 80

| Met<br>1 | Gln | Gln | Gln | Met<br>5 | Pro | Met | Pro | Pro | Ala<br>10 | Ala | Ala | Ala | Ala | Ala<br>15 |

| Thr | Ala | Pro | Pro<br>20 | Ala | Ala | Gly | Ile | Thr<br>25 | Thr | Glu | Gln | Ile | Gln<br>30 | Lys | Tyr |

| Leu | Asp | Glu<br>35 | Asn | Lys | Gln | Leu | Ile<br>40 | Leu | Ala | Ile | Leu | Glu<br>45 | Asn | Gln | Asn |

| Leu | Gly<br>50 | Lys | Leu | Ala | Glu | Cys<br>55 | Ala | Gln | Tyr | Gln | Ala<br>60 | Gln | Leu | Gln | Lys |

| Asn<br>65 | Leu | Leu | Tyr | Leu | Ala<br>70 | Ala | Ile | Ala | Asp | Ala<br>75 | Gln | Pro | Arg | Pro | Pro<br>80 |

| Gln | Asn | Pro | Ala | Gly<br>85 | Arg | Pro | Gln | Met | Met<br>90 | Gln | Pro | Gly | Ile | Val<br>95 | Pro |

| Gly | Ala | Gly | His<br>100 | Tyr | Met | Ser | Gln | Val<br>105 | Pro | Met | Phe | Pro | Pro<br>110 | Arg | Thr |

| Pro | Leu | Thr<br>115 | Pro | Gln | Gln | Met | Gln<br>120 | Glu | Gln | Gln | Gln | Gln<br>125 | Gln | Leu | Gln |

| Gln | Gln<br>130 | Gln | Ala | Gln | Ala | Leu<br>135 | Ala | Phe | Pro | Gly | Gln<br>140 | Met | Val | Met | Arg |

| Pro<br>145 | Ala | Thr | Ile | Asn | Gly<br>150 | Met | Gln | Gln | Pro | Met<br>155 | Gln | Ala | Asp | Pro | Ala<br>160 |

| Arg | Ala | Ala | Glu | Leu<br>165 | Gln | Gln | Pro | Ala | Ser<br>170 | Val | Pro | Ala | Asp | Gly<br>175 | Arg |

| Val | Ser | Lys | Gln<br>180 | Asp | Thr | Ala | Ala | Gly<br>185 | Val | Ser | Ser | Glu | Pro<br>190 | Ser | Ala |

| Asn | Glu | Ser<br>195 | His | Lys | Thr | Thr | Thr<br>200 | Gly | Ala | Asp | Ser | Glu<br>205 | Ala | Gly | Gly |

| Asp | Val | Ala | Glu | Lys | Ser |
| | | 210 | | | |

<210> SEQ ID NO 81
<211> LENGTH: 558
<212> TYPE: DNA
<213> ORGANISM: Triticum aestivum

<400> SEQUENCE: 81

```
atgcagcaag cgatgcccat gccgccggcg gcggcggcgc cggggatgcc tccgtctgct      60
ggcctcagca ccgagcagat ccaaaagtac ctggatgaaa ataagcaact aattttggct     120
atcttggaaa atcagaacct gggaaagttg gcggaatgtg ctcagtatca agctcagctt     180
cagaagaatc ttttgtattt ggctgcaatc gctgatactc agccacagac cactgtaagc     240
cgtcctcaga tggcaccacc tagtgcatcc caggggcag gcattacat gtcacaggtg      300
ccaatgttcc ctccgaggac ccctctaacg cctcagcaga tgcaggagca gcaactacag     360
cagcaacagg ctcagatgct tccgtttgct ggtcaaatgg ttgcgagacc tggggctgtc     420
aatggcatgc ctcaggcccc tcaagttgaa ccagcctatg cagcaggtgg ggccagttct     480
gagccttctg gcactgagag ccacaggagc actggtgccg ataatgacgg ggggagcggc     540
tgggctgatc agtcctaa                                                   558
```

<210> SEQ ID NO 82
<211> LENGTH: 185
<212> TYPE: PRT
<213> ORGANISM: Triticum aestivum

```
<400> SEQUENCE: 82

Met Gln Gln Ala Met Pro Met Pro Pro Ala Ala Ala Pro Gly Met
1               5                   10                  15

Pro Pro Ser Ala Gly Leu Ser Thr Glu Gln Ile Gln Lys Tyr Leu Asp
            20                  25                  30

Glu Asn Lys Gln Leu Ile Leu Ala Ile Leu Glu Asn Gln Asn Leu Gly
        35                  40                  45

Lys Leu Ala Glu Cys Ala Gln Tyr Gln Ala Gln Leu Gln Lys Asn Leu
50                  55                  60

Leu Tyr Leu Ala Ala Ile Ala Asp Thr Gln Pro Gln Thr Thr Val Ser
65                  70                  75                  80

Arg Pro Gln Met Ala Pro Pro Ser Ala Ser Pro Gly Ala Gly His Tyr
                85                  90                  95

Met Ser Gln Val Pro Met Phe Pro Pro Arg Thr Pro Leu Thr Pro Gln
            100                 105                 110

Gln Met Gln Glu Gln Gln Leu Gln Gln Gln Ala Gln Met Leu Pro
        115                 120                 125

Phe Ala Gly Gln Met Val Ala Arg Pro Gly Ala Val Asn Gly Met Pro
130                 135                 140

Gln Ala Pro Gln Val Glu Pro Ala Tyr Ala Gly Gly Ala Ser Ser
145                 150                 155                 160

Glu Pro Ser Gly Thr Glu Ser His Arg Ser Thr Gly Ala Asp Asn Asp
                165                 170                 175

Gly Gly Ser Gly Trp Ala Asp Gln Ser
            180                 185

<210> SEQ ID NO 83
<211> LENGTH: 603
<212> TYPE: DNA
<213> ORGANISM: Triticum aestivum

<400> SEQUENCE: 83
atgcagcagg cgatgtcctt gcccccggga gcggtcggcg cggtgtcctc gccggccggc    60
atcaccaccg agcagatcca aaagtatttg gatgaaaata agcaacttat tttggccatc   120
cttgaaaatc agaacctagg aaagttggct gaatgtgctc agtatcaagc tcaactccaa   180
aagaatctct tgtatctagc tgctatcgcg gatgcccaac caccacagaa ccctacaagt   240
caccctcaga tggtgcagcc tggtagtatg caaggtgcag gcattacat gtcacaagta   300
ccaatgttcc ctccaagaac gccttaacc ccacagcaga tgcaagagca gcagcaccag   360
cagcttcagc agcagcaagc ccaggccctt tctttccccg cccaggtggt catgagacca   420
ggcaccgtca acggcatgca gcagcctatg caagcagccg cgacctcca gccagcagca   480
gcacctggag ggagcaagca ggacgccgca gtggctgggg ccagctcgga accatctggc   540
accaagagcc acaagaacgc gggagcagag gaggtgggcg ctgatgtagc agaacaatcc   600
taa                                                                  603

<210> SEQ ID NO 84
<211> LENGTH: 200
<212> TYPE: PRT
<213> ORGANISM: Triticum aestivum

<400> SEQUENCE: 84

Met Gln Gln Ala Met Ser Leu Pro Pro Gly Ala Val Gly Ala Val Ser
1               5                   10                  15

Ser Pro Ala Gly Ile Thr Thr Glu Gln Ile Gln Lys Tyr Leu Asp Glu
```

```
                    20                  25                  30

Asn Lys Gln Leu Ile Leu Ala Ile Leu Glu Asn Gln Asn Leu Gly Lys
            35                  40                  45

Leu Ala Glu Cys Ala Gln Tyr Gln Ala Gln Leu Gln Lys Asn Leu Leu
        50                  55                  60

Tyr Leu Ala Ala Ile Ala Asp Ala Gln Pro Pro Gln Asn Pro Thr Ser
65                  70                  75                  80

His Pro Gln Met Val Gln Pro Gly Ser Met Gln Gly Ala Gly His Tyr
                85                  90                  95

Met Ser Gln Val Pro Met Phe Pro Pro Arg Thr Pro Leu Thr Pro Gln
            100                 105                 110

Gln Met Gln Glu Gln Gln His Gln Gln Leu Gln Gln Gln Gln Ala Gln
        115                 120                 125

Ala Leu Ser Phe Pro Ala Gln Val Val Met Arg Pro Gly Thr Val Asn
    130                 135                 140

Gly Met Gln Gln Pro Met Gln Ala Ala Gly Asp Leu Gln Pro Ala Ala
145                 150                 155                 160

Ala Pro Gly Gly Ser Lys Gln Asp Ala Ala Val Ala Gly Ala Ser Ser
                165                 170                 175

Glu Pro Ser Gly Thr Lys Ser His Lys Asn Ala Gly Ala Glu Glu Val
            180                 185                 190

Gly Ala Asp Val Ala Glu Gln Ser
        195                 200

<210> SEQ ID NO 85
<211> LENGTH: 672
<212> TYPE: DNA
<213> ORGANISM: Vitis vinifera

<400> SEQUENCE: 85
atgcagcagc acctgatgca gatgcagccc atgatggcag cctattaccc cagcaacgtc      60
accactgatc acattcagca gtatcttgat gaaaacaagt cattgattct gaagattgtt     120
gagagccaga attcaggaaa attgactgaa tgtgcagaga accaggcaag actacagaga     180
aacctcatgt acctggctgc aattgctgat tctcaacccc aaccaccac catgcatgct      240 cagttccctc ctagtggcat tgttcagcca ggagctcact acatgcaaca ccaacaagct     300
caacaaatga caccacagtc gctcctggct gcacgctcct ccatgctgta cacccaacaa     360
ccattttcgg ccctgcaaca caacaagcc atccatagcc agcttggcat gggctctggt      420
ggaagtgcag gacttcacat gctgcaaagc gaggggagta atccaggagg caatggaaca     480
ctggggactg gtgggtttcc tgatttcagc cgtggaactt ctggagaagg cctgcaggct     540
gcaggcaggg gaatggctgg tgggagcaag caagatatgg gaaatgcaga agggcgagga     600 ggaactcag gaggtcaggg tgggatgga ggtgagactc tttacttgaa agctgctgaa      660
gatgggaatt ga                                                          672

<210> SEQ ID NO 86
<211> LENGTH: 223
<212> TYPE: PRT
<213> ORGANISM: Vitis vinifera

<400> SEQUENCE: 86

Met Gln Gln His Leu Met Gln Met Gln Pro Met Met Ala Ala Tyr Tyr
1               5                   10                  15

Pro Ser Asn Val Thr Thr Asp His Ile Gln Gln Tyr Leu Asp Glu Asn
            20                  25                  30
```

Lys Ser Leu Ile Leu Lys Ile Val Glu Ser Gln Asn Ser Gly Lys Leu
             35                  40                  45

Thr Glu Cys Ala Glu Asn Gln Ala Arg Leu Gln Arg Asn Leu Met Tyr
         50                  55                  60

Leu Ala Ala Ile Ala Asp Ser Gln Pro Gln Pro Thr Met His Ala
65                  70                  75                  80

Gln Phe Pro Pro Ser Gly Ile Val Gln Pro Gly Ala His Tyr Met Gln
                 85                  90                  95

His Gln Gln Ala Gln Gln Met Thr Pro Gln Ser Leu Leu Ala Ala Arg
            100                 105                 110

Ser Ser Met Leu Tyr Thr Gln Pro Phe Ser Ala Leu Gln Gln Gln
            115                 120                 125

Gln Ala Ile His Ser Gln Leu Gly Met Gly Ser Gly Gly Ser Ala Gly
            130                 135                 140

Leu His Met Leu Gln Ser Glu Gly Ser Asn Pro Gly Gly Asn Gly Thr
145                 150                 155                 160

Leu Gly Thr Gly Gly Phe Pro Asp Phe Ser Arg Gly Thr Ser Gly Glu
                165                 170                 175

Gly Leu Gln Ala Ala Gly Arg Gly Met Ala Gly Gly Ser Lys Gln Asp
            180                 185                 190

Met Gly Asn Ala Glu Gly Arg Gly Gly Asn Ser Gly Gly Gln Gly Gly
            195                 200                 205

Asp Gly Gly Glu Thr Leu Tyr Leu Lys Ala Ala Glu Asp Gly Asn
210                 215                 220

<210> SEQ ID NO 87
<211> LENGTH: 663
<212> TYPE: DNA
<213> ORGANISM: Zea mays

<400> SEQUENCE: 87
atgcagcagc agatgcccat gccgccggcg cccgctgccg ccgcggcggc ggcgcccccg     60
gcggcaggca tcactaccga gcagatccag aagtatttgg acgaaaataa gcaacttatt    120
ttggccatcc tggaaaatca gaacttaggg aagttggctg aatgtgctca gtatcaagct    180
caacttcaaa agaacctctt gtacctggct gcgattgctg atgcccaacc ccagcctccg    240
caaaaccctg caggtcgccc tcagatgatg cagcctggta tagtgccagg tgcggggcat    300
tacatgtcac aagtaccaat gttccctcca agaaccccat taccccacag cagatgcag    360
gagcagcagc aacaacaaca gtttcagcag cagcagcagc aagtgcaggc tcttacattt    420
cctggacaga tggtcatgag accaggcacc atcaacggca tgcagcagca gcagcctatg    480
caggctgacc ctgcccgggc agcagcggag ctgcagcagg cagcacctat cccagctgac    540
gggcgaggaa gcaagcagga caccgcgggt ggggcgagct cagagccttc tgccaatgag    600
agccacaaga gcgccaccgg agcagatacc gaggcaggtg cgacgtggcc gagaaatcc    660
taa                                                                 663

<210> SEQ ID NO 88
<211> LENGTH: 220
<212> TYPE: PRT
<213> ORGANISM: Zea mays

<400> SEQUENCE: 88

Met Gln Gln Gln Met Pro Met Pro Pro Ala Pro Ala Ala Ala Ala Ala
1               5                   10                  15

```
Ala Ala Pro Pro Ala Ala Gly Ile Thr Thr Glu Gln Ile Gln Lys Tyr
            20                  25                  30

Leu Asp Glu Asn Lys Gln Leu Ile Leu Ala Ile Leu Glu Asn Gln Asn
         35                  40                  45

Leu Gly Lys Leu Ala Glu Cys Ala Gln Tyr Gln Ala Gln Leu Gln Lys
 50                  55                  60

Asn Leu Leu Tyr Leu Ala Ala Ile Ala Asp Ala Gln Pro Gln Pro Pro
 65                  70                  75                  80

Gln Asn Pro Ala Gly Arg Pro Gln Met Met Gln Pro Gly Ile Val Pro
                 85                  90                  95

Gly Ala Gly His Tyr Met Ser Gln Val Pro Met Phe Pro Pro Arg Thr
                100                 105                 110

Pro Leu Thr Pro Gln Gln Met Gln Glu Gln Gln Gln Gln Gln Gln Phe
            115                 120                 125

Gln Gln Gln Gln Gln Gln Val Gln Ala Leu Thr Phe Pro Gly Gln Met
        130                 135                 140

Val Met Arg Pro Gly Thr Ile Asn Gly Met Gln Gln Gln Gln Pro Met
145                 150                 155                 160

Gln Ala Asp Pro Ala Arg Ala Ala Glu Leu Gln Gln Ala Ala Pro
                165                 170                 175

Ile Pro Ala Asp Gly Arg Gly Ser Lys Gln Asp Thr Ala Gly Gly Ala
            180                 185                 190

Ser Ser Glu Pro Ser Ala Asn Glu Ser His Lys Ser Ala Thr Gly Ala
        195                 200                 205

Asp Thr Glu Ala Gly Gly Asp Val Ala Glu Lys Ser
    210                 215                 220

<210> SEQ ID NO 89
<211> LENGTH: 2193
<212> TYPE: DNA
<213> ORGANISM: Oryza sativa

<400> SEQUENCE: 89
aatccgaaaa gtttctgcac cgttttcacc ccctaactaa caatataggg aacgtgtgct      60
aaatataaaa tgagacctta tatgtgtagc gctgataact agaactatgc aagaaaaact     120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag atttttttta aaaaaataga     360
atgaagatat tctgaacgta ttggcaaaga tttaaacata taattatata attttatagt     420
ttgtgcattc gtcatatcgc acatcattaa ggacatgtct tactccatcc caattttat     480 ttagtaatta aagacaattg acttattttt attatttatc tttttcgat tagatgcaag     540 gtacttacgc acacactttg tgctcatgtg catgtgtgag tgcacctcct caatacacgt     600
tcaactagca acacatctct aatatcactc gcctatttaa tacatttagg tagcaatatc     660
tgaattcaag cactccacca tcaccagacc acttttaata atatctaaaa tacaaaaaat     720
aattttacag aatagcatga aaagtatgaa acgaactatt taggttttc acatacaaaa     780 aaaaaaagaa ttttgctcgt gcgcgagcgc caatctccca tattgggcac acaggcaaca     840
acagagtggc tgcccacaga acaaccacaa aaaacgatg atctaacgga ggacagcaag     900
tccgcaacaa ccttttaaca gcaggctttg cggccaggag agaggaggag aggcaaagaa     960
aaccaagcat cctcctcctc ccatctataa attcctcccc ccttttcccc tctctatata    1020
```

```
ggaggcatcc aagccaagaa gagggagagc accaaggaca cgcgactagc agaagccgag    1080
cgaccgcctt cttcgatcca tatcttccgg tcgagttctt ggtcgatctc ttccctcctc    1140
cacctcctcc tcacagggta tgtgcccttc ggttgttctt ggatttattg ttctaggttg    1200
tgtagtacgg gcgttgatgt taggaaaggg gatctgtatc tgtgatgatt cctgttcttg    1260
gatttgggat agaggggttc ttgatgttgc atgttatcgg ttcggtttga ttagtagtat    1320
ggttttcaat cgtctggaga gctctatgga aatgaaatgg tttagggtac ggaatcttgc    1380
gattttgtga gtaccttttg tttgaggtaa aatcagagca ccggtgattt tgcttggtgt    1440
aataaaagta cggttgtttg gtcctcgatt ctggtagtga tgcttctcga tttgacgaag    1500
ctatcctttg tttattccct attgaacaaa aataatccaa ctttgaagac ggtcccgttg    1560
atgagattga atgattgatt cttaagcctg tccaaaattt cgcagctggc ttgtttagat    1620
acagtagtcc ccatcacgaa attcatggaa acagttataa tcctcaggaa caggggattc    1680
cctgttcttc cgatttgctt tagtcccaga atttttttc ccaaatatct taaaaagtca    1740
ctttctggtt cagttcaatg aattgattgc tacaaataat gcttttatag cgttatccta    1800
gctgtagttc agttaatagg taatacccct atagtttagt caggagaaga acttatccga    1860
tttctgatct ccatttttaa ttatatgaaa tgaactgtag cataagcagt attcatttgg    1920 attattttt ttattagctc tcaccccttc attattctga gctgaaagtc tggcatgaac    1980
tgtcctcaat tttgttttca aattcacatc gattatctat gcattatcct cttgtatcta    2040
cctgtagaag tttcttttg gttattcctt gactgcttga ttacagaaag aaatttatga    2100
agctgtaatc gggatagtta tactgcttgt tcttatgatt catttccttt gtgcagttct    2160
tggtgtagct tgccactttc accagcaaag ttc                                 2193
```

<210> SEQ ID NO 90
<211> LENGTH: 12
<212> TYPE: PRT
<213> ORGANISM: Artificial sequence
<220> FEATURE:
<223> OTHER INFORMATION: Consensus sequence
<220> FEATURE:
<223> OTHER INFORMATION: box I
<220> FEATURE:
<221> NAME/KEY: MISC_FEATURE
<222> LOCATION: (3)..(3)
<223> OTHER INFORMATION: Xaa can be either Gln or Lys
<220> FEATURE:
<221> NAME/KEY: MISC_FEATURE
<222> LOCATION: (4)..(4)
<223> OTHER INFORMATION: Xaa can be either Tyr, Met, Phe or His
<220> FEATURE:
<221> NAME/KEY: MISC_FEATURE
<222> LOCATION: (6)..(6)
<223> OTHER INFORMATION: Xaa can be either Asp or Glu
<220> FEATURE:
<221> NAME/KEY: MISC_FEATURE
<222> LOCATION: (7)..(7)
<223> OTHER INFORMATION: Xaa can be either Glu or Asp
<220> FEATURE:
<221> NAME/KEY: MISC_FEATURE
<222> LOCATION: (9)..(9)
<223> OTHER INFORMATION: Xaa can be either Lys or Asn
<220> FEATURE:
<221> NAME/KEY: MISC_FEATURE
<222> LOCATION: (10)..(10)
<223> OTHER INFORMATION: Xaa can be any amino acid

<400> SEQUENCE: 90

Ile Gln Xaa Xaa Leu Xaa Xaa Asn Xaa Xaa Leu Ile
1               5                   10

-continued

```
<210> SEQ ID NO 91
<211> LENGTH: 10
<212> TYPE: PRT
<213> ORGANISM: Artificial sequence
<220> FEATURE:
<223> OTHER INFORMATION: Consensus sequence
<220> FEATURE:
<223> OTHER INFORMATION: box II
<220> FEATURE:
<221> NAME/KEY: MISC_FEATURE
<222> LOCATION: (3)..(3)
<223> OTHER INFORMATION: Xaa can be either Met, Leu or Val
<220> FEATURE:
<221> NAME/KEY: misc_feature
<222> LOCATION: (7)..(7)
<223> OTHER INFORMATION: Xaa can be either Ala or Thr

<400> SEQUENCE: 91

Asn Leu Xaa Tyr Leu Ala Xaa Ile Ala Asp
1               5                   10

<210> SEQ ID NO 92
<211> LENGTH: 53
<212> TYPE: DNA
<213> ORGANISM: Artificial sequence
<220> FEATURE:
<223> OTHER INFORMATION: primer: prm06681

<400> SEQUENCE: 92
ggggacaagt ttgtacaaaa aagcaggctt aaacaatgca acagcacctg atg            53

<210> SEQ ID NO 93
<211> LENGTH: 50
<212> TYPE: DNA
<213> ORGANISM: Artificial sequence
<220> FEATURE:
<223> OTHER INFORMATION: primer: prm06682

<400> SEQUENCE: 93
ggggaccact ttgtacaaga aagctgggtc atcattaaga ttccttgtgc                 50

<210> SEQ ID NO 94
<211> LENGTH: 53
<212> TYPE: DNA
<213> ORGANISM: Artificial sequence
<220> FEATURE:
<223> OTHER INFORMATION: primer: prm06685

<400> SEQUENCE: 94
ggggacaagt ttgtacaaaa aagcaggctt aaacaatgca gcagcagcag tct            53

<210> SEQ ID NO 95
<211> LENGTH: 50
<212> TYPE: DNA
<213> ORGANISM: Artificial sequence
<220> FEATURE:
<223> OTHER INFORMATION: primer: prm06686

<400> SEQUENCE: 95
ggggaccact ttgtacaaga aagctgggtt ctttggatcc ttttcacttg                 50

<210> SEQ ID NO 96
<211> LENGTH: 55
<212> TYPE: DNA
<213> ORGANISM: Artificial sequence
<220> FEATURE:
<223> OTHER INFORMATION: primer: prm06683

<400> SEQUENCE: 96
```

```
ggggacaagt tgtacaaaa aagcaggctt aaacaatgca gcaatctcca cagat      55
```

<210> SEQ ID NO 97
<211> LENGTH: 52
<212> TYPE: DNA
<213> ORGANISM: Artificial sequence
<220> FEATURE:
<223> OTHER INFORMATION: primer: prm06684

<400> SEQUENCE: 97

```
ggggaccact ttgtacaaga aagctgggtt cctctatttc attttccttc ag         52
```

<210> SEQ ID NO 98
<211> LENGTH: 46
<212> TYPE: PRT
<213> ORGANISM: Artificial Sequence
<220> FEATURE:
<223> OTHER INFORMATION: SNH domain consensus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 98

```
Ile Gln Xaa Xaa Leu Xaa Xaa Asn Xaa Xaa Leu Ile Xaa Xaa Ile Xaa
1               5                   10                  15

Xaa Xaa Xaa Asn Xaa Gly Xaa Xaa Xaa Glu Cys Xaa Xaa Xaa Gln Xaa
            20                  25                  30

Xaa Leu Xaa Xaa Asn Leu Xaa Tyr Leu Ala Xaa Ile Ala Asp
```

<210> SEQ ID NO 99
<211> LENGTH: 100
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (86)..(95)
<223> OTHER INFORMATION: Xaa can be any naturally occurring amino acid
<220> FEATURE:
<221> NAME/KEY: misc_feature
<222> LOCATION: (97)..(100)
<223> OTHER INFORMATION: Xaa can be any naturally occurring amino acid

<400> SEQUENCE: 99

Xaa Xaa Xaa Xaa Xaa Xaa Xaa Xaa Gln Gln Xaa Met Gln Met Xaa Pro
1               5                   10                  15

Xaa Xaa Xaa Xaa Met Met Ala Ala Tyr Xaa Pro Xaa Xaa Xaa Ile Thr
            20                  25                  30

Thr Glu Gln Ile Gln Lys Tyr Leu Asp Glu Asn Lys Xaa Leu Ile Leu
        35                  40                  45

Ala Ile Leu Glu Asn Gln Asn Leu Gly Lys Leu Ala Glu Cys Ala Gln
    50                  55                  60

Tyr Gln Ala Xaa Leu Gln Lys Asn Leu Met Tyr Leu Ala Ala Ile Ala
65                  70                  75                  80

Asp Ala Gln Pro Gln Xaa Xaa Xaa Xaa Xaa Xaa Xaa Xaa Xaa Xaa Pro
            85                  90                  95

Xaa Xaa Xaa Xaa
        100

<210> SEQ ID NO 100
<211> LENGTH: 324
<212> TYPE: PRT
<213> ORGANISM: Artificial Sequence
<220> FEATURE:
<223> OTHER INFORMATION: Consensus sequence

```
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (86)..(95)
<223> OTHER INFORMATION: Xaa can be any naturally occurring amino acid
<220> FEATURE:
<221> NAME/KEY: misc_feature
<222> LOCATION: (97)..(100)
<223> OTHER INFORMATION: Xaa can be any naturally occurring amino acid
<220> FEATURE:
<221> NAME/KEY: misc_feature
<222> LOCATION: (103)..(105)
<223> OTHER INFORMATION: Xaa can be any naturally occurring amino acid
<220> FEATURE:
<221> NAME/KEY: misc_feature
<222> LOCATION: (107)..(110)
<223> OTHER INFORMATION: Xaa can be any naturally occurring amino acid
<220> FEATURE:
<221> NAME/KEY: misc_feature
<222> LOCATION: (112)..(114)
<223> OTHER INFORMATION: Xaa can be any naturally occurring amino acid
<220> FEATURE:
<221> NAME/KEY: misc_feature
<222> LOCATION: (116)..(120)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (129)..(150)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(169)
<223> OTHER INFORMATION: Xaa can be any naturally occurring amino acid
<220> FEATURE:
<221> NAME/KEY: misc_feature
<222> LOCATION: (173)..(186)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
```

-continued

```
<220> FEATURE:
<221> NAME/KEY: misc_feature
<222> LOCATION: (191)..(195)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (207)..(208)
<223> OTHER INFORMATION: Xaa can be any naturally occurring amino acid
<220> FEATURE:
<221> NAME/KEY: misc_feature
<222> LOCATION: (211)..(224)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (230)..(233)
<223> OTHER INFORMATION: Xaa can be any naturally occurring amino acid
<220> FEATURE:
<221> NAME/KEY: misc_feature
<222> LOCATION: (235)..(248)
<223> OTHER INFORMATION: Xaa can be any naturally occurring amino acid
<220> FEATURE:
<221> NAME/KEY: misc_feature
<222> LOCATION: (250)..(254)
<223> OTHER INFORMATION: Xaa can be any naturally occurring amino acid
<220> FEATURE:
<221> NAME/KEY: misc_feature
<222> LOCATION: (258)..(263)
<223> OTHER INFORMATION: Xaa can be any naturally occurring amino acid
<220> FEATURE:
<221> NAME/KEY: misc_feature
<222> LOCATION: (265)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (298)..(307)
<223> OTHER INFORMATION: Xaa can be any naturally occurring amino acid
<220> FEATURE:
<221> NAME/KEY: misc_feature
<222> LOCATION: (310)..(312)
<223> OTHER INFORMATION: Xaa can be any naturally occurring amino acid
<220> FEATURE:
<221> NAME/KEY: misc_feature
<222> LOCATION: (314)..(315)
<223> OTHER INFORMATION: Xaa can be any naturally occurring amino acid
<220> FEATURE:
<221> NAME/KEY: misc_feature
<222> LOCATION: (317)..(318)
<223> OTHER INFORMATION: Xaa can be any naturally occurring amino acid
<220> FEATURE:
<221> NAME/KEY: misc_feature
<222> LOCATION: (323)..(324)
<223> OTHER INFORMATION: Xaa can be any naturally occurring amino acid

<400> SEQUENCE: 100

Xaa Xaa Xaa Xaa Xaa Xaa Xaa Xaa Gln Gln Xaa Met Gln Met Xaa Pro
1               5                   10                  15

Xaa Xaa Xaa Xaa Met Met Ala Ala Tyr Xaa Pro Xaa Xaa Xaa Ile Thr
            20                  25                  30

Thr Glu Gln Ile Gln Lys Tyr Leu Asp Glu Asn Lys Xaa Leu Ile Leu
        35                  40                  45

Ala Ile Leu Glu Asn Gln Asn Leu Gly Lys Leu Ala Glu Cys Ala Gln
    50                  55                  60

Tyr Gln Ala Xaa Leu Gln Lys Asn Leu Met Tyr Leu Ala Ala Ile Ala
```

-continued

```
            65                  70                  75                  80
Asp Ala Gln Pro Gln Xaa Xaa Xaa Xaa Xaa Xaa Xaa Xaa Xaa Pro
                    85                  90                  95
Xaa Xaa Xaa Xaa Gln Met Xaa Xaa Gly Xaa Xaa Xaa Xaa Met Xaa
                100                 105                 110
Xaa Xaa Gly Xaa Xaa Xaa Xaa Xaa Tyr Tyr Met Gln Xaa Pro Gln Ala
            115                 120                 125
Xaa Xaa Xaa Xaa Xaa Xaa Xaa Xaa Xaa Xaa Xaa Xaa Xaa Xaa Xaa
    130                 135                 140
Xaa Xaa Xaa Xaa Xaa Xaa Met Thr Pro Gln Gln Leu Gln Glu Xaa Gln
145                 150                 155                 160
Xaa Xaa Xaa Xaa Xaa Xaa Xaa Xaa Gln Gln Gln Xaa Xaa Xaa Xaa
                165                 170                 175
Xaa Xaa Xaa Xaa Xaa Xaa Xaa Xaa Xaa Gln Xaa Gln Gln Xaa Xaa
                180                 185                 190
Xaa Xaa Xaa Ala Xaa Xaa Gly Gln Met Gly Met Arg Pro Gly Xaa Xaa
            195                 200                 205
Asn Gly Xaa Xaa Xaa Xaa Xaa Xaa Xaa Xaa Xaa Xaa Xaa Xaa Xaa
        210                 215                 220
Met Leu Xaa Xaa Glu Xaa Xaa Xaa Xaa Gly Xaa Xaa Xaa Xaa Xaa
225                 230                 235                 240
Xaa Xaa Xaa Xaa Xaa Xaa Xaa Gly Xaa Xaa Xaa Xaa Xaa Gly Arg
                245                 250                 255
Gly Xaa Xaa Xaa Xaa Xaa Xaa Gly Xaa Xaa Xaa Xaa Xaa Xaa Xaa
            260                 265                 270
Xaa Xaa Xaa Xaa Xaa Xaa Xaa Xaa Xaa Xaa Xaa Xaa Xaa Xaa Xaa
        275                 280                 285
Xaa Xaa Xaa Xaa Xaa Xaa Gly Xaa Gly Xaa Xaa Xaa Xaa Xaa Xaa
        290                 295                 300
Xaa Xaa Xaa Thr Gly Xaa Xaa Xaa Tyr Xaa Xaa Gly Xaa Xaa Ala Glu
305                 310                 315                 320
Asp Gly Xaa Xaa
```